(12) United States Patent
Takahashi et al.

(10) Patent No.: US 12,269,841 B2
(45) Date of Patent: Apr. 8, 2025

(54) PRODUCTION METHOD FOR OLIGONUCLEOTIDES

(71) Applicant: AJINOMOTO CO., INC., Tokyo (JP)

(72) Inventors: Daisuke Takahashi, Kawasaki (JP); Taisuke Ichimaru, Kawasaki (JP); Kunihiro Hirai, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 850 days.

(21) Appl. No.: 17/400,488

(22) Filed: Aug. 12, 2021

(65) Prior Publication Data
US 2021/0371450 A1 Dec. 2, 2021

Related U.S. Application Data

(63) Continuation of application No. PCT/JP2020/005814, filed on Feb. 14, 2020.

(30) Foreign Application Priority Data

Feb. 15, 2019 (JP) ................. 2019-025605

(51) Int. Cl.
*C07H 21/00* (2006.01)
*C07H 1/00* (2006.01)

(52) U.S. Cl.
CPC .............. *C07H 21/00* (2013.01); *C07H 1/00* (2013.01)

(58) Field of Classification Search
CPC ........ C07H 21/00; C07H 1/00; C07H 19/067; C07H 19/073; C07H 19/167; C07H 19/173
USPC ...................................... 536/25.31
See application file for complete search history.

(56) References Cited

U.S. PATENT DOCUMENTS

| 10,919,928 B2 * | 2/2021 | Hirai ................. C07H 21/00 |
| 2010/0197902 A1 | 8/2010 | Fujihara |
| 2012/0296074 A1 | 11/2012 | Hirai et al. |
| 2015/0112053 A1 | 4/2015 | Kim et al. |
| 2015/0315229 A1 | 11/2015 | Nonogawa |
| 2018/0282365 A1 | 10/2018 | Hirai et al. |
| 2019/0169223 A1 | 6/2019 | Sugawara |

FOREIGN PATENT DOCUMENTS

| EP | 2 816 053 A1 | 12/2014 |
| JP | 61-165399 A | 7/1986 |
| JP | 2003-2895 A | 1/2003 |
| JP | 2003-313198 A | 11/2003 |
| WO | WO 2005/070859 A1 | 8/2005 |
| WO | WO 2009/028345 A1 | 3/2009 |
| WO | WO 2012/157723 A1 | 11/2012 |
| WO | WO 2013/122236 A1 | 8/2013 |
| WO | WO 2013/179412 A1 | 12/2013 |
| WO | WO 2014/077292 A1 | 5/2014 |
| WO | WO 2017/086397 A1 | 5/2017 |
| WO | WO 2017/104836 A1 | 6/2017 |
| WO | WO 2018/203574 A1 | 11/2018 |
| WO | WO 2018/212236 A1 | 11/2018 |

OTHER PUBLICATIONS

Froehler, Published 1993, "Oligodeoxynucleotide Synthesis: H-Phosphonate Approach" (Chapter 4) in Agrawal, S, Methods in Molecular Biology vol. 20: Protocols for Oligonucleotide and Analogs: Synthesis and Properties (New Jersey, Humana Press, 1993), pp. 63-80 (Year: 1993).*
International Search Report issued Mar. 17, 2020 in PCT/JP2020/005814, 2 pages.
Chinese Office Action issued Apr. 25, 2024 in Chinese Application No. 202080014095.6, 8 pgs.
Maria V. Panova et al., Arabinofuranose 1,2,5-orthobenzoate as a single precursor of linear α(1-5)-linked oligoarabinofuranosides, Carbohydrate Research, 456,(2018), 35-44.
Polina I. Abronina et al., A Practical Silicon-Free Strategy for Differentiation of Hydroxy Groups in Arabinofuranose Derivatives, Synthesis, 2012, 44, 1219-1225.

* cited by examiner

*Primary Examiner* — Yih-Horng Shiao
*Assistant Examiner* — Jaret J Crews
(74) *Attorney, Agent, or Firm* — Oblon, McClelland, Maier & Neustadt, L.L.P.

(57) ABSTRACT

A method for producing an oligonucleotide, including a step of removing a temporary protecting group of a 5'-hydroxyl group by adding an acid to a protected oligonucleotide having a phosphorothioate (PS), phosphate (PO) or H-phosphonate moiety, and deacylating a by-product having an acylated 5'-hydroxyl group by solvolysis can complete a condensation reaction to improve a condensation yield, and can markedly reduce impurities such as single base deletion form (N-1mer) and the like.

9 Claims, No Drawings

PRODUCTION METHOD FOR OLIGONUCLEOTIDES

CROSS REFERENCES TO RELATED APPLICATIONS

This application is a continuation of International Patent Application No. PCT/JP2020/005814, filed on Feb. 14, 2020, and claims priority to Japanese Patent Application No. 2019-025605, filed on Feb. 15, 2019, both of which are incorporated herein by reference in their entireties.

BACKGROUND OF THE INVENTION

Field of the Invention

The present invention relates to production methods of oligonucleotides.

Discussion of the Background

At present, the phosphoramidite method and the H-phosphonate method are widely used as methods for producing oligonucleotides, and the dihalophosphine method and the oxazaphosphoridine method are also known. The production of oligonucleotides requires many steps of reaction. Therefore, even if a trace amount of impurity of 1% or less is by-produced in the reaction process for each base extension, a large amount of impurity is produced in the case of an oligonucleotide elongation form to be the target. To obtain a high-purity oligonucleotide, therefore, it is important to suppress by-production of impurities in each reaction single step. However, in the condensation reaction step, the reaction is not completed, not only the yield of the desired oligonucleotide decreases, but also impurities such as a single base deletion form (N-1mer) and the like are by-produced, and a problem also occurs that removal of these impurities is difficult.

The production method of oligonucleotide includes solid 35 phase synthesis (solid phase method) and a liquid phase method. To overcome the defects of the solid phase method and the liquid phase method, a liquid phase method using a pseudo solid phase protecting group is also developed (see WO 2012/157723, WO 2013/122236, WO 2017/104836, WO 2005/070859, WO 2013/179412, WO 2014/077292, WO 2017/086397, WO 2018/20357-4, and WO 2018/212236, all of which are incorporated herein by reference in their entireties).

SUMMARY OF THE INVENTION

Accordingly, it is one object of the present invention to provide novel production methods of oligonucleotides which can complete a condensation reaction of nucleoside, nucleotide or oligonucleotide.

These and other objects, which will become apparent during the following detailed description, have been achieved by the inventors' discovery that, in a deprotection step with an acid (carboxylic acid), which is a pre-step of the condensation reaction, a deprotected 5'-hydroxyl group is acylated with an acid (carboxylic acid), and the condensation reaction cannot be completed, which leads to the by-production of base-deleted impurities. Furthermore, based on this finding, they have found that the aforementioned problem can be solved by newly introducing a step of deacylating the above-mentioned O-acylated oligonucleotide by solvolysis, which resulted in the completion of the present invention. Thus, the present invention provides:

[1] A method for producing an oligonucleotide, comprising a step of removing a temporary protecting group of a 5'-hydroxyl group by adding an acid to a protected oligonucleotide having a phosphorothioate (PS), phosphate (PO) or H-phosphonate moiety, and deacylating a by-product having an acylated 5'-hydroxyl group by solvolysis.

[2] A method for producing an oligonucleotide, comprising the following steps (1)-(4):
  (1) a step of condensing a nucleoside, nucleotide or oligonucleotide (a) wherein a 5'-hydroxy group is not protected, and other groups are each optionally protected by a protecting group used for nucleic acid synthesis or bonded to a solid phase carrier, and
  a nucleoside, nucleotide or oligonucleotide (b) wherein a 3'-hydroxyl group or a 3'-amino group is modified by a method selected from a phosphoramidite method, an H-phosphonate method, a dihalophosphine method and an oxazaphospholidine method, the 5'-hydroxyl group is protected by a temporary protecting group that can be removed under acidic conditions, and other groups are each optionally protected by a protecting group used for nucleic acid synthesis to obtain a phosphite form or phosphorous acid diester (c) in which the 5'-hydroxyl group is protected by a temporary protecting group that can be removed under acidic conditions;
  (2): a step of (2-1) sulfurizing the phosphite form or phosphorous acid diester (c) by adding a sulfurizing agent to obtain an oligonucleotide (d-1) having a phosphorothioated moiety in which the 5'-hydroxyl group is protected by a temporary protecting group that can be removed under acidic conditions, or
  (2-2) oxidizing the phosphite form or phosphorous acid diester (c) by adding an oxidizing agent to obtain an oligonucleotide (d-2) having a phosphated moiety in which the 5'-hydroxyl group is protected by a temporary protecting group that can be removed under acidic conditions;
  (3): a step of (3-1) adding an acid to the oligonucleotide (d-1) having a phosphorothioated moiety to remove the temporary protecting group of the 5'-hydroxyl group, thereby obtaining a crude product of an oligonucleotide (e-1) having a phosphorothioated moiety in which the 5'-hydroxyl group is not protected, or
  (3-2) adding an acid to the oligonucleotide (d-2) having a phosphated moiety to remove the temporary protecting group of the 5'-hydroxyl group, thereby obtaining a crude product of an oligonucleotide (e-2) having a phosphated moiety in which the 5'-hydroxyl group is not protected; and
  (4): a step of (4-1) deacylating by solvolysis the oligonucleotide having an acylated 5'-hydroxyl group, which is contained in a crude product of the oligonucleotide (e-1) having a phosphorothioated moiety, or
  (4-2) deacylating by solvolysis the oligonucleotide having an acylated 5'-hydroxyl group contained in a crude product of the oligonucleotide (e-2) having a phosphated moiety.

[3] The production method of (2), further comprising a step of removing all protecting groups of the oligonucleotide (e-1) having the phosphorothioated moiety or oligonucleotide (e-2) having the phosphated moiety, and then isolating an oligonucleotide having an unprotected phosphorothioated moiety or an oligonucleotide having an unprotected phosphated moiety.

[4] A method for producing an oligonucleotide, comprising the following steps (1A), (3A) and (4A):
- (1A) a step of obtaining a phosphite form or phosphorous acid diester (c) in which the 5'-hydroxyl group is protected by a temporary protecting group that can be removed under acidic conditions by condensing a nucleoside, nucleotide or oligonucleotide (a) wherein a 5'-hydroxy group is not protected, and other groups are each optionally protected by a protecting group used for nucleic acid synthesis or bonded to a solid phase carrier, and
  a nucleoside, nucleotide or oligonucleotide (b) wherein a 3'-hydroxyl group or a 3'-amino group is modified by an H-phosphonate method, the 5'-hydroxyl group is protected by a temporary protecting group that can be removed under acidic conditions, and other groups are each optionally protected by a protecting group used for nucleic acid synthesis;
- (3A) a step of adding an acid to the phosphite form or phosphorous acid diester (c) to remove the temporary protecting group of the 5'-hydroxyl group, thereby obtaining a phosphite form or a crude product of a phosphorous acid diester (c) wherein the 5'-hydroxyl group is not protected; and
- (4A) a step of solvolyzing the oligonucleotide having an acylated 5'-hydroxyl group contained in the phosphite form or a crude product of phosphorous acid diester (c) to achieve deacylation.

[5] The production method of (2) or (3), wherein the step (1) is a step of condensing
- a nucleoside, nucleotide or oligonucleotide (a) wherein a 5'-hydroxy group is not protected, at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions, and other groups are each optionally further protected by a protecting group used for nucleic acid synthesis, or
- a nucleoside, nucleotide or oligonucleotide (a1) wherein a 5'-hydroxy group is not protected, one OH of a 3'-terminal phosphate group is replaced by —OL$^{n1}$-OH wherein L$^{n1}$ is an organic group, the hydroxy group of —OL$^{n1}$-OH is protected by a protecting group unremovable under acidic conditions but removable under basic conditions, and other groups are each optionally further protected by a protecting group used for nucleic acid synthesis, and
- a nucleoside, nucleotide or oligonucleotide (b) wherein a 3'-hydroxy group or 3'-amino group is modified by a method selected from a phosphoramidite method, an H-phosphonate method, a dihalophosphine method and an oxazaphospholidine method, a 5'-hydroxy group is protected by a temporary protecting group removable under acidic conditions, and other groups are each optionally further protected by a protecting group selected from protecting groups unremovable under acidic conditions but removable under basic conditions and protecting groups used for nucleic acid synthesis to obtain a phosphite form or phosphorous acid diester (c) in which the 5'-hydroxyl group is protected by a temporary protecting group that can be removed under acidic conditions.

[6] The production method of any one of (1) to (5), wherein the acid used for removing the temporary protecting group of the 5'-hydroxyl group comprises carboxylic acid, sulfonic acid, phosphonic acid, or phosphoric acid.

[7] The production method of (6), wherein the acid is trifluoroacetic acid, dichloroacetic acid, trichloroacetic acid, acetic acid, trifluoromethanesulfonic acid, methanesulfonic acid, p-toluenesulfonic acid, phosphonic acid, or phosphoric acid.

[8] The production method of any one of (1) to (7), wherein the solvent used for solvolysis is a mixture of a base and a nucleophilic substance.

[9] The production method of (8), wherein the base is at least one kind selected from the group consisting of a non-nucleophilic base and a heterocyclic compound containing a nitrogen atom, and the nucleophilic substance is at least one kind selected from the group consisting of water and an alcohol derivative.

[10] The production method of (9), wherein the non-nucleophilic base has a pK$_a$ of 3 to 10.

[11] The production method of (9) or (10), wherein the heterocyclic compound containing a nitrogen atom is a pyridine derivative.

[12] The production method of any one of (8) to (11), wherein a pH of the nucleophilic substance is 3.0 to 8.0 when it comprises water.

[13] The production method of any one of (8) to (12), wherein the base is at least one kind selected from the group consisting of pyridine, collidine, lutidine and methylpyridine.

[14] The production method of any one of (8) to (13), wherein the nucleophilic substance is at least one kind selected from the group consisting of water, methanol, ethanol, isopropyl alcohol, butanol, benzyl alcohol and tetrahydrofurfuryl alcohol.

(14A) The production method of any one of (8) to (14), wherein the mixture of a base and a nucleophilic substance is a mixture of pyridine and water, a mixture of pyridine and methanol, or a mixture of pyridine and ethanol.

[15] A method for producing an oligonucleotide, comprising a step of removing a temporary protecting group of a 3'-hydroxyl group or a 3'-amino group by adding an acid to a protected oligonucleotide having a phosphorothioate (PS), phosphate (PO) or H-phosphonate moiety, and deacylating a by-product with an acylated 3'-hydroxyl group or 3'-amino group by solvolysis.

[16] A method for producing an oligonucleotide, comprising the following steps (1')-(4'):
- (1') a step of condensing a nucleoside, nucleotide or oligonucleotide (a') wherein a 3'-hydroxyl group or 3'-amino group is not protected, and other groups are each optionally protected by a protecting group used for nucleic acid synthesis or bonded to a solid phase carrier, and
  a nucleoside, nucleotide or oligonucleotide (b') wherein a 5'-hydroxyl group is modified by a method selected from a phosphoramidite method, an H-phosphonate method, a dihalophosphine method and an oxazaphospholidine method, the 3'-hydroxyl group or 3'-amino group is protected by a temporary protecting group that can be removed under acidic conditions, and other groups are each optionally protected by a protecting group used for nucleic acid synthesis to obtain a phosphite form or phosphorous acid diester (c') in which the 3'-hydroxyl group or 3'-amino group is protected by a temporary protecting group that can be removed under acidic conditions;
- (2'): a step of (2'-1) sulfurizing the phosphite form or phosphorous acid diester (c') by adding a sulfurizing agent to obtain oligonucleotide (d'-1) having a phosphorothioated moiety in which the 3'-hydroxyl group or 3'-amino group is protected by a temporary protecting group that can be removed under acidic conditions, or (2'-2) oxidizing the phosphite form or phosphorous acid diester (c') by adding an oxidizing agent to obtain oligonucleotide (d'-2) having a phosphated moiety in which the 3'-hydroxyl group or 3'-amino group is protected by a temporary protecting group that can be removed under acidic conditions;

(3'): a step of (3'-1) adding an acid to the oligonucleotide (d'-1) having a phosphorothioated moiety to remove the temporary protecting group of the 3'-hydroxyl group or 3'-amino group, thereby obtaining a crude product of an oligonucleotide (e'-1) having a phosphorothioated moiety in which the 3'-hydroxyl group or 3'-amino group is not protected, or (3'-2) adding an acid to the oligonucleotide (d'-2) having a phosphated moiety to remove the temporary protecting group of the 3'-hydroxyl group or 3'-amino group, thereby obtaining a crude product of an oligonucleotide (e'-2) having a phosphated moiety in which the 3'-hydroxyl group or 3'-amino group is not protected; and (4'): a step of (4'-1) solvolyzing the oligonucleotide having a phosphorothioated moiety in which the 3'-hydroxyl group or 3'-amino group is acylated, and contained in a crude product of the oligonucleotide (e'-1) having a phosphorothioated moiety, or (4'-2) solvolyzing the oligonucleotide having a phosphated moiety in which the 3'-hydroxyl group or 3'-amino group is acylated, and contained in a crude product of the oligonucleotide (e'-2) having a phosphated moiety.

Advantageous Effects of Invention

According to the method for producing oligonucleotide of the present invention, the condensation reaction can be completed to improve the condensation yield, and impurities such as single base deletion form (N-1mer) and the like can be markedly reduced.

DETAILED DESCRIPTION OF THE PREFERRED EMBODIMENTS

Terms

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" to be the constitutional unit of oligonucleotide means a compound wherein a nucleic acid base is bonded to the 1'-position of a sugar (e.g., 2-deoxyribose or ribose, or 2-deoxyribose or ribose wherein 2-position carbon atom and 4-position carbon atom are bonded by a divalent organic group, or the like) by N-glycosidation.

In the present specification, the "sugar" also encompasses an amino sugar wherein a hydroxy group is replaced by an amino group, and ribose wherein a 2-hydroxy group is replaced by a halogen atom.

Examples of the 2-deoxyribose or ribose wherein 2-position carbon atom and 4-position carbon atom are bonded by a divalent organic group include the following compounds.

In the following formulas, R is any of a hydrogen atom, a substituted or unsubstituted hydrocarbon group, a substituted or unsubstituted hydroxyl group, and a substituted or unsubstituted amino group, and R' is either a hydrogen atom or a hydroxyl group.

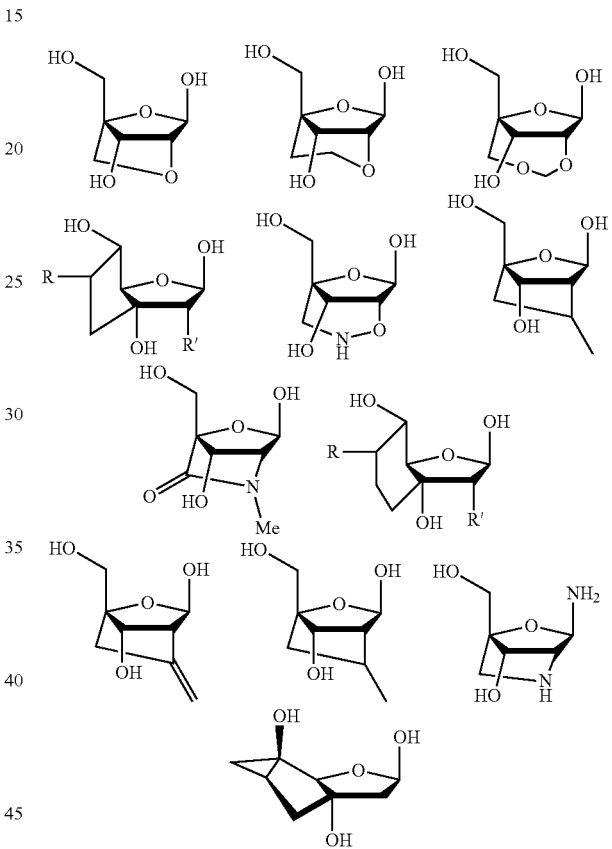

Examples of the amino sugar include 2-deoxyribose wherein 3-hydroxy group is replaced by amino group, ribose wherein 3-hydroxy group is replaced by amino group, and ribose wherein 3-hydroxy group is replaced by amino group and 2-hydroxy group is replaced by halogen, shown below (in the following formulas, $X^s$ is a halogen atom).

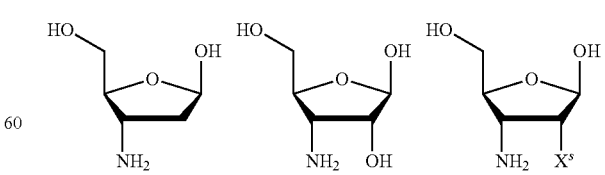

In the present specification, the "phosphate group" encompasses not only —O—P(O) (OH)$_2$ but also a group wherein oxygen atom is replaced by sulfur atom or NH (e.g., —O—P(S) (OH)$_2$, —NH—P(O) (OH)$_2$, —NH—P(S) (OH)

2). In addition, a group wherein hydroxy group (—OH) in the phosphate group is replaced by —OR$^p$ wherein R$_p$ is an organic group such as a protecting group of phosphate group or the like (e.g., protected phosphate group) is also encompassed in the "phosphate group".

In the present specification, the "nucleotide" means a compound wherein phosphate group is bonded to nucleoside. Examples of the nucleotide wherein 3'-hydroxy group or 5'-hydroxy group is replaced by phosphate group include the compounds shown by the following formulas (in the following formulas, R$^{m1}$ and R$^{m2}$ are each independently a hydrogen atom or an organic group (excluding nucleoside residue), X$^m$ is a hydrogen atom, a hydroxy group or halogen atom, R$_1$ and R$_2$ are each a hydrogen atom or an alkyl group, R$_1$ and R$_2$ may be bonded to form a 5- or 6-membered ring, and R$_3$ and R$_4$ are each a hydrogen atom or a phenyl group).

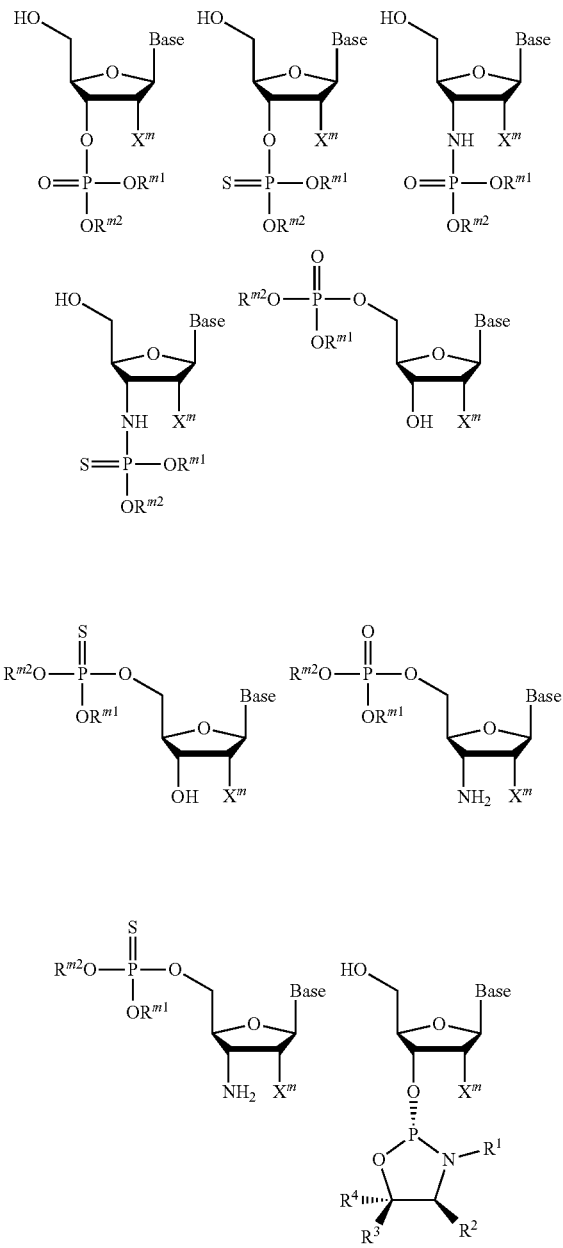

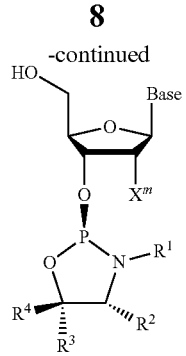

In the present specification, the "oligonucleotide" means a compound wherein one or more nucleotides are bonded to nucleoside. The "oligonucleotide" also encompasses phosphorothioate-type oligonucleotide wherein oxygen atom of phosphate group is replaced by sulfur atom, oligonucleotide wherein —O— of phosphate group is replaced by —NH—, and oligonucleotide wherein hydroxy group (—OH) in phosphate group is replaced by —OR$^p$ wherein R$^p$ is an organic group. While the number of nucleosides in the oligonucleotide of the present invention is not particularly limited, it is preferably 3 to 50, more preferably 5 to 30.

In the present specification, the "solid phase carrier" is not particularly limited as long as it is used for solid phase synthesis of nucleic acid in the pertinent field. Examples thereof include glass bead, resin bead and the like. The solid phase support or resin used as the solid phase carrier may be any support or resin known in the pertinent technical field and suitable for use in solid phase synthesis.

In the present specification, the term "solid phase" includes the binding or linking of nucleoside, nucleotide or oligonucleotide to the above-mentioned solid phase support or resin via a commonly-used functional linker or handle group. Thus, the "solid phase" in this context also includes such linkers. Examples of the solid phase include polystyrene supports (which may be further functionalized by, for example, p-methylbenzyl-hydrylamine), or rigid functionalized supports such as diatomaceous earth-encapsulated polydimethylacrylamide (pepsin K), silica, microporous glass, and the like. The resin matrix of the solid phase may be composed of amphiphilic polystyrene-PEG resin or PEG-polyamide or PEG-polyester resin. Examples of the solid phase carrier include Wang-PEG resin and Link-amide PEG resin.

In the present specification, the "3'-amino group" means an amino group bonded to the 3'-position carbon atom of nucleoside, nucleotide or oligonucleotide.

In the present specification, the "5'-amino group" means an amino group bonded to the 5'-position carbon atom of nucleoside, nucleotide or oligonucleotide.

In the present specification, the "3'-phosphate group" means a phosphate group bonded to the 3'-position carbon atom of nucleotide or oligonucleotide.

In the present specification, the "5'-phosphate group" means a phosphate group bonded to the 5'-position carbon atom of nucleotide or oligonucleotide.

In the present specification, the "nucleic acid base" is not particularly limited as long as it can be used for the synthesis of nucleic acid and includes, for example, pyrimidine bases such as cytosyl group, uracil group, thyminyl group and the like, and purine bases such as adenyl group, guanyl group and the like can be mentioned. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the 5'-position of the nucleotide is preferable.

The "amino-protecting group" is not particularly limited, and examples thereof include the protecting groups described in Greene's PROTECTIVE GROUPS IN ORGANIC SYNTHESIS, 4th edition, Wiley-Interscience, 2006 and the like. Specific examples of the protecting group include, pivaloyl group, pivaloyloxymethyl group, acetyl group, trifluoroacetyl group, phenoxyacetyl group, 4-isopropylphenoxyacetyl group, 4-tert-butylphenoxyacetyl group, benzoyl group, isobutyryl group, (2-hexyl)decanoyl group, dimethylformamidinyl group, 1-(dimethylamino)ethylidene group, 9-fluorenylmethyloxycarbonyl group. Among them, acetyl group, phenoxyacetyl group, 4-isopropylphenoxyacetyl group, benzoyl group, isobutyryl group, (2-hexyl)decanoyl group, dimethylformamidinyl group, and 1-(dimethylamino)ethylidene group is preferable.

The carbonyl group of the nucleic acid base is also optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced.

In addition to the above-mentioned groups, a modified nucleic acid base (e.g., 8-bromoadenyl group, 8-bromoguanyl group, 5-bromocytosyl group, 5-iodocytosyl group, 5-bromouracil group, 5-iodouracil group, 5-fluorouracil group, 5-methylcytosyl group, 8-oxoguanyl group, hypoxanthinyl group etc.), which is a nucleic acid base substituted by any 1 to 3 substituents (e.g., halogen atom, alkyl group, aralkyl group, alkoxy group, acyl group, alkoxyalkyl group, hydroxy group, amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, the "alkyl (group)" may be any of a linear and a branched chain. As the "alkyl (group)", an alkyl group having one or more carbon number can be mentioned. When the carbon number is not particularly limited, it is preferably a $C_{1-10}$ alkyl group, more preferably a $C_{1-6}$ alkyl group, further preferably $C_{1-5}$ alkyl group. When the carbon number is not particularly limited, specific preferable examples include methyl, ethyl, propyl, isopropyl, butyl, isobutyl, sec-butyl, tert-butyl, pentyl, hexyl and the like, and methyl and ethyl are particularly preferable.

In the present specification, the "$C_a$-b" means a carbon number of not less than a and not more than b (a, b are integers).

In the present specification, as the "aralkyl (group)", a $C_{7-20}$ aralkyl group can be mentioned, and a $C_{7-16}$ aralkyl group ($C_{6-10}$ aryl-$C_{1-6}$ alkyl group) is preferable. Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, the "alkoxy (group)" may be any of a linear and a branched chain. As the "alkoxy (group)", an alkoxy group having one or more carbon atoms can be mentioned. When the carbon number is not particularly limited, it is preferably a $C_{1-10}$ alkoxy group, more preferably a $C_{1-6}$ alkoxy group. When the carbon number is not particularly limited, specific preferable examples include methoxy, ethoxy, propoxy, isopropoxy, butoxy, isobutoxy, sec-butoxy, tert-butoxy, pentyloxy, hexyloxy and the like, and methoxy and ethoxy are particularly preferable.

In the present specification, the "acyl (group)" may be any of a linear and a branched chain. Examples of the "acyl (group)" include a $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, the "alkenyl (group)" may be any of a linear and a branched chain. Examples of the "alkenyl (group)" include a $C_{2-6}$ alkenyl group and the like. Specific examples thereof include vinyl, 1-propenyl, allyl, isopropenyl, butenyl, isobutenyl and the like. Among them, a $C_{2-4}$ alkenyl group is preferable.

In the present specification, the "alkynyl (group)" may be any of a linear and a branched chain. Examples of the "alkynyl (group)" include $C_{2-6}$ alkynyl group and the like. Specific examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_{2-4}$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_{3-6}$ cycloalkyl group such as cyclopropyl, cyclobutyl, cyclopentyl, cyclohexyl or the like is preferable, and cyclohexyl is particularly preferable.

In the present specification, the "aryl (group)" means a monocyclic aromatic or polycyclic (fused) aromatic hydrocarbon group. Specific examples thereof include $C_{6-14}$ aryl groups such as phenyl, 1-naphthyl, 2-naphthyl, biphenylyl, 2-anthryl or the like, and the like. Among them, a $C_{6-10}$ aryl group is more preferable and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as alkyl group, alkenyl group, alkynyl group, cycloalkyl group, aryl group, aralkyl group and the like and divalent groups induced therefrom.

In the present specification, examples of the "$C_{6-14}$ hydrocarbocycle" include $C_{6-10}$ cycloalkane, $C_{6-10}$ cycloalkene, $C_{6-14}$ aromatic hydrocarbocycle.

Examples of the "$C_{6-10}$ cycloalkane" include cyclohexane, cycloheptane, cyclooctane.

Examples of the "$C_{6-10}$ cycloalkene" include cyclohexene, cycloheptene, cyclooctene.

Examples of the "$C_{6-14}$ aromatic hydrocarbocycle" include benzene, naphthalene.

In the present specification, the "alkylene (group)" may be any of a linear and a branched chain. As the "alkylene (group)", an alkylene group having a carbon number of one or more can be mentioned. When the range of carbon number is not particularly limited, it is preferably $C_{1-10}$ alkylene group, more preferably $C_{1-6}$ alkylene group. Specific preferable examples include methylene, ethylene, propylene, butylene, pentylene, hexylene, and methylene and ethylene are particularly preferable.

In the present specification, examples of the "linker" include —O—, —C(=O)—, —C(=O)O—, —OC(=O)—, —C(=O)NH—, —NHC(=O)—, —S—, —SO—, —SO$_2$—, —Si(R') (R") O—, —Si(R') (R")—(R', R" are each independently a hydrogen atom or a $C_{1-22}$ hydrocarbon group) and the like.

In the present specification, the "substituent" of the "optionally substituted" encompasses the aforementioned halogen atom, alkyl group, aralkyl group, alkoxy group, acyl group, alkenyl group, alkynyl group, cycloalkyl group, aryl group, as well as hydroxy group, nitro group, cyano group, guanidyl group, carboxy group, alkoxycarbonyl group (the alkoxy moiety is the same as that in the aforementioned alkoxy group), sulfo group, phospho group, alkylthio group (the alkyl moiety is the same as that in the aforementioned alkyl group), alkylsulfinyl group (the alkyl moiety is the same as that in the aforementioned alkyl group), alkylsulfonyl group (the alkyl moiety is the same as that in the aforementioned alkyl group), amino group, monoalkylamino group (the alkyl moiety is the same as that in the aforementioned alkyl group), dialkylamino group (the alkyl moiety is the same as that in the aforementioned alkyl group), oxo group and the like.

Production Method of Oligonucleotide

The production method of the present invention can be applied to any of a liquid phase method (including liquid phase method using pseudo solid phase protecting group) and a solid phase method. It is preferably applied to a liquid phase method (including liquid phase method using pseudo solid phase protecting group).

The production method of the present invention encompasses both an embodiment in which oligonucleotide chain is elongated in the direction of from the 3'-terminal to the 5'-terminal (hereinafter sometimes to be abbreviated as "3'-5' synthesis") and an embodiment in which oligonucleotide chain is elongated in the direction of from the 5'-terminal to the 3'-terminal (hereinafter sometimes to be abbreviated as "5'-3' synthesis"). The production method of the present invention involving 3'-5' synthesis is explained below.

The oligonucleotide may be chiral.

3'-5' Synthesis

The production method of the present invention which is 3'-5' synthesis includes a step of adding an acid to a protected oligonucleotide having a phosphorothioate (PS), phosphate (PO) or H-phosphonate moiety to remove a temporary protecting group of the 5'-hydroxyl group, and solvolyzing a by-product with acylated 5'-hydroxyl group to perform deacylation.

The production method is explained by the following steps (3): deprotection and step (4): solvolysis.

The production method of the present invention which is 3'-5' synthesis also includes the following steps (1)-(4):

(1) a step of condensing a nucleoside, nucleotide or oligonucleotide (a) wherein a 5'-hydroxy group is not protected, and other groups are each optionally protected by a protecting group used for nucleic acid synthesis or bonded to a solid phase carrier, and a nucleoside, nucleotide or oligonucleotide (b) wherein a 3'-hydroxyl group or a 3'-amino group is modified by a method selected from a phosphoramidite method, an H-phosphonate method, a dihalophosphine method and an oxazaphospholidine method, the 5'-hydroxyl group is protected by a temporary protecting group that can be removed under acidic conditions, and other groups are each optionally protected by a protecting group used for nucleic acid synthesis to obtain a phosphite form or phosphorous acid diester (c) in which the 5'-hydroxyl group is protected by a temporary protecting group that can be removed under acidic conditions;

(2): a step of (2-1) sulfurizing the phosphite form or phosphorous acid diester (c) by adding a sulfurizing agent to obtain oligonucleotide (d-1) having a phosphorothioated moiety in which the 5'-hydroxyl group is protected by a temporary protecting group that can be removed under acidic conditions, or (2-2) oxidizing the phosphite form or phosphorous acid diester (c) by adding an oxidizing agent to obtain oligonucleotide (d-2) having a phosphated moiety in which the 5'-hydroxyl group is protected by a temporary protecting group that can be removed under acidic conditions;

(3): a step of (3-1) adding an acid to the oligonucleotide (d-1) having the phosphorothioated moiety to remove the temporary protecting group of the 5'-hydroxyl group, thereby obtaining a crude product of an oligonucleotide (e-1) having a phosphorothioated moiety in which the 5'-hydroxyl group is not protected, or (3-2) adding an acid to the oligonucleotide (d-2) having a phosphated moiety to remove the temporary protecting group of the 5'-hydroxyl group, thereby obtaining a crude product of an oligonucleotide (e-2) having a phosphated moiety in which the 5'-hydroxyl group is not protected; and (4): a step of (4-1) deacylating by solvolysis the oligonucleotide having an acylated 5'-hydroxyl group, which is contained in a crude product of the oligonucleotide (e-1) having the phosphorothioated moiety, or (4-2) deacylating by solvolysis the oligonucleotide having an acylated 5'-hydroxyl group contained in a crude product of the oligonucleotide (e-2) having the phosphated moiety.

By repeating the cycle of steps (1)-(4), the oligonucleotide chain can be extended.

Step (1) (Condensation)

In this step, a nucleoside, nucleotide or oligonucleotide (a) wherein a 5'-hydroxy group is not protected, and other groups are each optionally protected by a protecting group used for nucleic acid synthesis or bonded to a solid phase carrier, and a nucleoside, nucleotide or oligonucleotide (b) wherein a 3'-hydroxyl group or a 3'-amino group is modified by a method selected from a phosphoramidite method, an H-phosphonate method, a dihalophosphine method and an oxazaphospholidine method, the 5'-hydroxyl group is protected by a temporary protecting group that can be removed under acidic conditions, and other groups are each optionally protected by a protecting group used for nucleic acid synthesis are condensed to obtain a phosphite form or phosphorous acid diester (c) in which the 5'-hydroxyl group is protected by a temporary protecting group that can be removed under acidic conditions.

When the production method of the present invention is a solid phase method, the nucleoside, nucleotide or oligonucleotide (a) has, for example, the 3'-position bonded to a solid phase carrier via a linker generally used in the pertinent field.

In a preferred embodiment of this step, a nucleoside, nucleotide or oligonucleotide (a) wherein a 5'-hydroxy group is not protected, at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions, and other groups are each optionally protected by a protecting group used for nucleic acid synthesis, or a nucleoside, nucleotide or oligonucleotide (a1) wherein a 5'-hydroxy group is not protected, one OH of a 3'-terminal phosphate group is replaced by —OL$^{n1}$-OH wherein L$^{n1}$ is an organic group, the hydroxy group of —OL$^{n1}$-OH is protected by a protecting group unremovable under acidic conditions but removable under basic conditions, and other groups are each optionally protected by a protecting group used for nucleic acid synthesis, and a nucleoside, nucleotide or oligonucleotide (b) wherein a 3'-hydroxy group or 3'-amino group is modified by a method selected from a phosphoramidite method, an H-phosphonate method, a dihalophosphine method and an oxazaphospholidine method, a 5'-hydroxy group is protected by a temporary protecting group removable under acidic conditions, and other groups are each optionally protected by a protecting group selected from protecting groups unremovable under acidic conditions but removable under basic conditions and protecting groups used for nucleic acid synthesis to obtain a phosphite form or phosphorous acid diester (c) in which the 5'-hydroxyl group is protected by a temporary protecting group that can be removed under acidic conditions are used.

In the nucleoside, nucleotide or oligonucleotide (a), the 2'-position may be halogenated (e.g., fluorinated).

The organic group for L$^{n1}$ means a group in which a hydrocarbon group or a carbon atom in a hydrocarbon group is replaced by a hetero atom. Examples of the hetero atom include oxygen atom, nitrogen atom, sulfur atom and the like. The organic group may have a substituent such as hydroxy group, amino group, oxo group (=O) or the like. The hydroxy group and the amino group that the organic group may have are preferably protected by a protecting group. The shape of the organic group may be a chain (linear or branched chain), a ring or a combination of these.

The organic group may have a group having functionality to cells. The group having functionality to cells is preferably bonded to a terminal of the main chain or a side chain of the organic group. Examples of the group having functionality to cells include "a group that improves cellular membrane permeability of a compound by improving liposolubility of the compound", "a group that improves intracellular uptake of a compound via cellular membrane receptor" and the like. Examples of the "group that improves cellular membrane permeability of a compound by improving liposolubility of the compound" include cholesterol residue, tocopherol residue and the like. Examples of the "group that improves intracellular uptake of a compound via cellular membrane receptor" include N-acetylgalactosamine residue and the like. These groups that have functionality for cells are described in WO2017/104836.

Specific examples of —OL$^{n1}$-OH include the following (in the following formulas, * shows the bonding position to phosphorus atom and Ac is an acetyl group).

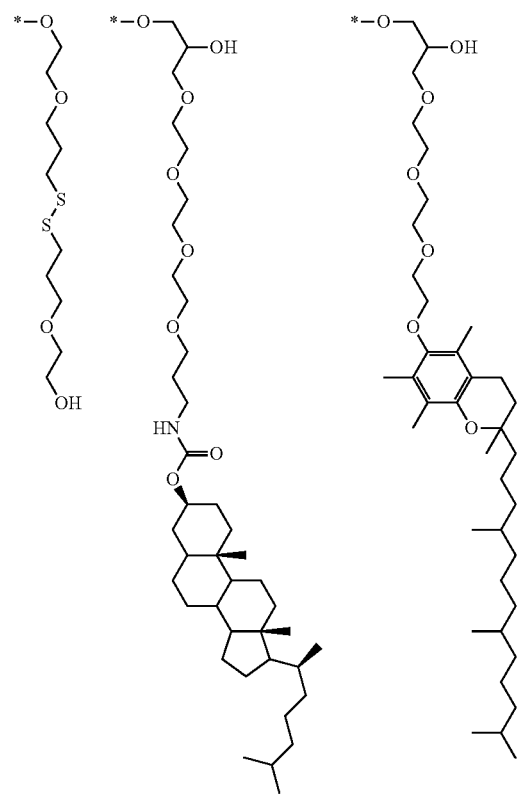

-continued

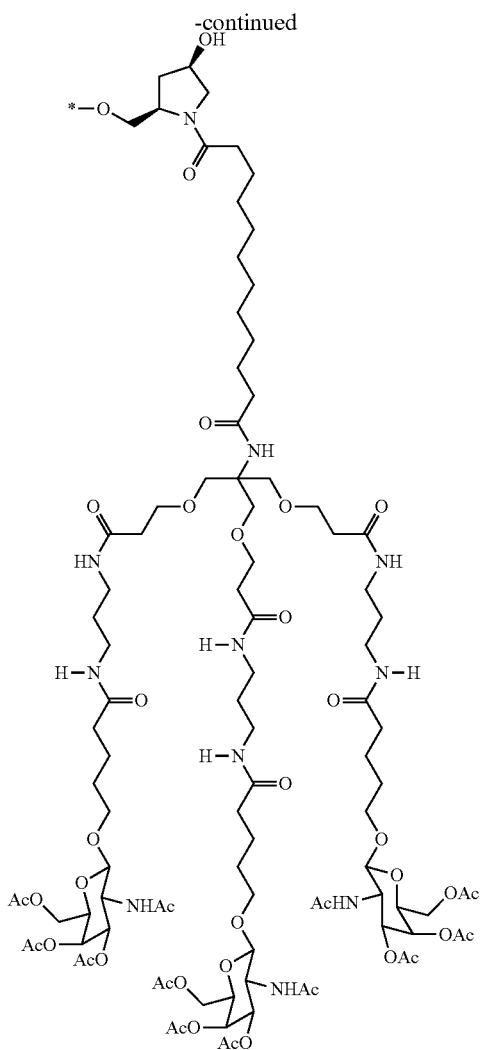

$L^{n1}$ is preferably a $C_{2-6}$ alkylene group, more preferably an ethylene group.

In a more preferred embodiment of this step, a nucleoside or oligonucleotide (a) wherein a 5'-hydroxy group is not protected, at least one group selected from an amino group and an imino group of a nucleic acid base, a 2'-hydroxy group and a 3'-hydroxy group of a ribose residue, and a 3'-hydroxy group of a deoxyribose residue is protected by a protecting group unremovable under acidic conditions but removable under basic conditions, and other groups are each optionally protected by a protecting group used for nucleic acid synthesis, and a nucleoside or oligonucleotide (b) wherein a 3'-hydroxyl group is modified by a method selected from a phosphoramidite method, an H-phosphonate method, a dihalophosphine method and an oxazaphospholidine method, a 5'-hydroxy group is protected by a temporary protecting group removable under acidic conditions, and other groups are each optionally protected by a protecting group used for nucleic acid synthesis are used.

In the case of a liquid phase method, while the concentration of the nucleoside, nucleotide or oligonucleotide (a) or the nucleotide or oligonucleotide (a1) used in this step in the solution is not particularly limited as long as it is dissolved in a solvent, it is preferably 1 to 30 wt %.

The amino groups of the nucleoside, nucleotide or oligonucleotide (a), the nucleotide or oligonucleotide (a1) and the nucleoside, nucleotide or oligonucleotide (b) are preferably protected by the aforementioned protecting groups. As the protecting group, cetyl group, phenoxyacetyl group, 4-isopropylphenoxyacetyl group, benzoyl group, isobutyryl group, (2-hexyl)decanoyl group, dimethylformamidinyl group, and 1-(dimethylamino)ethylidene group are preferable. When the nucleoside, nucleotide or oligonucleotide (a) and the nucleoside, nucleotide or oligonucleotide (b) has plural amino groups, only one kind of the amino-protecting group may be used or two or more kinds thereof may be used.

In the nucleoside, nucleotide or oligonucleotide (a), at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions. In the nucleoside, nucleotide or oligonucleotide (a), at least one group selected from an amino group and an imino group of a nucleic acid base, a 3'-hydroxy group of a ribose residue, and a 3'-hydroxy group of a deoxyribose residue, more preferably a 3'-hydroxy group of a ribose residue or a 3'-hydroxy group of a deoxyribose residue, is preferably protected by the aforementioned protecting group.

In the nucleotide or oligonucleotide (a1), the hydroxy group of $—OL^{n1}$-OH is protected by a protecting group unremovable under acidic conditions but removable under basic conditions.

The "protecting group unremovable under acidic conditions but removable under basic conditions" of the nucleoside, nucleotide or oligonucleotide (a) and the nucleotide or oligonucleotide (a1), and the "protecting group unremovable under acidic conditions but removable under basic conditions" that the nucleoside, nucleotide or oligonucleotide (b) optionally has are each independently and preferably a protecting group having a linear aliphatic hydrocarbon group having a carbon number of not less than 10 or an organic group having at least one aliphatic hydrocarbon group having one or more branched chains and having a total carbon number of not less than 14 and not more than 300 (hereinafter sometimes to be abbreviated as a "pseudo solid phase protecting group"), to efficiently perform solid-liquid separation or extraction.

The pseudo solid phase protecting group imparts hydrophobicity to the nucleoside, nucleotide or oligonucleotide (a) and the nucleotide or oligonucleotide (a1) (and the nucleoside, nucleotide or oligonucleotide (b) in some cases) and improves solubility in non-polar solvents. It can also decrease solubility in polar solvents. The nucleoside, nucleotide or oligonucleotide (a) and the nucleotide or oligonucleotide (a1) which are each protected by such pseudo solid phase protecting group can perform a condensation reaction in the liquid phase of a non-polar solvent. By adding a polar solvent to the reaction solution in the subsequent solid-liquid separation or extraction, the pseudo solid phase protecting group-protected oligonucleotide (e) precipitates and solid-liquid separation thereof can be performed. Alternatively, in the solid-liquid separation or extraction, a polar solvent is added to the reaction solution, layers are separated between the polar solvent and non-polar solvent, and the oligonucleotide (e) is transferred to the non-polar solvent, whereby the extraction thereof can be performed. As such pseudo solid phase protecting group, for example, those described in WO 2012/157723, WO 2013/122236, WO 2017/104836, WO 2013/179412, WO 2014/077292, WO 2017/086397, WO 2018/203574, WO 2018/212236, all of which are incorporated herein by reference in their entireties, can be used.

The "protecting group used for nucleic acid synthesis" is not particularly limited as long as it is generally used in the field of nucleic acid synthesis, and includes the abovementioned low-molecular-weight protecting groups. For purification by solid-liquid separation, the pseudo solid phase protecting group is preferably a protecting group having a linear aliphatic hydrocarbon group having a carbon number of not less than 10. For purification by extraction, the pseudo solid phase protecting group is preferably a protecting group having an organic group having at least one aliphatic hydrocarbon group having one or more branched chains and having a total carbon number of not less than 14 and not more than 300.

A pseudo solid phase protecting group preferable for solid-liquid separation is explained first. Examples of the pseudo solid phase protecting group preferable for solid-liquid separation include a protecting group having a $C_{6-14}$ hydrocarbocycle bonded, via a linker, to a hydrocarbon group wherein a linear aliphatic hydrocarbon group having a carbon number of not less than 10 is bonded via a single bond or a linker.

The aforementioned linear aliphatic hydrocarbon group having a carbon number of not less than 10 is preferably selected from a linear $C_{10-40}$ alkyl group and a linear $C_{10-40}$ alkenyl group, more preferably a linear $C_{10-40}$ alkyl group, further preferably a linear $C_{10-30}$ alkyl group, particularly preferably a linear $C_{12-28}$ alkyl group, most preferably a linear $C_{14-26}$ alkyl group.

The aforementioned linker is preferably selected from —O—, —C(=O)—, —C(=O)O—, —OC(=O)—, —C(=O)NH—, —NHC(=O)—, —S—, —SO—, —SO$_2$—, and —Si(R') (R")O—, —Si(R') (R")—(R', R" are each independently a hydrogen atom or a $C_{1-22}$ hydrocarbon group), more preferably selected from —O—, —C(=O)—, —C(=O)O—, —OC(=O)—, —C(=O)NH— and —NHC(=O)—, further preferably —O—.

The aforementioned $C_{6-14}$ hydrocarbocycle is preferably selected from a benzene ring, a naphthalene ring and a cyclohexane ring, more preferably selected from a benzene ring and a cyclohexane ring, further preferably a benzene ring.

The pseudo solid phase protecting group preferable for solid-liquid separation is preferably a protecting group having a benzene ring bonded, via —O—, to a hydrocarbon group wherein a linear $C_{10-40}$ alkyl group is bonded via a single bond or —O—.

A pseudo solid phase protecting group preferable for extraction is explained now. The "branched chain" of the "organic group having at least one aliphatic hydrocarbon group having one or more branched chains and having a total carbon number of not less than 14 and not more than 300" is a linear or branched chain saturated aliphatic hydrocarbon group, and is preferably a $C_{1-6}$ alkyl group, more preferably a $C_{1-4}$ alkyl group, further preferably a methyl group or an ethyl group. The "branched chain" is optionally substituted by one or more halogen atoms.

The "aliphatic hydrocarbon group" of the "organic group having at least one aliphatic hydrocarbon group having one or more branched chains and having a total carbon number of not less than 14 and not more than 300" is a linear saturated or unsaturated aliphatic hydrocarbon group, and is a $C_{2-300}$ alkyl group (preferably $C_{3-100}$ alkyl group, more preferably $C_{3-60}$ alkyl group), a $C_{2-300}$ alkenyl group (preferably $C_{3-100}$ alkenyl group, more preferably $C_{3-60}$ alkenyl group) or a $C_2$-300 alkynyl group (preferably $C_{3-100}$ alkynyl group, more preferably $C_{3-60}$ alkynyl group).

The position of the "aliphatic hydrocarbon group having one or more branched chains" of the "organic group having at least one aliphatic hydrocarbon group having one or more branched chains and having a total carbon number of not less than 14 and not more than 300" is not particularly limited, and may be present on the terminal (monovalent group) or a position other than the terminal (e.g., divalent group).

Examples of the "aliphatic hydrocarbon group having one or more branched chains" include branched isomers of propyl group, butyl group, pentyl group, hexyl group, heptyl group, octyl group, nonyl group, decyl group, undecyl group, dodecyl group (lauryl group), tridecyl group, myristyl group, cetyl group, stearyl group, arachyl group, behenyl group, oleyl group, linolyl group, lignoceryl group and the like, and is a monovalent group having one or more branched chains and a divalent group derived therefrom. The "aliphatic hydrocarbon group having one or more branched chains" is preferably a 3,7,11-trimethyldodecyl group, a 3,7,11,15-tetramethylhexadecyl group (hereinafter sometimes to be also referred to as 2,3-dihydrophytyl group), a 2,2,4,8,10,10-hexamethylundecan-5-yl group or the like.

When the "organic group having at least one aliphatic hydrocarbon group having one or more branched chains and having a total carbon number of not less than 14 and not more than 300" contains a plurality of "aliphatic hydrocarbon groups having one or more branched chains", they may be the same or different.

The moiety other than the "aliphatic hydrocarbon group having one or more branched chains" in the "organic group having at least one aliphatic hydrocarbon group having one or more branched chains and having a total carbon number of not less than 14 and not more than 300" can be determined freely. For example, it optionally has a moiety such as —O—, —S—, —CO—, —NH—, —COO—, —OCONH—, —CONH—, —NHCO—, and a hydrocarbon group (monovalent group or divalent group) and the like. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as alkyl group, alkenyl group, alkynyl group, cycloalkyl group, aryl group, aralkyl group and the like, and divalent groups derived therefrom are used. As the "alkyl group", a $C_{1-6}$ alkyl group is preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group is preferable and, for example, vinyl, 1-propenyl, allyl, isopropenyl, butenyl, isobutenyl and the like can be mentioned. As the "alkynyl group", a $C_{2-6}$ alkynyl group is preferable and, for example, ethynyl, propargyl, 1-propynyl and the like can be mentioned. As the "cycloalkyl group", a $C_{3-6}$ cycloalkyl group is preferable and, for example, cyclopropyl, cyclobutyl, cyclopentyl, cyclohexyl can be mentioned. As the "aryl group", a $C_{6-14}$ aryl group is preferable and, for example, phenyl, 1-naphthyl, 2-naphthyl, biphenylyl, 2-anthryl and the like can be mentioned. Among these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Among these, a $C_{7-16}$ aralkyl group ($C_{6-10}$ aryl-$C_{1-6}$ alkyl group) is more preferable, and benzyl is particularly preferable. The "hydrocarbon group" is optionally substituted by a substituent selected from a halogen atom (chlorine atom, bromine atom, fluorine atom, iodine atom), an oxo group and the like.

The "total carbon number" in the "organic group having at least one aliphatic hydrocarbon group having one or more branched chains and having a total carbon number of not less than 14 and not more than 300" is not less than 14, preferably not less than 16, more preferably not less than 18, and not more than 300, preferably not more than 200, more preferably not more than 160. The number of the branched chain in the "organic group having at least one aliphatic hydrocarbon group having one or more branched chains and having a total carbon number of not less than 14 and not more than 300" is not particularly limited, and not less than 2 is preferable, not less than 3 is more preferable, not less than 4 is more preferable, not less than 8 is further preferable, not less than 10 is further more preferable. When the number of the branched chain is higher, nucleoside or oligonucleotide protected by a pseudo solid phase protecting group having an organic group having at least one aliphatic hydrocarbon group having one or more branched chains and having a total carbon number of not less than 14 and not more than 300 is dissolved well in an organic solvent (particularly, non-polar solvent) even when the oligonucleotide chain is long.

As the "organic group having at least one aliphatic hydrocarbon group having one or more branched chains and having a total carbon number of not less than 14 and not more than 300", a group having the same or different divalent group represented by the formula (A):

(A)

wherein

*is the bonding position to the adjacent atom;

$R^{14}$ and $R^{15}$ are each independently a hydrogen atom or a $C_{1-4}$ alkyl group; and $X^1$ is a single bond or a $C_{1-4}$ alkylene group, provided that $R^{14}$ and $R^{15}$ are not hydrogen atoms at the same time, is preferable.

Examples of the group having the divalent group represented by the formula (A) include a group represented by any of the following formulas (B)-(D). In the definition of each symbol in the formulas (B)-(D), the carbon number, number of repeat units ($m_1$, $n_0$-$n_2$) and the like are shown for convenience, and can be appropriately changed within the range of the above-mentioned definitions so that the total carbon number can be not less than 14 (preferably not less than 16, more preferably not less than 18) and not more than 300 (preferably not more than 200, more preferably not more than 160). The formulas (B)-(D) are explained in order below.

The formula (B) is as described below.

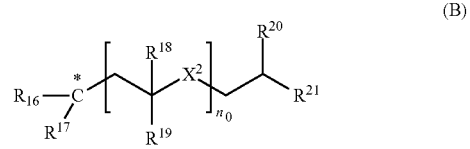

(B)

wherein

* is the bonding position to the adjacent atom;

$R^{16}$ and $R^{17}$ are hydrogen atoms or joined to show =O;

$n_0$ is an integer of 2 to 40;

$R^{18}$ and $R^{19}$ in the number of $n_0$ are each independently a hydrogen atom or a $C_{1-4}$ alkyl group;

$X^2$ in the number of $n_0$ are each independently a single bond or a $C_{1-4}$ alkylene group;

$R^{20}$ is a hydrogen atom or a $C_{1-4}$ alkyl group; and $R^{21}$ is a $C_{1-4}$ alkyl group, provided that $R^{18}$ and $R^{19}$ are not hydrogen atoms at the same time, and when $n_0$ is 2, $R^{20}$ is a $C_{1-4}$ alkyl group.

As the group of the formula (B), a group wherein $R^{16}$ and $R^{17}$ are each a hydrogen atom;

$n_0$ is an integer of 2 to 40;

$R^{18}$ and $R^{19}$ in the number of $n_0$ are each independently a hydrogen atom, a methyl group or an ethyl group;

$X^2$ in the number of $n_0$ are each independently a single bond, a methylene group or an ethylene group; and $R^{20}$ is a hydrogen atom, a methyl group or an ethyl group (provided that $R^{18}$ and $R^{19}$ are not hydrogen atoms at the same time, and when $n_0$ is 2, $R^{20}$ is methyl or an ethyl group) is preferable.

The group of the formula (B) is more preferably a branched isomer having a carbon number of 14-160 of myristyl group, cetyl group, stearyl group, arachyl group, behenyl group or the like, of which a 2,3-dihydrophytyl group, a 3,7,11-trimethyldodecyl group, and a 2,2,4,8,10,10-hexamethyl-5-dodecanoyl group are particularly preferable.

The formula (C) is as described below.

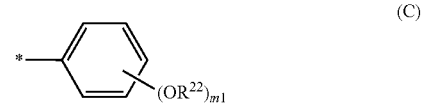

(C)

wherein

* is the bonding position to the adjacent atom;

$OR^{22}$ in the number of $m_1$ are each independently a hydroxy group substituted by a group represented by the formula (B); and $m_1$ is an integer of 1 to 3.]

The "group represented by the formula (B)" in the formula (C) is as described above except that * therein is the bonding position to O (i.e., adjacent atom).

In the group of the formula (C), $R^{22}$ is more preferably a branched isomer group having a carbon number of 14-30 of myristyl group, cetyl group, stearyl group, arachyl group, behenyl group or the like, of which a 2,3-dihydrophytyl group, a 3,7,11-trimethyldodecyl group are particularly preferable.

The formula (D) is as described below.

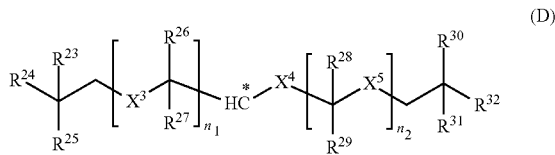

wherein
* is the bonding position to Q;
$n_1$ is an integer of 1 to 10;
$n_2$ is an integer of 1 to 10;
$R^{26}$ and $R^{27}$ in the number of $n_1$ are each independently a hydrogen atom or a $C_{1-4}$ alkyl group;
$X^3$ in the number of $n_1$ are each independently a single bond or a $C_{1-4}$ alkylene group;
$R^{28}$ and $R^{29}$ in the number of $n_2$ are each independently a hydrogen atom or a $C_{1-4}$ alkyl group;
$X^5$ in the number of $n_2$ are each independently a single bond or a $C_{1-4}$ alkylene group;
$X^4$ is a single bond or a $C_{1-4}$ alkylene group; and
$R^{23}$, $R^{24}$, $R^{25}$, $R^{30}$, $R^{31}$ and $R^{32}$ are each independently a hydrogen atom or a $C_{1-4}$ alkyl group,
provided that $R^{26}$ and $R^{27}$, and/or $R^{28}$ and $R^{29}$ are not hydrogen atoms at the same time, and when $n_1+n_2$ is 2, two or more of $R^{23}$, $R^{24}$ and $R^{25}$ are each independently a $C_{1-4}$ alkyl group, or two or more of $R^{30}$, $R^3$ and $R^{32}$ are each independently a $C_{1-4}$ alkyl group.

As the group of the formula (D), a group wherein
$n_1$ is an integer of 1 to 5;
$n_2$ is an integer of 1 to 5;
$R^2$ and $R^{27}$ in the number of $n_1$ are each independently a hydrogen atom, a methyl group or an ethyl group;
$X^3$ in the number of $n_1$ are each independently a single bond, a methylene group or an ethylene group;
$R^{28}$ and $R^{29}$ in the number of $n_2$ are each independently a hydrogen atom, a methyl group or an ethyl group;
$X^5$ in the number of $n_2$ are each independently a single bond, a methylene group or an ethylene group;
$X^4$ is a single bond, a methylene group or an ethylene group; and
$R^{23}$, $R^{24}$, $R^{25}$, $R^{30}$, $R^{31}$ and $R^{32}$ are each independently a hydrogen atom or a $C_{1-4}$ alkyl group,
provided that $R^{26}$ and $R^{27}$, and/or $R^{28}$ and $R^{29}$ are not hydrogen atoms at the same time, and when $n_1+n_2$ is 2, two or more of $R^{23}$, $R^{24}$ and $R^{25}$ are each independently a $C_{1-4}$ alkyl group, or two or more of $R^{30}$, $R^{31}$ and $R^{32}$ are each independently a $C_{1-4}$ alkyl group is more preferable.

As a particularly preferable group of the formula (D), a group wherein
$n_1$ is an integer of 1 to 5;
$n_2$ is an integer of 1 to 5;
$R^{26}$ and $R^{27}$ in the number of $n_1$ are each independently a hydrogen atom or a methyl group;
$X^3$ in the number of $n_1$ are each independently a single bond or a methylene group;
$R^{28}$ and $R^{29}$ in the number of $n_2$ are each independently a hydrogen atom or a methyl group;
$X^5$ in the number of $n_2$ are each independently a single bond or a methylene group;
$X^4$ is a single bond or a methylene group; and $R^{23}$, $R^{24}$, $R^{25}$, $R^{30}$, $R^{31}$ and $R^{32}$ are methyl groups, provided that $R^{26}$ and $R^{27}$, and/or $R^{28}$ and $R^{29}$ are not hydrogen atoms at the same time can be mentioned.

Specific examples of the "organic group having at least one aliphatic hydrocarbon group having one or more branched chains and having a total carbon number of not less than 14 and not more than 300" include the following groups. In each group, * shows a bonding position; in the formula, $n_3$ is an integer of not less than 3; and $n_4$ is appropriately determined such that the total carbon number of the groups is not less than 14 and not more than 300.

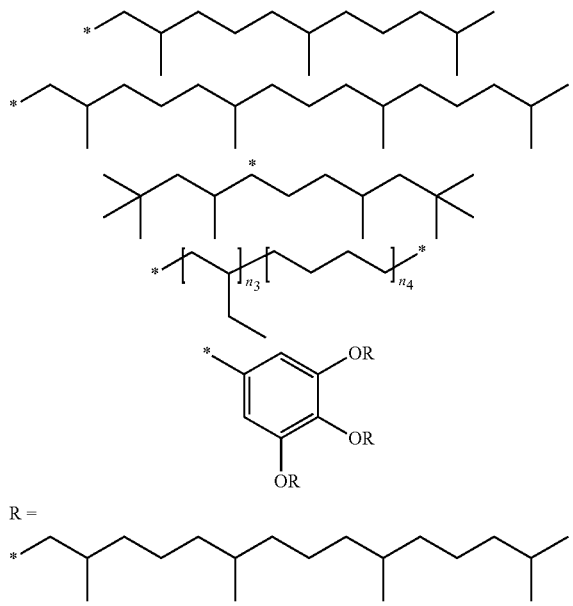

Specific preferable examples of the "organic group having at least one aliphatic hydrocarbon group having one or more branched chains and having a total carbon number of not less than 14 and not more than 300" include the following groups:
3,7,11,15-tetramethylhexadecyl group (alias: 2,3-dihydrophytyl group);
3,7,11-trimethyldodecyl group;
2,2,4,8,10,10-hexamethyl-5-dodecanoyl group;
3,4,5-tri(3',7',11',15'-tetramethylhexadecyloxy)benzyl group; and
3,5-di(3',7',11',15'-tetramethylhexadecyloxy)benzyl group.

The pseudo solid phase protecting group is more preferably a group represented by the following formula (g-I) (hereinafter sometimes to be abbreviated as "pseudo solid phase protecting group (g-I)").

$$**L-Y-Z \qquad \text{(g-I)}$$

wherein
** is the bonding position to the protected group;
L is a single bond, or a group represented by the formula (a1) or (a1'):

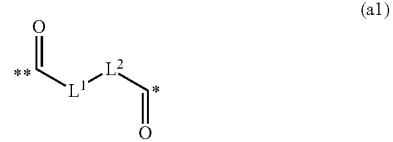

-continued

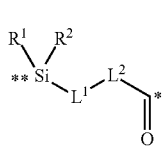
(a1')

wherein
* is the bonding position to Y;
* is as defined above;
$R^1$ and $R^2$ are each independently a $C_{1-22}$ hydrocarbon group;
$L^P$ is an optionally substituted divalent $C_{1-22}$ hydrocarbon group;
$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
Y is a single bond, an oxygen atom or NR (wherein R is a hydrogen atom, an alkyl group or an aralkyl group); and
Z is a group represented by the formula (a2), the formula (a2') or the formula (a2"):

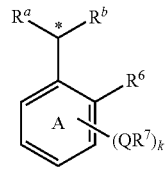
(a2)

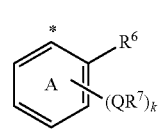
(a2')

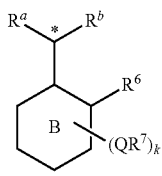
(a2")

wherein
* indicates a bonding position;
$R^6$ is a hydrogen atom, or when $R^b$ is a group represented by the following formula (a3), $R^6$ of ring A or ring B is optionally shows, together with $R^8$, a single bond or —O— to form, together with ring A or ring B and ring C, a fused ring;
k is an integer of 1 to 4;
Q in the number of k are each independently —O—, —C(=O)—, —C(=O)O—, —OC(=O)—, —C(=O)NH— or —NHC(=O)—;
$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
ring A and ring B, each independently, optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom; and
$R^b$ is a hydrogen atom, or a group represented by the formula (a3):

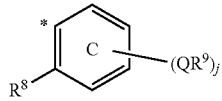
(a3)

wherein
* indicates a bonding position;
j is an integer of 0 to 4;
Q in the number of j are each independently as defined above;
$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
$R^8$ is a hydrogen atom, or optionally shows, together with $R^6$ of ring A or ring B, a single bond or —O— to form, together with ring A or ring B and ring C, a fused ring; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group.

The linear aliphatic hydrocarbon groups having a carbon number of not less than 10, that $R^7$ in the formula (a2), the formula (a2') and the formula (a2"), and $R^9$ in the formula (a3) have, are each independently preferably selected from linear $C_{10-40}$ alkyl group and linear $C_{10-40}$ alkenyl group, more preferably linear $C_{10-40}$ alkyl group, further preferably linear $C_{0-30}$ alkyl group, particularly preferably linear $C_{12-28}$ alkyl group, most preferably linear $C_{14-26}$ alkyl group.

The linkers that $R^7$ in the formula (a2), the formula (a2') and the formula (a2"), and $R^9$ in the formula (a3) have are each independently preferably —O—, —C(=O)—, —C(=O)O—, —OC(=O)—, —C(=O)NH— or —NHC(=O)—, more preferably —O—.

The "hydrocarbon group wherein a linear aliphatic hydrocarbon group having a carbon number of not less than 10 is bonded via a single bond or a linker" for $R^7$ in the formula (a2), the formula (a2') and the formula (a2"), and $R^9$ in the formula (a3) is preferably a linear $C_{10-40}$ alkyl group, a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—.

The "organic groups having at least one aliphatic hydrocarbon groups having one or more branched chains and having a total carbon number of not less than 14 and not more than 300", each which is one embodiment of $R^7$ in the formula (a2), the formula (a2') and the formula (a2"), and $R^9$ in the formula (a3), are each independently preferably a group having a divalent group represented by the above-mentioned formula (A), more preferably a group represented by any of the above-mentioned formulas (B)-(D), further preferably a group represented by the above-mentioned formula (B), particularly preferably a 2,3-dihydrophytyl group, a 3,7,11-trimethyldodecyl group, or a 2,2,4,8,10,10-hexamethyl-5-dodecanoyl group.

Q in the formula (a2), the formula (a2'), the formula (a2") and the formula (a3) is preferably —O—, —C(=O)NH— or —NHC(=O)—, more preferably —O—.

In the formula (g-I), a preferred embodiment of L represented by the formula (a1) is a group wherein
 $L^1$ is a divalent $C_{1-22}$ hydrocarbon group or $CH_2$—O-1, 4-phenylene-O—$CH_2$; and
 $L^2$ is a single bond or a group represented by *C(=O)N($R^3$)—$R^4$—N($R^5$) wherein * is the bonding position to $L^1$, **** is the bonding position to C=O, $R^4$ is a $C_{1-6}$ alkylene group, $R^3$ and $R^5$ are each independently a hydrogen atom or an optionally substituted $C_{1-6}$ alkyl group, or $R^3$ and $R^5$ are optionally joined to form an optionally substituted $C_{1-6}$ alkylene group.

Another preferred embodiment of L represented by the formula (a1) is a group wherein
 $L^1$ is a divalent $C_{1-22}$ hydrocarbon group; and
 $L^2$ is a single bond.

Another preferred embodiment of L represented by the formula (a1) is a group wherein
 $L^1$ is an ethylene group; and
 $L^2$ is a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring.

Another preferred embodiment of L represented by the formula (a1) is a group wherein
 $L^1$ is an ethylene group; and
 $L^2$ is a group represented by *C(=O)N($R^3$)—$R^4$—N($R^5$) wherein * is the bonding position to $L^1$, **** is the bonding position to C=O, and N($R^3$)—$R^4$—N($R^5$) moiety forms a 1,4-piperazinediyl group.

Another preferred embodiment of L represented by the formula (a1) is a group wherein
 $L^1$ is an ethylene group; and
 $L^2$ is a group represented by *C(=O)N($R^3$)—R—N($R^5$) wherein * is the bonding position to $L^1$, **** is the bonding position to C=O, $R^4$ is a pentylene group or a hexylene group, and $R^3$ and $R^5$ are each independently a hydrogen atom or a methyl group.

Particularly preferred embodiment of L represented by the formula (a1) is a succinyl group which is easily available and economical.

In the formula (g-I), L represented by the formula (a1') is explained below.
 $L^1$ in the formula (a1') is preferably a divalent $C_{6-10}$ aromatic hydrocarbon group, more preferably a phenylene group.
 $L^2$ in the formula (a1') is preferably a single bond.

A preferable combination of $L^1$ and $L^2$ in the formula (a1') is a combination of a divalent $C_{6-10}$ aromatic hydrocarbon group for $L^1$ and a single bond for $L^2$. A more preferable combination of $L^1$ and $L^2$ in the formula (a1') is a combination of a phenylene group for $L^1$ and a single bond for $L^2$.

$R^1$ and $R^2$ in the formula (a1') are each independently preferably a $C_{1-22}$ alkyl group, more preferably a $C_{1-10}$ alkyl group.

A preferred embodiment of L represented by the formula (a1') is a group wherein
 $R^1$ and $R^2$ are each independently a $C_{1-22}$ alkyl group;
 $L^1$ is a divalent $C_{6-10}$ aromatic hydrocarbon group; and
 $L^2$ is a single bond.

Another preferred embodiment of L represented by the formula (a1') is a group wherein
 $R^1$ and $R^2$ is are each independently a $C_{1-10}$ alkyl group;
 $L^1$ is a phenylene group; and
 $L^2$ is a single bond.

When Y in the formula (g-I) is NR, the aforementioned R is preferably a hydrogen atom, a $C_{1-6}$ alkyl group or a $C_{7-16}$ aralkyl group, more preferably a hydrogen atom, methyl, ethyl or benzyl, further preferably a hydrogen atom. Y is preferably a single bond, an oxygen atom or NR, more preferably a single bond or an oxygen atom.

Z in the formula (g-I) is preferably a group represented by the formula (a2) or the formula (a2"), more preferably a group represented by the formula (a2"). Using a pseudo solid phase protecting group having Z represented by the formula (a2") (i.e., structure of cyclohexylmethyl group), the solubility of the nucleoside, nucleotide or oligonucleotide (a) and the like in non-polar solvents can be strikingly improved as compared with a pseudo solid phase protecting group having Z represented by the formula (a2) (i.e., structure of benzyl group). As a result, the production method of the present invention can be performed at a higher concentration and productivity is strikingly improved.

In the formula (a2), $R^6$ is preferably a hydrogen atom. In the formula (a2), $R^a$ and $R^b$ are each preferably a hydrogen atom, or are joined to form an oxo group.

An embodiment preferable for solid-liquid separation of Z represented by the formula (a2) is a group wherein
 $R^a$ and $R^b$ are hydrogen atoms;
 $R^6$ is a hydrogen atom;
 k is an integer of 1 to 3;
 Q in the number of k are —O—; and
 $R^7$ in the number of k are each independently a linear $C_{10-40}$ alkyl group.

Another embodiment preferable for solid-liquid separation of Z represented by the formula (a2) is a group wherein
 $R^a$ and $R^b$ are hydrogen atoms;
 $R^6$ is a hydrogen atom;
 k is an integer of 1 to 3;
 Q in the number of k are —O—; and
 $R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
 ring A optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Another embodiment preferable for solid-liquid separation of Z represented by the formula (a2) is a group wherein
 $R^a$ is a hydrogen atom; and
 $R^b$ is a group represented by the formula (a3) wherein * shows the bonding position, j is an integer of 0 to 3, Q in the number of j are —O—, $R^9$ in the number of j are each independently a linear $CO_{10-40}$ alkyl group, $R^6$ and $R^8$ are each a hydrogen atom.

Another embodiment preferable for solid-liquid separation of Z represented by the formula (a2) is a group wherein
$R^a$ is a hydrogen atom; and
$R^b$ is a group represented by the formula (a3) wherein * shows the bonding position, j is an integer of 0 to 3, Q in the number of j are —O—, $R^9$ in the number of j are each independently a linear $C_{10-40}$ alkyl group, $R^8$ shows, together with $R^6$, a single bond or —O— to form, together with ring A and ring C, a fused ring.

Another embodiment preferable for solid-liquid separation of Z represented by the formula (a2) is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a linear $C_{10}$-40 alkyl group.

Another embodiment preferable for solid-liquid separation of Z represented by the formula (a2) is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring A optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

In the formula (a2"), $R^6$ is preferably a hydrogen atom. In the formula (a2"), $R^a$ and $R^b$ are each preferably a hydrogen atom, or are joined to form an oxo group.

A embodiment preferable for solid-liquid separation of Z represented by the formula (a2") is a group wherein
$R^a$ and $R^b$ are hydrogen atoms;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2") is a group wherein
$R^a$ and $R^b$ is a hydrogen atom;
$R^6$ is a hydrogen atom;
k is an integer of 1 to 3;
Q in the number of k are —O—;
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Another embodiment preferable for solid-liquid separation of Z represented by the formula (a2") is a group wherein
$R^a$ is a hydrogen atom;
$R^b$ is a group represented by the formula (a3) wherein * shows the bonding position, j is an integer of 0 to 3, Q in the so number of j are —O—, $R^9$ in the number of j are each independently a $C_{10-40}$ alkyl group, and $R^6$ and $R^8$ are hydrogen atoms.

Another embodiment preferable for solid-liquid separation of Z represented by the formula (a2") is a group wherein
$R^a$ is a hydrogen atom;
$R^b$ is a group represented by the formula (a3) wherein * shows the bonding position, j is an integer of 0 to 3, Q in the number of j is —O—, $R^9$ in the number of j are each independently a linear $C_{10-40}$ alkyl group, $R^8$ shows, together with $R^6$, a single bond or —O— to form, together with ring B and ring C, a fused ring.

Another embodiment preferable for solid-liquid separation of Z represented by the formula (a2") is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2") is a group wherein
$R^a$ and $R^b$ are joined to form an oxo group;
$R^6$ is a hydrogen atom;
k is an integer of 1 to 3;
Q in the number of k are —O—;
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

The pseudo solid phase protecting group (g-I) preferable for solid-liquid separation is preferably a group wherein
L is a succinyl group, or a group represented by the formula (a1') (in the formula (a1'), $R^1$ and $R^2$ are each independently a $C_{1-10}$ alkyl group, $L^1$ is a divalent phenylene group, $L^2$ is a single bond), and
Y—Z is a 3,4,5-tris(octadecyloxy)benzyloxy group, a 3,5-bis(docosyloxy)benzyloxy group, a 3,5-bis[3',4',5'-tris(octadecyloxy)benzyloxy]benzyloxy group, a 3,4,5-tris[3',4',5'-tris(octadecyloxy)benzyloxy]benzyloxy group, a 3,4,5-tris(octadecyloxy)benzylamino group, a 2,4-bis(docosyloxy)benzylamino group, 3,5-bis(docosyloxy)benzylamino group, a bis(4-docosyloxyphenyl)methylamino group, a 4-methoxy-2-[3',4',5'-tris(octadecyloxy)benzyloxy]benzylamino group, a 4-methoxy-2-[3',4',5'-tris(octadecyloxy)cyclohexylmethyloxy] benzylamino group, a 2,4-bis(dodecyloxy) benzylamino group, a phenyl(2,3,4-tris(octadecyloxy)phenyl)methylamino group, a bis[4-(12-docosyloxydodecyloxy)phenyl]methylamino group, a 3,5-bis[3',4',5'-tris(octadecyloxy)benzyloxy]benzylamino group, a 3,4,5-tris[3',4',5'-tris(octadecyloxy)benzyloxy]benzylamino group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy] cyclohexylmethyloxy group, a 3,4,5-tris[3',4',5'-tris (octadecyloxy)cyclohexylmethyloxy] cyclohexylmethyloxy group, a 3,4,5-tris(octadecyloxy) cyclohexylmethylamino group, a 2,4-bis(docosyloxy) cyclohexylmethylamino group, a 3,5-bis(docosyloxy) cyclohexylmethylamino group, a bis(4- docosyloxycyclohexyl)methylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, phenyl(2,3,4-tris(octadecyloxy)cyclohexyl)methylamino group, a bis[4-(12-docosyloxydodecyloxy)cyclohexyl]methylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein L-Y is a single bond or a succinyl-1,4-piperazinediyl group, and Z is a 3,4,5-tris(octadecyloxy)benzoyl group, a 3,5-bis(docosyloxy)benzoyl group, a 3,5-bis[3',4',5'-tris(octadecyloxy)benzyloxy]benzoyl group or a 3,4,5-tris[3',4',5'-tris(octadecyloxy)benzyloxy]benzoyl group.

The pseudo solid phase protecting group (g-I) preferable for solid-liquid separation is more preferably a group wherein L is a succinyl group, and Y—Z is a 3,4,5-tris(octadecyloxy)benzyloxy group, a 3,5-bis(docosyloxy)benzyloxy group, a 3,5-bis[3',4',5'-tris(octadecyloxy)benzyloxy]benzyloxy group, a 3,4,5-tris[3',4',5'-tris(octadecyloxy)benzyloxy]benzyloxy group, a 3,4,5-tris(octadecyloxy)benzylamino group, a 2,4-bis(docosyloxy)benzylamino group, a 3,5-bis(docosyloxy)benzylamino group, a bis(4-docosyloxyphenyl)methylamino group, a 4-methoxy-2-[3',4',5'-tris(octadecyloxy)benzyloxy]benzylamino group, a 4-methoxy-2-[3',4',5'-tris(octadecyloxy)cyclohexylmethyloxy]benzylamino group, a 2,4-bis(dodecyloxy)benzylamino group, a phenyl(2,3,4-tris(octadecyloxy)phenyl)methylamino group, a bis[4-(12-docosyloxydodecyloxy)phenyl]methylamino group, a 3,5-bis[3',4',5'-tris(octadecyloxy)benzyloxy]benzylamino group, a 3,4,5-tris[3'4',45'-tris(octadecyloxy)benzyloxy]benzylamino group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy]cyclohexylmethyloxy group, a 3,4,5-tris[3',4',5'-tris(octadecyloxy)cyclohexylmethyloxy]cyclohexylmethyloxy group, a 3,4,5-tris(octadecyloxy)cyclohexylmethylamino group, a 2,4-bis(docosyloxy)cyclohexylmethylamino group, a 3,5-bis(docosyloxy)cyclohexylmethylamino group, a bis(4-docosyloxycyclohexyl)methylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, phenyl(2,3,4-tris(octadecyloxy)cyclohexyl)methylamino group, a bis[4-(12-docosyloxydodecyloxy)cyclohexyl]methylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein L-Y is a single bond or a succinyl-1,4-piperazinediyl group, and Z is a 3,4,5-tris(octadecyloxy)benzoyl group, a 3,5-bis(docosyloxy)benzoyl group, a 3,5-bis[3',4',5'-tris(octadecyloxy)benzyloxy]benzoyl group or a 3,4,5-tris[3',4',5'-tris(octadecyloxy)benzyloxy]benzoyl group.

The pseudo solid phase protecting group (g-I) preferable for solid-liquid separation is further preferably a group wherein L is a succinyl group, and Y—Z is a 3,4,5-tris(octadecyloxy)benzyloxy group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy]cyclohexylmethyloxy group, a 3,4,5-tris[3',4',5'-tris(octadecyloxy)cyclohexylmethyloxy]cyclohexylmethyloxy group, a 3,4,5-tris(octadecyloxy)cyclohexylmethylamino group, a 2,4-bis(docosyloxy)cyclohexylmethylamino group, a 3,5-bis(docosyloxy)cyclohexylmethylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein L-Y is a single bond or a succinyl-1,4-piperazinediyl group, and Z is a 3,4,5-tris(octadecyloxy)benzoyl group.

The pseudo solid phase protecting group (g-I) preferable for solid-liquid separation is particularly preferably a group wherein L is a succinyl group, and Y—Z is a 3,4,5-tris(octadecyloxy)benzyloxy group, a 3,4,5-tris(octadecyloxy)cyclohexylmethyloxy group or a phenyl(2,3,4-tris(octadecyloxy)phenyl)methylamino group, or a group wherein L-Y is a succinyl-1,4-piperazinediyl group, and Z is a 3,4,5-tris(octadecyloxy)benzoyl group.

The pseudo solid phase protecting group (g-I) preferable for solid-liquid separation is most preferably a group wherein L is a succinyl group, and Y—Z is a 3,4,5-tris(octadecyloxy)benzyloxy group or a 3,4,5-tris(octadecyloxy)cyclohexylmethyloxy group, or a group wherein L-Y is a succinyl-1,4-piperazinediyl group, and Z is a 3,4,5-tris(octadecyloxy)benzoyl group.

The pseudo solid phase protecting group (g-I) preferable for extraction is preferably a 2-{2,4-di(2',3'-dihydrophytyloxy)benzylaminocarbonyl}ethylcarbonyl group; a 3,5-di(2',3'-dihydrophytyloxy)benzyloxysuccinyl group; a 4-(2',3'-dihydrophytyloxy)benzyloxysuccinyl group; a 2-{1-[(2-chloro-5-(2',3'-dihydrophytyloxy)phenyl)]benzylaminocarbonyl}ethylcarbonyl group; a 3,4,5-tri(2',3'-dihydrophytyloxy)benzyloxysuccinyl group; a 2-{3,4,5-tri(2',3'-dihydrophytyloxy)benzylaminocarbonyl}ethylcarbonyl group; a 2-{4-(2',3'-dihydrophytyloxy)benzylaminocarbonyl}ethylcarbonyl group; a 2-{2-[3',4',5'-tri(2",3"-dihydrophytyloxy)benzyloxy]-4-methoxybenzylaminocarbonyl}ethylcarbonyl group; a 2-{4-(2',3'-dihydrophytyloxy)-2-methoxybenzylaminocarbonyl}ethylcarbonyl group; a 4-(2',3'-dihydrophytyloxy)-2-methylbenzyloxysuccinyl group; a 2-{4-(2',3'-dihydrophytyloxy)-2-methylbenzylaminocarbonyl}ethylcarbonyl group; a 4-[2,2, 4,8,10,10-hexamethyl-5-dodecanoylamino]benzyloxysuccinyl group; a 2-{4-[2,2,4,8,10,10-hexamethyl-5-dodecanoylamino]benzylaminocarbonyl}ethylcarbonyl group; a 4-(3,7,11-trimethyldodecyloxy)benzyloxysuccinyl group; a 2-{4-(3,7,11-trimethyldodecyloxy)benzylaminocarbonyl}ethylcarbonyl group; a 2-{3,5-di(2',3'-dihydrophytyloxy)benzylaminocarbonyl}ethylcarbonyl group; a 2-{1-[2,3,4-tri(2',3'-dihydrophytyloxy)phenyl]benzylaminocarbonyl}ethylcarbonyl group; a 2-{1-[4-(2',3'-dihydrophytyloxy)phenyl]-4'-(2',3'-dihydrophytyloxy)benzylaminocarbonyl}ethylcarbonyl group; a 3,4,5-tris[3,4,5-tri(2',3'-dihydrophytyloxy)benzyl]benzyloxysuccinyl group; or a 2-{3,4,5-tris[3,4,5-tri (2',3'-dihydrophytyloxy)benzyl]benzylaminocarbonyl}ethylcarbonyl group.

An alcohol compound or amine compound represented by the formula: Z—Y—H and used for forming a pseudo solid phase protecting group can be produced by, for example, the steps described in paragraphs [0186] to [0221] of WO 2017/104836, which is incorporated herein by reference in its entirety, or a step analogous thereto.

Examples of the nucleoside, nucleotide or oligonucleotide (a) used in this step include a compound represented by the following formula (a-I) (i.e., nucleoside or oligonucleotide).

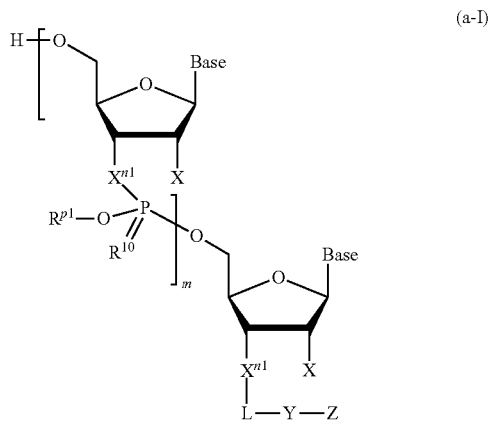

(a-I)

wherein
m is an integer of not less than 0;
Base in the number of m+1 are each independently optionally protected nucleic acid base;
X in the number of m+1 are each independently a hydrogen atom, a halogen atom, an optionally protected hydroxy group, or a divalent organic group bonded to 2-position carbon atom and 4-position carbon atom;
$X^{n1}$ in the number of m+1 are each independently an oxygen atom or NH;
$R^{10}$ in the number of m are each independently an oxygen atom or a sulfur atom;
$R^{p1}$ in the number of m are each independently is a protecting group of phosphate group;
L, Y and Z are as defined above.

In the following, a compound represented by the formula (a-I) is sometimes to be abbreviated as "compound (a-I)". Also, compounds represented by other formulas are sometimes abbreviated similarly.

The amino group of the nucleic acid base is preferably protected by a protecting group. As the protecting group, acetyl group, phenoxyacetyl group, 4-isopropylphenoxyacetyl group, benzoyl group, isobutyryl group, (2-hexyl)decanoyl group, dimethylformamidinyl group, and =NC($R^{11}$)—N($R^{12}$) ($R^{13}$) group wherein $R^{11}$ is a methyl group, $R^{12}$ and $R^{13}$ are each independently a $C_{1-5}$ alkyl group, or $R^1$ and $R^2$ are optionally joined to form, together with the carbon atom and nitrogen atom bonded thereto, a 5-membered or 6-membered nitrogen-containing hydrocarbocycle are preferable. Examples of the aforementioned =NC($R^{11}$)—N($R^{12}$) ($R^{13}$) group include a 1-(dimethylamino)ethylidene group. When compound (a-I) has plural amino groups, only one kind or two or more kinds of the amino-protecting group may be used.

When m is 0, compound (a-I) is a nucleoside, and when m is one or more, compound (a-I) is an oligonucleotide. m is preferably not more than 49, more preferably not more than 29, further preferably not more than 19, particularly preferably not more than 4, and most preferably not more than 2.

As the halogen atom for X, a fluorine atom or a chlorine atom is preferable, and a fluorine atom is more preferable.

The protecting group of the optionally protected hydroxy group for X is not particularly limited and, for example, any protecting group described in PROTECTIVE GROUPS IN ORGANIC SYNTHESIS, 3rd ed., JOHN WILLY&SONS (1999), which is incorporated herein by reference in its entirety, and the like can be mentioned. Specifically, methyl group, benzyl group, p-methoxybenzyl group, tert-butyl group, methoxymethyl group, methoxyethyl group, 2-tetrahydropyranyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, trimethylsilyl group, triethylsilyl group, triisopropylsilyl group, tert-butyldimethylsilyl group, [(triisopropylsilyl)oxy]methyl (Tom) group, 1-(4-chlorophenyl)-4-ethoxypiperidin-4-yl (Cpep) group and the like can be mentioned. The protecting group of the optionally protected hydroxy group is preferably a triethylsilyl group, a triisopropylsilyl group or a tert-butyldimethylsilyl group, particularly preferably a tert-butyldimethylsilyl group, from the aspects of economic efficiency and easy availability.

The "divalent organic group bonded to 2-position carbon atom and 4-position carbon atom" for X is not particularly limited as long as it is bonded to 2-position carbon atom and 4-position carbon atom of nucleoside. Examples of the divalent organic group include an optionally substituted $C_{2-7}$ alkylene group, and a divalent organic group constituted of an optionally substituted $C_{1-7}$ alkylene group and a divalent linker selected from —O—, —$NR^{33}$—($R^{33}$ is a hydrogen atom or a $C_{1-6}$ alkyl group), —S—, —CO—, —COO—, —$OCONR^{34}$—($R^{34}$ is a hydrogen atom or a $C_{1-6}$ alkyl group) and —$CONR^{35}$—($R^{35}$ is a hydrogen atom or a $C_{1-6}$ alkyl group), and the like. Examples of the substituent that the $C_{1-7}$ alkylene group and $C_{2-7}$ alkylene group optionally have include a methylidene group ($CH_2$=).

As the "divalent organic group bonded to 2-position carbon atom and 4-position carbon atom", an optionally substituted $C_{2-7}$ alkylene group, —$OR^i$— ($R^i$ is a $C_{1-6}$ alkylene group bonded to 4-position carbon atom), —O—$NR^{33}$—$R^j$—($R^j$ is a $C_{1-6}$ alkylene group bonded to 4-position carbon atom, $R^{33}$ is as defined above), —O—$R^k$—O—$R^l$—($R^k$ is a $C_{1-6}$ alkylene group, $R^l$ is a $C_{1-6}$ alkylene group bonded to and crosslinked with 4-position carbon atom) are preferable, —$OR^i$—($R^i$ is as defined above), —O—$NR^{33}$—$R^j$—($R^j$ and $R^{33}$ are as defined above), —O—$R^k$—O—$R^l$—($R^k$ and $R^l$ are as defined above) are more preferable. $C_{1-6}$ alkylene groups for $R^i$, $R^j$, $R^k$ and $R^l$ are preferably each independently a methylene group or an ethylene group.

As the "divalent organic group bonded to 2-position carbon atom and 4-position carbon atom", —O—CH$_2$—, —O—CH$_2$—CH$_2$—, —O—NR$^{33}$—CH$_2$—(R$^{33}$ is as defined above), —O—CH$_2$—O—CH$_2$— are more preferable, —O—CH$_2$—, —O—CH$_2$—CH$_2$—, —O—NH—CH$_2$—, —O—N(CH$_3$)—CH$_2$—, —O—CH$_2$—O—CH$_2$— (in each of which the left side is bonded to 2-position carbon atom and the right side is bonded to 4-position carbon atom) are further preferable.

X in the number of m+1 are each independently preferably a hydrogen atom, a halogen atom or an optionally protected hydroxy group, more preferably a hydrogen atom or an optionally protected hydroxy group.

The protecting group of phosphate group for $R^{p1}$ is not particularly limited as long as it is removable under basic conditions and can be used as a protecting group of phosphate group. A group represented by —CH$_2$CH$_2$WG (WG is an electron-withdrawing group) is preferable.

Examples of the electron-withdrawing group for WG include cyano group, nitro group and the like, preferably cyano group.

$R^{p1}$ in the number of m are preferably each independently a group represented by —CH$_2$CH$_2$WG.

$X^{n1}$ in the number of m+1 are preferably oxygen atoms.

Explanations of L, Y and Z are as mentioned above.

Compound (a-I) is preferably a compound represented by the following formula (a-i) (definition and explanation of symbols in the following formula are as mentioned above).

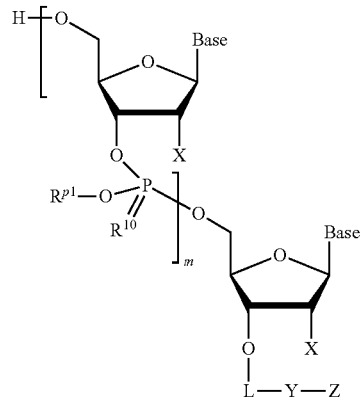

(a-i)

Compound (a-I) can be produced by a method known per se or a method analogous thereto. For example, compound (a-I) wherein m is 0, $X^{n1}$ is an oxygen atom, L is a succinyl group can be produced by, for example, as in the following formulas, first reacting nucleoside (i) having 5'-hydroxy group protected by a temporary protecting group Q" and succinic anhydride in the presence of a base to synthesize nucleoside (ii), then condensing the obtained nucleoside (ii) and compound Z—Y—H in the presence of a condensing agent to synthesize nucleoside having protected 3'- and 5'-hydroxy groups, and removing the temporary protecting group Q" with an acid.

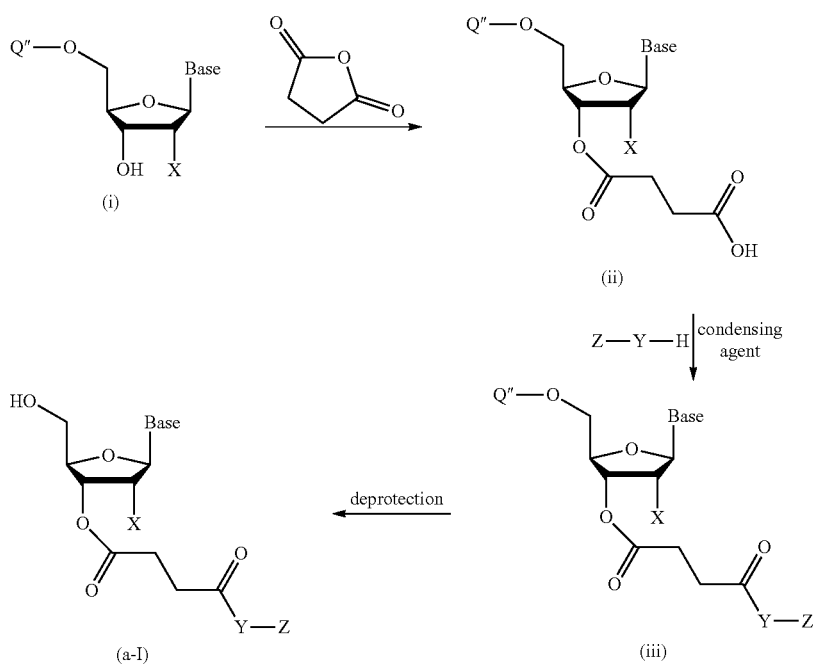

The conversion reaction from nucleoside (i) to nucleoside (ii) is advantageously performed in a solvent inert to the reaction. Such solvent is not particularly limited as long as the reaction proceeds, and halogenated solvents such as dichloromethane, 1,2-dichloroethane, chloroform, carbon tetrachloride and the like, aromatic solvents such as benzene, toluene, xylene and the like, or aliphatic solvents such as pentane, hexane, heptane, octane and the like, or ether solvents such as diethyl ether, tetrahydrofuran, cyclopentyl methyl ether and the like, and mixed solvents thereof are preferable. Of these, dichloromethane or chloroform is particularly preferable.

While the base to be used for the synthesis of nucleoside (ii) is not particularly limited, an organic base is preferable, and triethylamine is more preferable.

The condensation reaction for synthesizing nucleoside (iii) is advantageously performed in a solvent inert to the reaction. Such solvent is not particularly limited as long as the reaction proceeds, and halogenated solvents such as dichloromethane, 1,2-dichloroethane, chloroform, carbon tetrachloride and the like, aromatic solvents such as benzene, toluene, xylene and the like, aliphatic solvents such as pentane, hexane, heptane, octane and the like, and these combination are preferable. Of these, dichloromethane and chloroform are particularly preferable.

As the condensing agent to be used for the condensation reaction of nucleoside (ii) and Z—Y—H, dicyclohexylcarbodiimide (DCC), diisopropylcarbodiimide (DIC), N-ethyl-N'-3-dimethylaminopropylcarbodiimide and hydrochloride thereof (EDC. HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like can be mentioned. Of these, HBTU, HCTU, N-ethyl-N'-3-dimethylaminopropylcarbodiimide and hydrochloride thereof (EDC. HCl) are preferable.

The amount of the condensing agent to be used is, for example, 1 to 10 mol, preferably 1 to 5 mol, per 1 mol of nucleoside (ii). The amount of Z—Y—H to be used is, for example, 1 to 10 mol, preferably 1 to 5 mol, per 1 mol of nucleoside (ii). The reaction temperature is not particularly limited as long as the reaction proceeds, and −10° C. to 50° C. is preferable, 0° C. to 30° C. is more preferable. The reaction time is, for example, 30 min to 70 hr.

Removal of the temporary protecting group Q from nucleoside (iii) (deprotection) can be performed in the same manner as in step (4) of the present invention.

Compound (a-I) wherein L is other than a succinyl group can also be synthesized by performing a similar reaction by using the corresponding acid anhydride, corresponding dicarboxylic acid halide, active ester of the corresponding dicarboxylic acid or the like instead of succinic anhydride in the above-mentioned synthesis method. Compound (a-I) wherein $X^{n1}$ is NH can also be synthesized by performing a similar reaction by using nucleoside wherein a 3'-hydroxy group is an amino group instead of nucleoside (i) in the above-mentioned synthesis method. Compound (a-I) wherein m is one or more can be synthesized by repeating a 5'-terminal elongation process by using compound (a-I) wherein m is 0 as a starting material.

Among compounds (a-i), a compound represented by the formula (a-II) (i.e., nucleoside or oligonucleotide) is preferable.

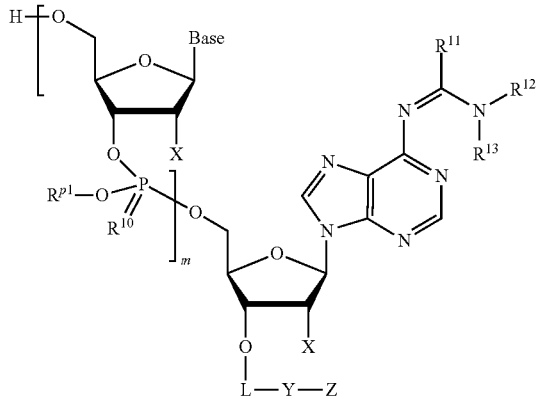

(a-II)

wherein
m, Base in the number of m, X in the number of m+1, $R^{10}$ in the number of m, $R^{p1}$ in the number of m, L, Y and Z are each independently as defined above;
$R^{11}$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbocycle.

In the formula (a-II), preferably, $R^{p1}$ in the number of m are each independently a group represented by —CH₂CH₂WG.

In the formula (a-II), m is preferably 0. That is, of compounds (a-II), a compound represented by the formula (a-III) (i.e., nucleoside) is preferable (definition and explanation of the symbols in the following formula are as mentioned above).

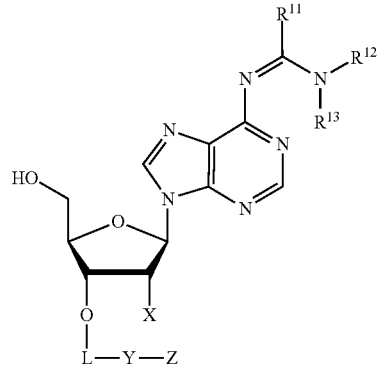

(a-III)

In the formula (a-II) and the formula (a-III), $R^{11}$ is preferably a methyl group and $R^{12}$ and $R^{13}$ are preferably each independently a $C_{1-5}$ alkyl group, and $R^{11}$, $R^{12}$ and $R^{13}$ are more preferably methyl groups.

Explanations of other symbols in the formula (a-II) and the formula (a-III) are as mentioned above.

In the present invention, when oligonucleotide wherein the first residue has adenine as a nucleic acid base is produced, production of a branched product and the like can be suppressed by using compound (a-II) (particularly, compound (a-III)) as a nucleoside, nucleotide or oligonucleotide (a) which is a starting material. As used herein, the branched product refers to a byproduct produced when an amino-protecting group of the nucleic acid base of the object compound is detached and the amino group and a monomer are bonded.

In compounds (a-i), a compound represented by the formula (a-IV) (i.e., nucleoside or oligonucleotide) is preferable.

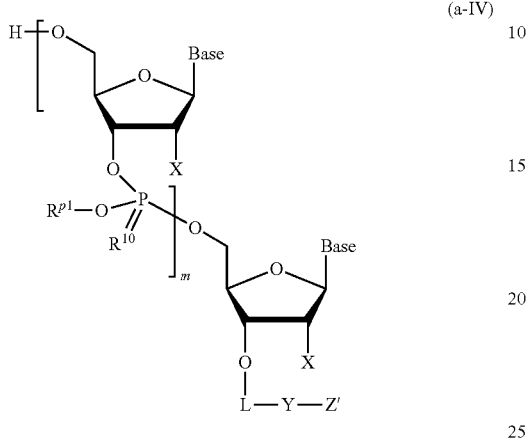

(a-IV)

wherein
m, Base in the number of m+1, X in the number of m+1, $R^{10}$ in the number of m, $R^{p1}$ in the number of m, L and Y are each independently as defined above;
Z' is a group represented by the formula (a2"):

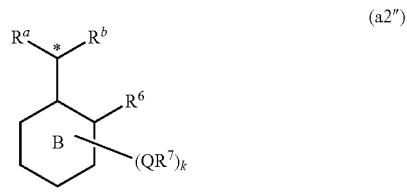

(a2")

wherein
* indicates a bonding position;
$R^6$ is a hydrogen atom or when $R^b$ is a group represented by the following formula (a3), it optionally shows, together with $R^8$, a single bond or —O— to form, together with ring B and ring C, a fused ring;
k is an integer of 1 to 4;
Q in the number of k are each independently —O—, —C(=O)—, —C(=O)O—, —OC(=O)—, —C(=O)NH— or —NHC(=O)—;
$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom; and
$R^b$ is a hydrogen atom, or a group represented by the formula (a3):

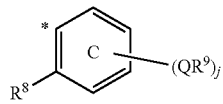

(a3)

wherein * indicates a bonding position;
j is an integer of 0 to 4;
Q in the number of j are each independently as defined above;
$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
$R^8$ is a hydrogen atom, or optionally shows, together with $R^6$, a single bond or —O— to form a fused ring with ring B and ring C; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or $R^a$ and $R^b$ are joined to form an oxo group.
In the formula (a-IV), $R^{p1}$ in the number of m are preferably each independently a group represented by —CH$_2$CH$_2$WG.
In the formula (a-IV), m is preferably 0.
Explanations of other symbols in the formula (a-IV) are as mentioned above.

In compounds (a-IV), a compound represented by the following formula (a-V) (i.e., nucleoside) is preferable (definition and explanation of the symbols in the following formula are as mentioned above).

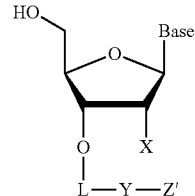

(a-V)

In compounds (a-I), compound (a-IV) (particularly, compound (a-V)) having Z' represented by the formula (a2") (i.e., structure of cyclohexylmethyl group) in the pseudo solid phase protecting group shows high solubility in nonpolar solvents as compared with other compounds (a-I) having Z represented by the formula (a2) (i.e., structure of benzyl group) in the pseudo solid phase protecting group. Therefore, using compound (a-IV) (particularly, compound (a-V)), the production method of the present invention can be performed at a higher concentration and the productivity is strikingly improved. Explanation of Z' represented by the formula (a2") is the same as that of Z represented by the aforementioned formula (a2").

In the formulas (a-IV) and (a-V), a combination wherein L is a succinyl group or a group represented by the formula (a1') (in the formula (a1'), $R^1$ and $R^2$ are each independently a $C_{1-10}$ alkyl group, $L^1$ is a divalent phenylene group, and $L^2$ is a single bond), and Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylm-ethyloxy]cyclohexylmethyloxy group, 3,4,5-tris[3',4', 5'-tris(octadecyloxy)cyclohexylmethyloxy]cyclohex-ylmethyloxy group, 3,4,5-tris(octadecyloxy) cyclohexylmethylamino group, 2,4-bis(docosyloxy) cyclohexylmethylamino group, 3,5-bis(docosyloxy) cyclohexylmethylamino group, 4-methoxy-2-[3',4',5'-tris(octadecyloxy)cyclohexylmethyloxy] cyclohexylmethylamino group, 4-methoxy-2-[3',4',5'-tris(octadecyloxy)cyclohexylmethyloxy] cyclohexylmethylamino group, 2,4-bis(dodecyloxy) cyclohexylmethylamino group, 3,5-bis[3',4',5'-tris (octadecyloxy)cyclohexylmethyloxy] cyclohexylmethylamino group, or 3,4,5-tris[3',4',5'-tris (octadecyloxy)cyclohexylmethyloxy] cyclohexylmethylamino group is preferable for solid-liquid separation.

In the formulas (a-IV) and (a-V), a combination wherein L is a succinyl group, and Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylm-ethyloxy]cyclohexylmethyloxy group, 3,4,5-tris[3',4', 5'-tris(octadecyloxy)cyclohexylmethyloxy]cyclohex-ylmethyloxy group, 3,4,5-tris(octadecyloxy) cyclohexylmethylamino group, 2,4-bis(docosyloxy) cyclohexylmethylamino group, 3,5-bis(docosyloxy) cyclohexylmethylamino group, 4-methoxy-2-[3',4',5'-tris(octadecyloxy)cyclohexylmethyloxy] cyclohexylmethylamino group, 4-methoxy-2-[3',4',5'-tris(octadecyloxy)cyclohexylmethyloxy] cyclohexylmethylamino group, 2,4-bis(dodecyloxy) cyclohexylmethylamino group, 3,5-bis[3',4',5'-tris (octadecyloxy)cyclohexylmethyloxy] cyclohexylmethylamino group, or 3,4,5-tris[3',4',5'-tris (octadecyloxy)cyclohexylmethyloxy] cyclohexylmethylamino group is more preferable for solid-liquid separation.

In the formulas (a-IV) and (a-V), a combination wherein L is a succinyl group, and Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylm-ethyloxy]cyclohexylmethyloxy group, or 3,4,5-tris[3', 4',5'-tris(octadecyloxy)cyclohexylmethyloxy]cyclo-hexylmethyloxy group is more preferable for solid-liquid separation.

In the formulas (a-IV) and (a-V), a combination wherein L is a succinyl group, and Y—Z' is 3,4,5-tris(octadecyloxy)cyclohexylmethyloxy group is particularly preferable for solid-liquid separation.

Examples of the nucleoside, nucleotide or oligonucleotide (a) also include a compound represented by the following formula (a-VI) (i.e., nucleoside or oligonucleotide).

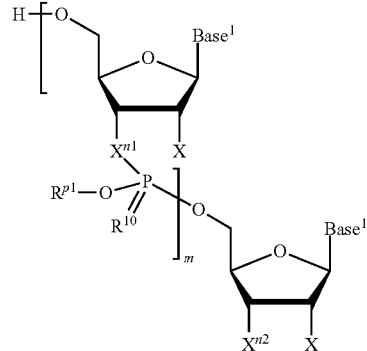

(a-VI)

wherein
at least one of Base$^1$ in the number of m+1 is a nucleic acid base protected by -L-Y—Z, and the rest is an optionally protected nucleic acid base;
$X^{n1}$ in the number of m are each independently an oxygen atom or NH;
$X^{n2}$ is a protected hydroxy group or amino group;
m, X in the number of m+1, $R^{10}$ in the number of m, $R^{p1}$ in the number of m, L, Y and Z are each independently as defined above.

In the formula (a-VI), at least one of Base$^1$ in the number of m+1 is a nucleic acid base protected by -L-Y—Z. Explanations of the nucleic acid base and -L-Y—Z are as mentioned above.

Explanation of the optionally protected nucleic acid base is also as mentioned above.

The protecting group of the protected hydroxy group ($X^{n2}$) is not particularly limited and, for example, any protecting group described in PROTECTIVE GROUPS IN ORGANIC SYNTHESIS, 3rd ed., JOHN WILLY&SONS (1999), which is incorporated herein by reference in its entirety, and the like can be mentioned. Specifically, methyl group, benzyl group, p-methoxybenzyl group, tert-butyl group, methoxyethyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, triethylsilyl group, triisopropylsilyl group, tert-butyldimethylsilyl group, [(tri-isopropylsilyl)oxy]methyl (Tom) group, 1-(4-chlorophe-nyl)-4-ethoxypiperidin-4-yl (Cpep) group and the like can be mentioned. The hydroxy-protecting group is preferably a triethylsilyl group, triisopropylsilyl group or tert-butyldim-ethylsilyl group, more preferably a tert-butyldimethylsilyl group from the aspects of economic efficiency and easy availability. Protection and deprotection of the hydroxy group are well known and can be performed by, for example, the method described in the aforementioned PROTECTIVE GROUPS IN ORGANIC SYNTHESIS.

The protecting group of the protected amino group ($X^{n2}$) is not particularly limited and, for example, the protecting groups described in Greene's PROTECTIVE GROUPS in ORGANIC SYNTHESIS, 4th ed., Wiley-Interscience (2006)), which is incorporated herein by reference in its entirety, and the like can be mentioned. Specific examples of each protecting group include pivaloyl group, pivaloy-loxymethyl group, acetyl group, trifluoroacetyl group, phe-noxyacetyl group, 4-isopropylphenoxyacetyl group, 4-tertbutylphenoxyacetyl group, benzoyl group, isobutyryl group, (2-hexyl)decanoyl group, dimethylformamidinyl group, 1-(dimethylamino)ethylidene group and 9-fluorenylmethyloxycarbonyl group. The amino-protecting group is preferably a acetyl group, phenoxyacetyl group, 4-isopropylphenoxyacetyl group, benzoyl group, isobutyryl group, (2-hexyl)decanoyl group, dimethylformamidinyl group, or 1-(dimethylamino)ethylidene group. Protection and deprotection of the amino group are well known and can be performed by, for example, the method described in the aforementioned PROTECTIVE GROUPS in ORGANIC SYNTHESIS.

In the formula (a-VI), $X^{n1}$ in the number of m are preferably oxygen atoms.

In the formula (a-VI), $X^{n2}$ is preferably a protected hydroxy group.

In the formula (a-VI), $R^{p1}$ in the number of m are preferably each independently a group represented by —CH$_2$CH$_2$WG.

In the formula (a-VI), explanations of other symbols are as mentioned above.

Compound (a-VI) is preferably a compound represented by the following formula (a-vi).

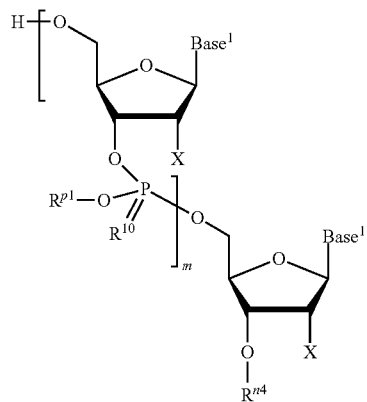

(a-vi)

wherein
$R^{n4}$ is a hydroxy-protecting group;
m, Base$^1$ in the number of m+1, X in the number of m+1, $R^{10}$ in the number of m, $R^{p1}$ in the number of m, L, Y and Z are each independently as defined above.

Explanation of $R^{n4}$ in the formula (a-vi) is the same as that of the hydroxy-protecting group for $X^{n2}$.

Explanations of other symbols in the formula (a-vi) are as mentioned above.

Examples of the nucleotide or oligonucleotide (a1) also include a compound represented by the following formula (a-VII)

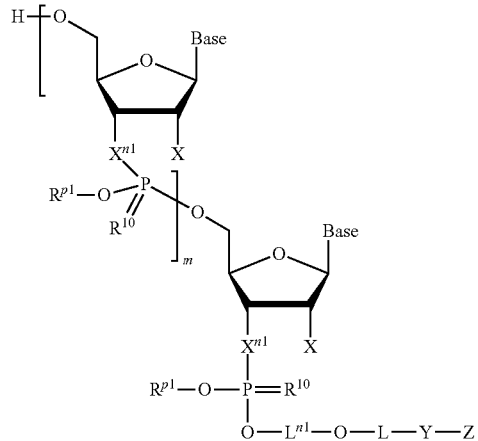

(a-VII)

wherein
$X^{n1}$ in the number of m+1 are each independently an oxygen atom or NH;
$L^{n1}$ is an organic group;
m, Base in the number of m+1, X in the number of m+1, $R^{10}$ in the number of m+1, $R^{p1}$ in the number of m+1, L, Y and Z are each independently as defined above.

In the formula (a-VII), $L^{n1}$ is preferably a $C_{2-6}$ alkylene group, more preferably an ethylene group.

In the formula (a-VII), $X^{n1}$ in the number of m+1 are preferably oxygen atoms.

In the formula (a-VII), $R^{p1}$ in the number of m+1 are preferably each independently a group represented by —CH$_2$CH$_2$WG.

Explanations of other symbols in the formula (a-VII) are as mentioned above.

Compound (a-VII) is preferably a compound represented by the following formula (a-vii) (definition and explanation of the symbols in the following formula are as mentioned above).

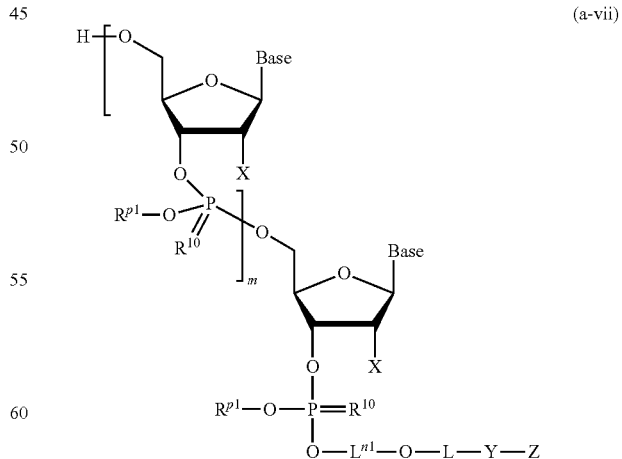

(a-vii)

Compound (a-VII) can be produced by a method known per se or a method analogous thereto. Compound (a-VII) wherein m is 0, $X^{n1}$ is an oxygen atom, and L is a succinyl group can be produced, for example, by the following steps.

(i) condensing compound Z—Y—H and succinic anhydride to produce Z—Y—CO(CH$_2$)$_2$COOH,
(ii) condensing the obtained Z—Y—CO(CH$_2$)$_2$COOH and a compound represented by formula: HO-L$^{n1}$-OQ" (wherein Q" is a temporary protecting group and L$^{n1}$ is an organic group) in the presence of a condensing agent, and deprotecting same to produce Z—Y—CO(CH$_2$)$_2$CO—O-L$^{n1}$-OH,
(iii) reacting the obtained Z—Y—CO(CH$_2$)$_2$CO—O-L$^{n1}$-OH with phosphoramidited nucleoside to produce compound (a-VII) wherein m is 0, X$^{n1}$ is an oxygen atom and L is a succinyl group.

The aforementioned condensation reaction and deprotection reaction are well known to those of ordinary skill in the art and those of ordinary skill in the art can perform them by appropriately setting the conditions.

Compound (a-VII) wherein L is other than a succinyl group can also be produced by performing a similar reaction by using the corresponding acid anhydride, corresponding dicarboxylic acid halide, active ester of corresponding dicarboxylic acid or the like instead of succinic anhydride. Compound (a-VII) wherein X$^{n1}$ is NH can be produced by performing a similar reaction by using nucleoside wherein 3'-amino group is phosphoramidited. Compound (a-VII) wherein m is one or more can be produced by repeating an elongation process using compound (a-VII) wherein m is 0 as the starting material.

The nucleoside, nucleotide or oligonucleotide (a) or the nucleotide or oligonucleotide (a1) used in this step is preferably compound (a-I), compound (a-VI) or compound (a-VII), more preferably compound (a-i), compound (a-vi) or compound (a-vii), still more preferably compound (a-i) or compound (a-vi), further preferably compound (a-i), still further preferably compound (a-II) or compound (a-IV), particularly preferably compound (a-III) or compound (a-V).

The nucleoside, nucleotide or oligonucleotide (b) used in this step has a 5'-hydroxy group protected by a temporary protecting group. The temporary protecting group of hydroxy group is not particularly limited as long as it can be deprotected under acidic conditions and can be used as a hydroxy-protecting group. Examples thereof include trityl group, 9-(9-phenyl)xanthenyl group, 9-phenylthioxanthenyl group, bis(Cis alkoxy)trityl groups such as 1,1-bis(4-methoxyphenyl)-1-phenylmethyl group (dimethoxytrityl group) and the like, mono(C$_{118}$ alkoxy)trityl groups such as 1-(4-methoxyphenyl)-1,1-diphenylmethyl group (monomethoxytrityl group) and the like, and the like. Among these, the temporary protecting group of hydroxy group is preferably a monomethoxytrityl group or a dimethoxytrityl group, more preferably a dimethoxytrityl group, in view of easiness of deprotection and easy availability.

Nucleoside, nucleotide or oligonucleotide (b) can be synthesized by a known method such as a phosphoramidite method, an H-phosphonate method, a dihalophosphine method or a oxazaphospholidine method.

The phosphoramidite method can be performed by reference to, for example, M. H. Caruthers et al., Method in Enzymology 1987, 154, 287-313; S. L. Beaucage and M. H. Caruthers, Tetrahedron Letters 1981, 22, 1859-1862; The Chemical Society of Japan, 5th Edition, Jikken Kagaku Kouza 16 organic compound IV 2010, pages 377-381), which are incorporated herein by reference in their entireties, and the like.

For example, a phosphoramiditing reagent used in the phosphoramidite method is commercially available and can also be obtained easily. For example, a nucleoside, nucleotide or oligonucleotide (b) wherein a 3'-amino group is phosphoramidited can be synthesized by reacting a nucleoside, nucleotide or oligonucleotide (b) having a 3'-amino group and 2-cyanoethyl N,N-diisopropylchlorophosphoramidite in a halogen solvent such as dichloromethane or the like.

The H-phosphonate method can be performed by reference to, for example, B. F. Froehler, Protocols for Oligonucleotides and Analogs (Chapter 4) 1993, pages 63-80; The Chemical Society of Japan, 5th Edition, Jikken Kagaku Kouza 16 organic compound IV 2010, pages 381-384), which are incorporated herein by reference in their entireties, and the like.

The dihalophosphine method can be performed by reference to, for example, The Chemical Society of Japan, 4th Edition, Jikken Kagaku Kouza 22 metal complex transition metal cluster, 1999, pages 426-431), which is incorporated herein by reference in its entirety, and the like.

Modification using the oxazaphospholidine method can be performed by reference to, for example, N. Oka et al., J. Am. Chem. Soc., 2008, 130, pages 16031-16037; N. Oka et al., Organic Letters., 2009, Vol. 11, No. 4, pages 967-970; WO 2011/08682), which are incorporated herein by reference in their entireties, and the like.

As one embodiment of the production method of a nucleoside, nucleotide or oligonucleotide (b), a method for producing nucleoside, nucleotide or oligonucleotide (b) wherein a 3'-hydroxy group is phosphoramidited (hereinafter sometimes to be abbreviated as "phosphoramidited compound (b)") from a phosphoramidited nucleoside, nucleotide or oligonucleotide (b) having a 3'-hydroxy group (hereinafter sometimes to be abbreviated as "compound (b)") is explained below.

This production method includes reactions for monoselectively activating a phosphitylating agent precursor having two nitrogen substituents on a trivalent phosphorus to give a phosphitylating agent, and phosphitylating a 3'-hydroxy group of compound (b) by using the phosphitylating agent in the presence of a base. That is, this production method is a production method of phosphoramidited compound (b) including the following step (P1) and step (P2).

(P1) A step including reacting a phosphitylating agent precursor represented by the following formula (p1):

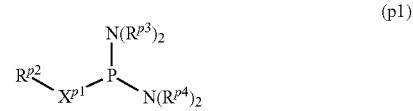

(p1)

wherein
X$^{p1}$ is an oxygen atom or a sulfur atom;
R$^{p2}$ is an aromatic ring, a hydroxy-protecting group or a thiol-protecting group;
R$^{p3}$ and R$^{p4}$ are each independently an alkyl group, and the alkyl group may form, together with the adjacent nitrogen atom, a ring,
with an activator in a solvent to prepare a phosphitylating agent represented by the following formula (p2):

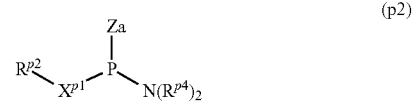

(p2)

wherein

Za is a group derived from the activator; and other symbols are as defined above, and (P2) a step including reacting compound (b) with the phosphitylating agent obtained in step (P1) in a solvent in the presence of a base to phosphitylate the 3'-hydroxy group of the compound (b).

Step (P1)

In the formula (p1), as the aromatic ring for $R^{p2}$, phenyl, 4-nitrophenyl, 2,4-dinitrophenyl, pentafluorophenyl, pentachlorophenyl, 2-bromophenyl, 4-bromophenyl, 2-methylphenyl, 2,6-dimethylphenyl and the like can be mentioned, and 4-nitrophenyl is preferable.

In the formula (p1), examples of the hydroxy-protecting group or the thiol-protecting group for $R^{p2}$ include $C_{1-6}$ alkyl group (e.g., methyl, ethyl, n-propyl, isopropyl, n-butyl, isobutyl, s-butyl, t-butyl, pentyl, isopentyl); cyanated $C_{1-6}$ alkyl group (e.g., 2-cyanoethyl, 2-cyano-1,1-dimethylethyl); ethyl group substituted by a substituted silyl group (e.g., 2-methyldiphenylsilylethyl, 2-trimethylsilylethyl, 2-triphenylsilylethyl); halogenated $C_{1-6}$ alkyl group (e.g., 2,2,2-trichloroethyl, 2,2,2-tribromoethyl, 2,2,2-trifluoroethyl); $C_{2-6}$ alkenyl group (e.g., ethenyl, 1-propenyl, 2-propenyl, 1-methyl-2-propenyl, 1-methyl-1-propenyl); $C_{3-6}$ cycloalkyl group (e.g., cyclopropyl, cyclobutyl, cyclopentyl, cyclohexyl); cyanated $C_{1-6}$ alkenyl group (e.g., 2-cyanobutenyl); $C_{7-11}$ aralkyl group (e.g., benzyl, α-naphthylmethyl, β-naphthylmethyl); and $C_{6-10}$ aryl group (e.g., phenyl, indenyl, naphthyl), more preferably cyanated $C_{1-6}$ alkyl group, particularly preferably 2-cyanoethyl.

In the formula (p1), $R^{p3}$ and $R^{p4}$ are each independently an alkyl group, and the alkyl group may form, together with the adjacent nitrogen atom, a ring (e.g., pyrrolidine). $R^{p3}$ and $R^{p4}$ are each preferably an isopropyl group.

As the phosphitylating agent precursor, the following compound is particularly preferable.

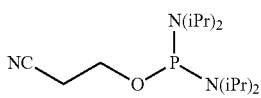

A phosphitylating agent is obtained by reacting a phosphitylating agent precursor with an activator.

An activator is an acid capable of substituting an amine on phosphoramidite to afford a reactive substituent with a hydroxy group and the like. To be specific, a weakly acidic activator with pKa of not less than 5, more preferably at least one kind selected from an azole compound with pKa of not less than 5 and a C-substituted product thereof. As the azole compound, tetrazole, triazole, imidazole and the like can be mentioned, as the C-substituted product, dicyanoimidazole, bis(trifluoromethyl)imidazole, a compound di-substituted with a halogen atom such as dichloroimidazole or the like is used. Particularly preferred are dicyanoimidazole and dichloroimidazole.

In the formula (p2), Za is a group derived from the activator and, for example, a group obtained by removing one hydrogen atom from the activator. When dicyanoimidazole is used as an activator, Za is dicyanoimidazolyl and when dichloroimidazole is used as an activator, Za is dichloroimidazolyl.

The solvent to be used in this step is not particularly limited as long as a phosphitylating agent precursor can be dissolved and an activator becomes poorly soluble, and is generally free of an acidic or basic functional group. As used herein, being "poorly soluble" approximately means that the concentration of the activator in a solvent is not more than 6 μM. Specifically, toluene, benzene, o-xylene, m-xylene, p-xylene, ethylbenzene, pentane, hexane, heptane, octane, cyclopentane, cyclohexane, diethyl ether, diisopropyl ether, tert-butyl methyl ether, cyclopentyl methyl ether, carbon tetrachloride and the like can be mentioned, toluene and cyclohexane are preferable, and toluene is particularly preferable.

The reaction temperature and reaction time of this step are not particularly limited as long as the substrate or resultant product is not precipitated, and are generally not more than 40° C., preferably 0 to 30° C., more preferably 5 to 15° C., particularly preferably about 10° C., generally 0.5 to 24 hr, preferably 1 to 12 hr, more preferably 1 to 6 hr.

The amount of the activator and phosphitylating agent precursor to be used is not particularly limited as long as the phosphitylating agent precursor is activated, and it is generally an excess amount, preferably 1.5 to 10 molar equivalents, relative to the phosphitylating agent precursor. By reacting an excess amount of an activator with a phosphitylating agent precursor in a solvent, the phosphitylating agent precursor is activated and diisopropylamine by-produced in phosphitylating is simultaneously precipitated as a salt with the activator. Therefore, where necessary, a step for separating insoluble materials such as precipitate and the like can be performed between step (P1) and the following step (P2), and is preferably performed.

Step (P2)

In this step, phosphoramidited compound (b) is produced by phosphitylating the 3'-hydroxy group of compound (b) by reacting compound (b) with the phosphitylating agent obtained in step (P1) in a solvent in the presence of a base.

As the solvent to be used in this step, those similar to the solvent used in step (P1) (e.g., toluene) can be used. As the solvent to be used in this step, for example, dichloromethane, chloroform and the like can be mentioned. A mixed solvent of toluene and dichloromethane is preferable.

As a base to be used in this step, a base having basicity sufficient for neutralization of an acid (activator) produced by the reaction, and free of removal of cyanoethyl on phosphoric acid or formation of a P—N bond is selected. As such base, specifically, base with pKa 5 to 8, preferably, collidine, N-methylmorpholine, diethylaniline and the like can be used. When a base with pKa high than 8 is used, decyanation becomes remarkable, and when a base with pKa less than 5 is used, an activator regenerated as the reaction proceeds is not trapped sufficiently and a byproduct is produced.

In step (P2), a phosphitylating agent precursor may not be added but is preferably added.

Examples of the nucleoside, nucleotide or oligonucleotide (b) include a compound represented by the following formula (b-I) (i.e., nucleoside or oligonucleotide).

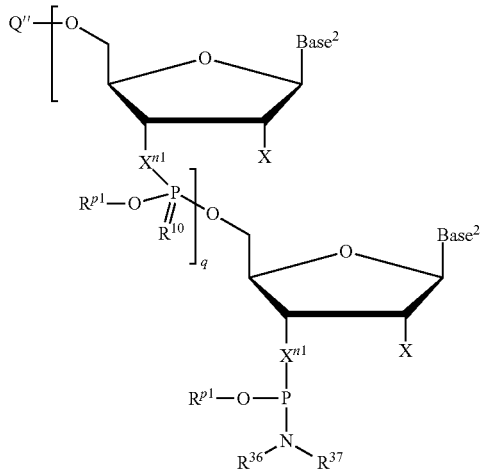

(b-I)

wherein
- q is an integer of not less than 0;
- Base$^2$ in the number of q+1 are each independently a nucleic acid base optionally protected by a protecting group selected from -L-X—Z and protecting groups used for nucleic acid synthesis;
- X in the number of q+1, $R^{p1}$ in the number of q+1, $R^{10}$ in the number of q, L, X and Z are each independently as defined above;
- $X^{n1}$ in the number of q+1 are each independently an oxygen atom or NH;
- Q" is a temporary protecting group of hydroxy group removable under acidic conditions;
- $R^{36}$ and $R^{37}$ are each independently an alkyl group, or a 5- or 6-membered saturated cyclic amino group formed together with the adjacent nitrogen atom, and the saturated cyclic amino group, optionally has, as a ring-constituting atom, one oxygen atom or sulfur atom besides nitrogen atom.
- $R^{36}$ and $R^{37}$ are preferably each independently a $C_{1-10}$ alkyl group, or a 5- or 6-membered saturated cyclic amino group formed together with the adjacent nitrogen atom, more preferably a $C_{1-10}$ alkyl group, further preferably a $C_{1-6}$ alkyl group.

Explanation of the temporary protecting group of hydroxy group removable under acidic conditions is as mentioned above. Q" is preferably a monomethoxytrityl group or a dimethoxytrityl group, more preferably a dimethoxytrityl group.

The amino group of the nucleic acid base in the formula (b-I) is preferably protected by a protecting group. As the protecting group, a protecting group selected from -L-X—Z and protecting groups used for nucleic acid synthesis can be mentioned. Explanations of L, X and Z are as mentioned above. As the protecting group used for nucleic acid synthesis, acetyl group, phenoxyacetyl group, 4-isopropylphenoxyacetyl group, benzoyl group, isobutyryl group, (2-hexyl)decanoyl group, dimethylformamidinyl group, and =NC($R^{11}$)—N($R^{12}$) ($R^{13}$) group wherein $R^{11}$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbocycle is preferable. Examples of the aforementioned =NC($R^{11}$)—N($R^{12}$) ($R^{13}$) group include a 1-(dimethylamino)ethylidene group. When compound (b-I) has plural amino groups, only one kind or two or more kinds of the amino-protecting group may be used.

When q is 0, compound (b-I) is a nucleoside, and when q is one or more, compound (b-I) is an oligonucleotide. As compound (b-I) used in this step, q is preferably not more than 49, more preferably not more than 29, further preferably not more than 19, particularly preferably not more than 4, and most preferably not more than 2.

X in the number of q+1 are each independently preferably a hydrogen atom, a halogen atom or an optionally protected hydroxy group, more preferably a hydrogen atom or an optionally protected hydroxy group.

Base$^2$ are each independently preferably a nucleic acid base optionally protected by a protecting group selected from protecting groups used for nucleic acid synthesis.

$R^{p1}$ in the number of q+1 are preferably each independently a group represented by $CH_2CH_2WG$.

$X^{n1}$ in the number of q+1 are preferably oxygen atoms.

Explanations of L, X and Z are as mentioned above.

Compound (b-I) is preferably a compound represented by the following formula (b-i).

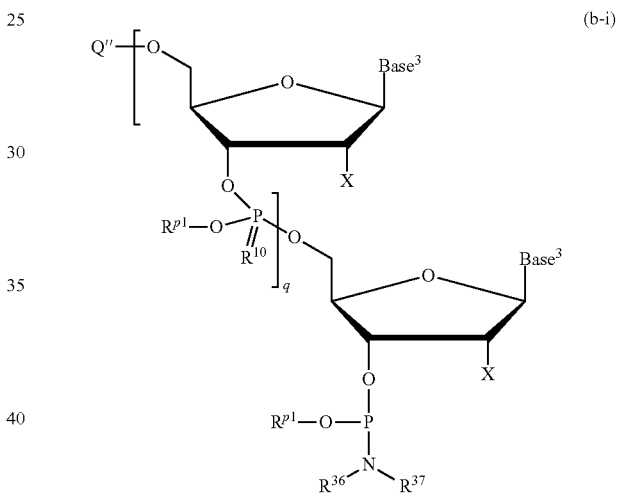

(b-i)

wherein
- Base$^3$ in the number of q+1 are each independently a nucleic acid base optionally protected by protecting groups used for nucleic acid synthesis,
- q, X in the number of q+1, $R^{p1}$ in the number of q+1, $R^{10}$ in the number of q, Q", $R^{36}$ and $R^{37}$ are each independently as defined above.

In the formula (b-i), explanations of the protecting groups used for nucleic acid synthesis, q, X in the number of q+1, $R^{p1}$ in the number of q+1, $R^{10}$ in the number of q, Q", $R^{36}$ and $R^{37}$ are as mentioned above.

A combination of the nucleoside, nucleotide or oligonucleotide (a) or nucleotide or the oligonucleotide (a1), and the nucleoside, nucleotide or oligonucleotide (b) used in this step is
- preferably a combination of compound (a-I), compound (a-VI) or compound (a-VII) and compound (b-I),
  - more preferably a combination of compound (a-i), compound (a-vi) or compound (a-vii) and compound (b-i),
    - still more preferably a combination of compound (a-i) or compound (a-vi) and compound (b-i),
      - further preferably a combination of compound (a-i) and compound (b-i), still further preferably a combination of compound (a-II) or compound (a-IV) and compound (b-i),
particularly preferably a combination of compound (a-III) or compound (a-V) and compound (b-i).

When the progress of the condensation reaction in this step is slow, a condensing agent (e.g., pyridine. trifluoroacetate, tetrazole, 5-benzylthio-1H-tetrazole, 4,5-dicyanoimidazole etc.) may be added.

In the liquid phase method, this step is performed in a non-polar solvent. Examples of the non-polar solvent include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Only one kind of non-polar solvent may be used, or two or more kinds thereof may be used in combination. As the non-polar solvent, halogenated solvent, aromatic solvents, ester solvent, aliphatic solvent, and a combination of these are preferable; dichloromethane, chloroform, 1,2-dichloroethane, benzene, toluene, xylene, mesitylene, hexane, pentane, heptane, nonane, cyclohexane, ethyl acetate, isopropyl acetate and a combination of these are more preferable; and chloroform, dichloromethane, toluene, and a combination of these are further preferable. The same applies to the non-polar solvents used in the steps after this step.

In the liquid phase method, the amount of nucleoside, nucleotide or oligonucleotide (b) to be used in this step is, for example, 1 to 10 mol, preferably 1 to 5 mol, per 1 mol of the amount of use of nucleoside, nucleotide or oligonucleotide (a), or nucleotide or oligonucleotide (a1) in this step. In the solid phase method, it is, for example, 1 to 20 mol, preferably 1 to 10 mol, per 1 mol of the amount of use of nucleoside, nucleotide or oligonucleotide (a) in this step.

The reaction temperature in this step is not particularly limited as long as the reaction proceeds. In the liquid phase method, 0° C. to 100° C. is preferable, and 20° C. to 50° C. is more preferable. In the solid phase method, 10° C. to 40° C. is preferable, and 20° C. to 30° C. is more preferable. The reaction time varies depending on the kind of the starting material to be used, reaction temperature and the like. In the liquid phase method, it is, for example, 5 min to 24 hr; in the solid phase method, it is, for example, 1 min to 30 min.

(Quenching of Nucleoside, Nucleotide or Oligonucleotide (b) in which 3'-Hydroxyl Group or 3'-Amino Group is Modified by Method Selected from Phosphoramidite Method, H-Phosphonate Method, Dihalophosphine Method and Oxazaphospholidine Method)

In the present invention, step (2) ((2-1) (sulfurization) or (2-2) (oxidation)) and step (3) (deprotection) are performed after step (1) (condensation). In the liquid phase method, therefore, it is preferable to quench nucleoside, nucleotide or oligonucleotide (b) before step (2) to suppress byproducts in step (2) and (3). Therefore, the production method of the present invention preferably contains step for adding a quencher to the reaction solution after condensation.

An agent known as a quencher for nucleoside or oligonucleotide in which a 3'-hydroxyl group or 3'-amino group is modified by a method selected from a phosphoramidite method, an H-phosphonate method, a dihalophosphine method and an oxazaphospholidine method in the field of oligonucleotide production methods can be used as a quenching agent in this step. Only one kind of a quencher may be used, or two or more kinds thereof may be used in combination. Examples of the quencher include alcohols, phenols and amines.

Examples of the alcohols usable as a quencher include optionally halogenated monohydric alcohols such as methanol, 2-propanol, t-butanol, 2,2,2,-trifluoroethanol, tetrahydrofurfuryl alcohol, furfurylalcohol, 2,3-O-isopropylidene-D-ribofuranose, 3'-O-triisopropylsilyl-thymidine and the like, optionally halogenated polyhydric alcohols such as ethylene glycol, diethylene glycol and the like.

Examples of the phenols usable as a quencher include 4-nitrophenol and pentafluorophenol. Examples of the amines usable as a quencher include morpholine.

The quencher is preferably at least one selected from alcohols and amines, more preferably at least one selected from methanol, 2-propanol, t-butanol, 2,2,2-trifluoroethanol, tetrahydrofurfuryl alcohol, and morpholine. To prevent falling off of the amino-protecting group of nucleic acid base in the oligonucleotide (e) during deprotection in step (3) (deprotection), the quencher is further preferably at least one selected from 2-propanol, t-butanol and 2,2,2-trifluoroethanol.

The amount of the quencher to be used in this step is preferably 1 to 20 mol, more preferably 1 to 10 mol, further preferably 1 to 5 mol, per 1 mol of the amount of the nucleoside, nucleotide or oligonucleotide (b) to be used in step (1).

The temperature of the reaction solution after addition of a quencher is not particularly limited as long as the nucleoside, nucleotide or oligonucleotide (b) can be quenched and is preferably 5° C. to 40° C., more preferably 15° C. to 30° C.

The stirring time of the reaction solution after addition of a quencher varies depending on the kind of the quencher to be used, temperature and the like and is, for example, 10 min to 3 hr.

Step (2): (2-1) (sulfurization)

In this step, a phosphite form or phosphorous acid diester (c) in which the 5'-hydroxyl group is protected by a temporary protecting group that can be removed under acidic conditions is reacted with a sulfurizing agent to convert the phosphite bond or phosphorous acid diester bond to a phosphorothioate bond, whereby oligonucleotide (d) having a phosphorothioated moiety in which the 5'-hydroxyl group is protected by a temporary protecting group that can be removed under acidic conditions is obtained. Only one kind of a sulfurizing agent may be used, or two or more kinds thereof may be used in combination.

The sulfurizing agent to be used in this step is not particularly limited as long as it is capable of converting a phosphite bond or a phosphorous acid diester bond to a phosphorothioate bond. 5-[(N,N-dimethylaminomethylidene)amino]-3H-1,2,4-dithiazole-3-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), dipentamethylenethiuram tetrasulfide, 5-phenyl-3H-1,2,4-dithiazol-3-one (POS), 3-amino-1,2,4-dithiazole-5-thione (ADTT, xanthan hydride), and sulfur are preferable.

Since a good reaction can proceed, 5-[(N,N-dimethylaminomethylidene)amino]-3H-1,2,4-dithiazole-3-thione (DDTT), 3H-1,2-benzodithiol-3-one-1,1-dioxide (Beaucage reagent), 3H-1,2-benzodithiol-3-one, phenylacetyl disulfide (PADS), and 5-phenyl-3H-1,2,4-dithiazol-3-one (POS) are more preferable, 5-[(N,N-dimethylaminomethylidene)amino]-3H-1,2,4-dithiazole-3-thione (DDTT), 3H-1,2-benzodithiol-3-one-1,1-dioxide (Beaucage reagent), and 5-phenyl-3H-1,2,4-dithiazol-3-one (POS) are further preferable, and 5-[(N,N-dimethylaminomethylidene)amino]-3H-1,2,4-dithiazole-3-thione (DDTT) and 5-phenyl-3H-1,2,4-dithiazol-3-one (POS) are particularly preferable. Such sulfurizing agent can be used by diluting with a suitable solvent at a concentration of 0.05-2 M. Such diluent solvent is not particularly limited as long as it is inert to the reaction and, for example, dichloromethane, acetonitrile, pyridine or a mixed solvent of any of these can be mentioned.

The amount of the sulfurizing agent to be used is, for example, 1 to 50 mol, preferably 1 to 10 mol, per 1 mol of a phosphite form or phosphorous acid diester (c) in the case of the liquid phase method. In the case of solid phase method, it is, for example, 1 to 100 mol, preferably 1 to 20 mol.

The reaction temperature is not particularly limited as long as the reaction proceeds. In the liquid phase method, it is preferably 0° C. to 100° C., more preferably 20° C. to 50° C. In the solid phase method, it is preferably 10° C. to 40° C., more preferably 20° C. to 30° C. The reaction time varies depending on the kind of the phosphite form or phosphorous acid diester (c), the kind of the sulfurizing agent to be used, reaction temperature and the like. In the liquid phase method, it is, for example, 1 min to 3 hr and, in the solid phase method, it is, for example, 1 min to 30 min.

step (2): (2-2) (oxidation)

In this step, a phosphite form or phosphorous acid diester (c) in which the 5'-hydroxyl group is protected by a temporary protecting group that can be removed under acidic conditions is reacted with an oxidizing agent to convert the phosphite bond or phosphorous acid diester bond to a phosphate (including phosphoric acid diester and phosphoric acid triester) bond, whereby oligonucleotide (d-2) having a phosphated moiety in which the 5'-hydroxyl group is protected by a temporary protecting group that can be removed under acidic conditions is obtained. Only one kind of an oxidizing agent may be used, or two or more kinds thereof may be used in combination.

The oxidizing agent to be used in this step is not particularly limited as long as it is capable of converting a phosphite bond or a phosphorous acid diester bond to a phosphate bond. Since a good reaction can proceed, iodine is preferable.

Such oxidizing agent can be used by diluting with a suitable solvent. The dilution solvent is not particularly limited as long as it is inert to the reaction. For example, pyridine, water, and any mixed solvent of these can be mentioned, and a mixed solvent of pyridine and water is preferable. Pyridine is used at 3 to 10 mol, preferably 4 to 6 mol, per 1 mol of the oxidizing agent, and water is used at 1 to 5 mol, preferably 2 to 4 mol, per 1 mol of the oxidizing agent.

The amount of the oxidizing agent to be used is, for example, 1 to 50 mol, preferably 1 to 10 mol, per 1 mol of the phosphite form or phosphorous acid diester (c) in the liquid phase method. In the solid phase method, it is, for example, 1 to 100 mol, preferably 1 to 20 mol.

The reaction temperature is not particularly limited as long as the reaction proceeds. In the liquid phase method, it is preferably 0° C. to 100° C., more preferably 20° C. to 50° C. In the solid phase method, it is preferably 10° C. to 40° C., more preferably 20° C. to 30° C. The reaction time varies depending on the kind of the phosphite form or phosphorous acid diester (c), the kind of the oxidizing agent to be used, reaction temperature and the like. In the liquid phase method, it is, for example, 1 min to 3 hr and, in the solid phase method, it is, for example, 1 min to 30 min.

Step (3): (3-1) (Removal of Temporary Protecting Group of Oligonucleotide Having Phosphorothioated Moiety), or (3-2) (Removal of Temporary Protecting Group of Oligonucleotide Having Phosphated Moiety)

In this step, the temporary protecting group of oligonucleotide (d-1) having a phosphorothioated moiety is removed by an acid to obtain a crude product of an oligonucleotide (e-1) having a phosphorothioated moiety in which the 5'-hydroxyl group is not protected. In this step, moreover, the temporary protecting group of oligonucleotide (d-2) having a phosphated moiety is removed by an acid to obtain a crude product of an oligonucleotide (e-2) having a phosphated moiety in which the 5'-hydroxyl group is not protected. Only one kind of acid may be used, or two or more kinds thereof may be used in combination.

The acid to be used in this step is not particularly limited as long as a good deprotection can be achieved, and examples thereof include carboxylic acids such as trifluoroacetic acid, dichloroacetic acid, trichloroacetic acid, acetic acid and the like, sulfonic acids such as trifluoromethanesulfonic acid, methanesulfonic acid, p-toluenesulfonic acid and the like, phosphonic acid, phosphoric acid and the like. Since the present invention aims to solve the problem that the deprotected 5'-hydroxyl group is acylated in the deprotection step, at least a carboxylic acid capable of acylating a hydroxyl group is preferably contained, and at least trifluoroacetic acid, dichloroacetic acid or trichloroacetic acid is more preferably contained. These acids may be diluted with the aforementioned non-polar solvents. When the aforementioned acids are used, the acidity may be appropriately adjusted by combining with a specific base and then used. The amount of the acid to be used in this step is, for example, 1 to 100 mol, preferably 1 to 40 mol, in the liquid phase method and, for example, 1 to 200 mol, preferably 1 to 80 mol, in the solid phase method, per 1 mol of oligonucleotide (d-1) having a phosphorothioated moiety or 1 mol of oligonucleotide (d-2) having a phosphated moiety.

The reaction temperature in this step is not particularly limited as long as the reaction proceeds. In the liquid phase method, it is preferably −10° C. to 50° C., more preferably 0° C. to 40° C. In the solid phase method, it is preferably 10° C. to 50° C., more preferably 20° C. to 30° C. The reaction time varies depending on the kind of the oligonucleotide (d-1) having a phosphorothioated moiety or oligonucleotide (d-2) having a phosphated moiety to be used, the kind of the acid and the kind of the non-polar solvent, reaction temperature and the like. In the liquid phase method, it is, for example, 5 min to 5 hr and, in the solid phase method, it is, for example, 1 min to 30 min.

In this step, it is preferable to use a cation scavenger during or after the reaction to remove a temporary protecting group of the 5'-hydroxyl group of the oligonucleotide (d-1) having a phosphorothioated moiety or oligonucleotide (d-2) having a phosphated moiety. That is, the removal reaction of the temporary protecting group is preferably performed in the presence of a cation scavenger or a cation scavenger is preferably added to the reaction system after the removal reaction of the temporary protecting group. Only one kind of the cation scavenger may be used, or two or more kinds thereof may be used in combination.

The cation scavenger is not particularly limited as long as re-protection (returning to material) by a temporary protecting group removed or a side reaction with the deprotected functional group does not proceed. A pyrrole derivative such as pyrrole, 2-methylpyrrole, 3-methylpyrrole, 2,3-dimethylpyrrole, 2,4-dimethylpyrrole or the like; an indole derivative such as indole, 3-methylindole, 4-methylindole, 5-methylindole, 6-methylindole, 7-methylindole, 5,6-dimethylindole, 6,7-dimethylindole or the like; a furan derivative such as 2-methylfuran, 2,3-dimethylfuran, 2-methyl-3-(methylthio)furan, menthofuran or the like can be used. Since a good cation trap effect can be obtained, pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio)furan, menthofuran are preferable, pyrrole, 3-methylpyrrole, 2,4-dimethylpyrrole, indole, 4-methylindole, 5-methylindole, 6-methylindole, 7-methylindole, 5,6-dimethylindole, 6,7-dimethylindole are more preferable, pyrrole, 3-methylpyrrole, indole are further preferable, pyrrole, indole are still further preferable, and pyrrole is particularly preferable. The amount of the cation scavenger to be used in this step is, for example, 1-50 mol, preferably 5-20 mol, per 1 mol of the oligonucleotide (d-1) having a phosphorothioated moiety or oligonucleotide (d-2) having a phosphated moiety.
(Neutralization)

In the liquid phase method, a base may be added to the reaction system after step (3) (deprotection) to neutralize the acid used in step (3). In the production method of the present invention, the acid used in step (3) can be removed from a crude product of the oligonucleotide (e-1) having a phosphorothioated moiety or oligonucleotide (e-2) having a phosphated moiety by solid-liquid separation or extraction and washing after step (4) as necessary. Thus, a neutralization step is not essential.

In this step, only one kind of base may be used, or two or more kinds thereof may be used in combination. As the base to be used, an organic base is preferable. As the organic base, pyridine, 2,4,6-trimethylpyridine, benzimidazole, 1,2,4-triazole, N-phenylimidazole, 2-amino-4,6-dimethylpyrimidine, 1,10-phenanthrolin, imidazole, N-methylimidazole, 2-chlorobenzimidazole, 2-bromobenzimidazole, 2-methylimidazole, 2-phenylbenzimidazole, N-phenylbenzimidazole, 5-nitrobenzimidazole are preferable, pyridine, 2,4,6-trimethylpyridine, benzimidazole, 1,2,4-triazole, N-phenylimidazole, N-methylimidazole, 2-amino-4,6-dimethylpyrimidine, 1,10-phenanthrolin are more preferable, pyridine, 2,4,6-trimethylpyridine, benzimidazole, 1,2,4-triazole, N-phenylimidazole are further preferable, pyridine, 2,4,6-trimethylpyridine, benzimidazole, 1,2,4-triazole are particularly preferable, and pyridine, 2,4,6-trimethylpyridine, benzimidazole are most preferable.

The amount of the base to be used in this step is, for example, 1 to 10 mol, preferably 1 to 3 mol, per 1 mol of the amount of the acid to be used in step (3).

Step (4): (4-1) (Solvolysis of Oligonucleotide Having a Phosphorothioated Moiety), or (4-2) (Solvolysis of Oligonucleotide Having a Phosphated Moiety)

In this step, an oligonucleotide having a phosphorothioated moiety with an acylated 5'-hydroxyl group, which is contained in a crude product of an oligonucleotide (e-1) having the phosphorothioated moiety, is deacylated by solvolysis. In this step, moreover, an oligonucleotide having a phosphated moiety with an acylated 5'-hydroxyl group, which is contained in a crude product of an oligonucleotide (e-2) having the phosphated moiety, is deacylated by solvolysis.

The "acylation" in this step means a reaction of the acid, which is added in the previous step (3-1) or (3-2) to remove the temporary protecting group of the 5'-hydroxyl group, with the 5'-hydroxyl group. As a result of the reaction, R—C(=O)— binds to the 5'-position oxygen atom when the acid is carboxylic acid, R—S(=O)$_2$— binds to the 5'-position oxygen atom when the acid is sulfonic acid, H—P(=O) (OH)— binds to the 5'-position oxygen atom when the acid is phosphonic acid, and HO—P(O)$_2$— binds to the 5'-position oxygen atom when the acid is phosphoric acid. On the other hand, the "deacylation" in this step means that the generated acylated product becomes a 5'-hydroxyl group by solvolysis in this step.

This step is preferably performed under weak acidic to weak basic conditions so that the cyanoalkyl group (e.g., cyanoethyl group), alkoxycarbonylalkyl group (e.g., ethoxycarbonylethyl group), halogenophenyl group (2-chlorophenyl group) and the like bonded to the oxygen atom or sulfur atom of the phosphorothioated moiety or phosphated moiety will not fall off. Particularly, in the case of a basically unstable cyanoalkyl group (e.g., cyanoethyl group), it is desirable to prevent the cyanoalkyl group (e.g., cyanoethyl group) from falling off. In addition, it is necessary to select bases and nucleophiles that are used with attention to the falling off of side chain protecting groups on bases such as acetyl group and benzoyl group, the basicity of the base (non-nucleophilic base) and the pKa of the nucleophilic substance as necessary.

The solvent to be used in this step is not particularly limited as long as it can deacylate an oligonucleotide having a phosphorothioated moiety with an acylated 5'-hydroxyl group. The solvent to be used in this step is not particularly limited as long as it can deacylate an oligonucleotide having a phosphated moiety with an acylated 5'-hydroxyl group. It is preferably a mixture of a base and a nucleophilic substance. The base can also be used in a supported state on a solid phase carrier. As the base, an organic base is preferable and, for example, tertiary amine (e.g., N,N-dimethylaminoacetonitrile, N,N-diethylaminoacetonitrile, N,N-diisopropylaminoacetonitrile, 1-pyrrolidineacetonitrile, 1-piperidineacetonitrile, N,N-dimethylaniline), a neutralized salt of tertiary amine and acidic counter (e.g., triethylamine hydrochloride), a non-nucleophilic base such as tertiary amine with basicity adjusted with an acid (e.g., mixture of diisopropylethylamine:formic acid=5:3) and the like, a heterocyclic compound having a nitrogen atom (e.g., pyridine derivatives such as pyridine, collidine, lutidine, methylpyridine and the like, imidazole compounds such as N-methylimidazole and the like) and the like can be mentioned. A pyridine derivative is preferable. As the nucleophilic substance, water and alcohol derivatives are preferable; for example, water, methanol, ethanol, isopropyl alcohol, butanol, benzyl alcohol, tetrahydrofurfuryl alcohol and the like can be mentioned, and water and methanol are preferable. The mixture of a base and a nucleophilic substance is preferably a mixture of at least one kind of base selected from the group consisting of non-nucleophilic base and pyridine derivative, and at least one kind of nucleophilic substance selected from the group consisting of water and alcohol derivative, more preferably a mixture of at least one kind of base selected from the group consisting of pyridine, collidine, lutidine and methylpyridine, and at least one kind of nucleophilic substance selected from the group consisting of water, methanol, ethanol, isopropyl alcohol, butanol, benzyl alcohol and tetrahydrofurfuryl alcohol, further preferably a mixture of pyridine and water, a mixture of pyridine and methanol, a mixture of pyridine and ethanol, a mixture of collidine and water, a mixture of collidine and methanol, a mixture of collidine and ethanol, a mixture of lutidine and water, a mixture of lutidine and methanol, or a mixture of lutidine and ethanol, and a mixture of pyridine and water, a mixture of pyridine and methanol, and a mixture of pyridine and ethanol are particularly preferable.

In one embodiment of the present invention, the pKa of the non-nucleophilic base is preferably 3 to 10, more preferably 4 to 9, further preferably 4 to 7, from the aspect of the suppression of falling off of the cyanoethyl group and the nucleic acid base side chain protecting group.

In another embodiment of the present invention, when the nucleophilic substance contains at least water, the basicity (pH) thereof can also be adjusted with an inorganic salt (e.g., aqueous sodium carbonate solution, aqueous sodium hydrogen carbonate solution, buffer solution and the like). For example, for solvolysis after detritylation of the first residue, relatively strong basic conditions can be used because the cyanoethyl group has not yet been attached. Furthermore, since the TFA used in the detritylation must be neutralized first to become basic, it can be neutralized with a strong base first and then adjusted with a weak base. The pH thereof is preferably 3.0 to 8.0, more preferably 4.0 to 7.0, further preferably 4.5 to 6.0.

The amount of the base to be used in this step varies depending on the kind of the base to be used. In the liquid phase method, when this step is performed in one pot without purification after the deprotection step, or in the case of the solid phase method, the acid used in the deprotection remains in the reaction solution, which requires more bases. For this reason, in the liquid phase method (one-pot method) and the solid phase method, 1 to 10 equivalents, preferably 3 to 5 equivalents, of the base are required with respect to the amount of the acid used. On the other hand, in a method other than the above-mentioned solid phase method and the liquid phase method (one-pot method), 1 to 5 mol, preferably 1 to 3 mol, of the base is required per 1 mol of a crude product of the oligonucleotide (e-1) having a phosphorothioated moiety or a crude product of oligonucleotide (e-2) having a phosphated moiety.

The reaction temperature in this step is not particularly limited as long as the reaction proceeds. In the liquid phase method, it is preferably 0° C. to 50° C., more preferably 5° C. to 30° C. In the solid phase method, it is preferably 5° C. to 40° C., more preferably 10° C. to 30° C. The reaction time varies depending on the kind of a crude product of the oligonucleotide (e-1) having a phosphorothioated moiety or a crude product of oligonucleotide (e-2) having a phosphated moiety and the solvent to be used, reaction temperature and the like. In the liquid phase method, it is, for example, 10 min to 24 hr and, in the solid phase method, it is, for example, 1 min to 30 min.

(Solid-Liquid Separation or Extraction)

The production method of the present invention when it is a liquid phase method may include a step of adding a polar solvent to a reaction mixture containing the oligonucleotide (e-1) having a phosphorothioated moiety obtained in step (4-1) or oligonucleotide (e-2) having a phosphated moiety obtained in step (4-2) to allow for precipitation and purification of the oligonucleotide (e-1) having a phosphorothioated moiety or oligonucleotide (e-2) having a phosphated moiety (solid-liquid separation), or may include a step of adding a polar solvent to the reaction mixture, separating layers between the polar solvent and the non-polar solvent, transferring the oligonucleotide (e-1) having a phosphorothioated moiety or oligonucleotide (e-2) having a phosphated moiety into the non-polar solvent layer to perform purification (extraction). In both solid-liquid separation and extraction, only one kind of the polar solvent may be used, or two or more kinds thereof may be used in combination.

The solid-liquid separation is explained. Examples of the polar solvent to be used in solid-liquid separation include alcohol solvents such as methanol, ethanol, isopropanol and the like; nitrile solvents such as acetonitrile, propionitrile and the like; ketone solvents such as acetone, 2-butanone and the like; polar ether solvents such as 1,4-dioxane, tetrahydrofuran and the like; amide solvents such as dimethylformamide, dimethylacetamide, N-methylpiperidone and the like, sulfoxide solvents such as dimethyl sulfoxide and the like; water, and the like, and a mixed solvent of these. Of these, nitrile solvents are preferable, and acetonitrile is more preferable.

To increase the collection rate of the oligonucleotide (e-1) having a phosphorothioated moiety or oligonucleotide (e-2) having a phosphated moiety, the amount of the polar solvent to be added in the solid-liquid separation is preferably 1 to 20 mL, more preferably 1 to 10 mL, further preferably 1 to 5 mL, per 1 mL of the non-polar solvent contained in the reaction solution.

The polar solvent may contain water to minimize the loss of oligonucleotide (e-1) having a phosphorothioated moiety or so oligonucleotide (e-2) having a phosphated moiety in a polar solvent. In this case, the content of water in the polar solvent is preferably 1 to 10% (v/v), more preferably 3 to 8% (v/v). When the content of water is too low, the loss of the oligonucleotide (e-1) having a phosphorothioated moiety or oligonucleotide (e-2) having a phosphated moiety in a polar solvent may increase, and when the water content is too high, removal of impurities into a polar solvent tends to be insufficient.

To increase collection rate of the oligonucleotide (e-1) having a phosphorothioated moiety or oligonucleotide (e-2) having a phosphated moiety, a precipitation promoter (e.g., 3,4,5-tris(octadecyloxy)benzyl 2,2-dimethylpropanoate) described in WO 2016/117663), which is incorporated herein by reference in its entirety, may also be used.

Extraction is now explained. The extraction operation is not particularly limited. Preferably, a polar solvent is added to a reaction mixture containing oligonucleotide (e-1) having a phosphorothioated moiety or oligonucleotide (e-2) having a phosphated moiety, separating layers between the polar solvent and the non-polar solvent, the oligonucleotide (e-1) having a phosphorothioated moiety or oligonucleotide (e-2) having a phosphated moiety is transferred into the non-polar solvent layer. By this extraction, impurities such as remaining starting materials, byproducts and the like can be transferred into the polar solvent layer and removed.

Examples of the polar solvent to be used for extraction include alcohol solvents such as methanol, ethanol, isopropanol and the like, nitrile solvents such as acetonitrile, propionitrile and the like, ketone solvents such as acetone, 2-butanone and the like, polar ether solvents such as 1,4-dioxane, tetrahydrofuran and the like, amide solvents such as N,N-dimethylformamide, N,N-dimethylacetamide, N-methylpiperidone and the like, sulfoxide solvents such as dimethyl sulfoxide and the like, water, and the like, and a mixed solvent of two or more kinds thereof. Of these, amide solvents, nitrile solvents, and combination of these are preferable, acetonitrile, N,N-dimethylformamide, N-methylpiperidone, and combination of these are more preferably used. Of these, nitrile solvents are preferable, and acetonitrile is more preferable.

The polar solvent used for extraction may contain water to improve separation of layer from non-polar solvent. In this case, the content of water in the polar solvent is preferably 1 to 10% (v/v), more preferably 3 to 8% (v/v). When the water content is too low, the separation of layer may not be improved much. When the water content is too high, solubility of impurity in a polar solvent decreases and the removal efficiency thereof tends to decrease.

For extraction, a non-polar solvent may be added as necessary to the reaction solution together with the polar solvent. Only one kind of non-polar solvent may be used, or two or more kinds thereof may be used in combination. As the non-polar solvent to be added as necessary, halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like can be mentioned. Of these, aromatic solvents, aliphatic solvents, or a combination of these is preferable, benzene, toluene, hexane, pentane, heptane, nonane, cyclohexane, a combination of these or the like is preferable, toluene, heptane, nonane or a combination of these is more preferable, toluene, heptane or a combination of these is further preferable, and heptane is particularly preferable.

After layer separation between polar solvent and non-polar solvent, impurity can be removed by an operation to remove the polar solvent layer. The amount of impurity may be further decreased by adding a polar solvent to the non-polar solvent layer after removal of the polar solvent layer, stirring the mixture to separate the layers, and performing an operation to remove the polar solvent.

The amount of the polar solvent to be used for one extraction operation is preferably 0.1 to 10 mL, more preferably 0.2 to 5 mL, further preferably 0.2 to 1 mL, per 1 mL of the non-polar solvent.

Concentration of the obtained non-polar solvent layer enables isolation of the oligonucleotide (e-1) having a phosphorothioated moiety or oligonucleotide (e-2) having a phosphated moiety.

(Deprotection and Isolation)

The production method of the present invention when it is a liquid phase method may include a step of removing, after the solid-liquid separation or extraction, all protecting groups of the obtained oligonucleotide (e-1) having a phosphorothioated moiety or oligonucleotide (e-2) having a phosphated moiety, and isolating an unprotected oligonucleotide having a phosphorothioated moiety or unprotected oligonucleotide having a phosphated moiety. As a deprotection method, for example, all protecting groups of the oligonucleotide can be removed according to the deprotection method described in PROTECTIVE GROUPS IN ORGANIC SYNTHESIS, 3rd ed., JOHN WILLY&SONS (1999)), which is incorporated herein by reference in its entirety, and the like. To be specific, pseudo solid phase protecting group, and phenoxyacetyl group, acetyl group and the like, all of which are protecting groups of nucleic acid base; and cyanoethyl group and the like protecting a phosphoric acid skeleton can all be removed by a treatment with aqueous ammonia, aqueous ammonia/ethanol solution, or a mixture of aqueous ammonia and aqueous methylamine solution. In addition, 5' hydroxy-protecting group can be removed by a treatment with the acid used in step (3) or an appropriately diluted solution of such acid. Unprotected (i.e., without a protecting group) oligonucleotide is easily degraded by an enzyme, and therefore, unprotected oligonucleotide is preferably isolated under control of air cleanliness.

The production method of the present invention when it is a solid phase method may include a step of washing, after step (4), the solid phase with a solvent, separating the obtained oligonucleotide (e-1) having a phosphorothioated moiety or oligonucleotide (e-2) having a phosphated moiety from the solid phase, removing all protecting groups thereof, and isolating an unprotected oligonucleotide having a phosphorothioated moiety or unprotected oligonucleotide having a phosphated moiety. Washing and separating from the solid phase can be performed by a method known in the pertinent field. The deprotection can be performed in the same manner as in the above-mentioned liquid phase method.

In the liquid phase method, the progress of the reaction in each of the above-mentioned steps can be confirmed by a method similar to conventional liquid phase organic synthesis reaction. That is, the reaction can be traced by thin layer silica gel chromatography, high performance liquid chromatography or the like.

5'-3' synthesis

The production method of the present invention which is 5'-3' synthesis includes a step of adding an acid to a protected oligonucleotide having a phosphorothioate (PS), phosphate (PO) or H-phosphonate moiety to remove a temporary protecting group of the 3'-hydroxyl group or 3'-amino group, and solvolyzing a by-product with acylated 3'-hydroxyl group or 3'-amino group to perform deacylation.

The production method is explained by the following steps (3'): deprotection and step (4'): solvolysis.

The production method of the present invention which is 5'-3' synthesis also includes the following steps (1')-(4'):

(1') a step of condensing a nucleoside, nucleotide or oligonucleotide (a') wherein a 3'-hydroxyl group or 3'-amino group is not protected, and other groups are each optionally protected by a protecting group used for nucleic acid synthesis or bonded to a solid phase carrier, and nucleoside, nucleotide or oligonucleotide (b') wherein a 5'-hydroxyl group is modified by a method selected from a phosphoramidite method, an H-phosphonate method, a dihalophosphine method and an oxazaphospholidine method, the 3'-hydroxyl group or 3'-amino group is protected by a temporary protecting group that can be removed under acidic conditions, and other groups are each optionally protected by a protecting group used for nucleic acid synthesis to obtain a phosphite form or phosphorous acid diester (c') in which the 3'-hydroxyl group or 3'-amino group is protected by a temporary protecting group that can be removed under acidic conditions;

(2'): a step of (2'-1) sulfurizing the phosphite form or phosphorous acid diester (c') by adding a sulfurizing agent to obtain oligonucleotide (d'-1) having a phosphorothioated moiety in which the 3'-hydroxyl group or 3'-amino group is protected by a temporary protecting group that can be removed under acidic conditions, or (2'-2) oxidizing the phosphite form or phosphorous acid diester (c') by adding an oxidizing agent to obtain oligonucleotide (d'-2) having a phosphated moiety in which the 3'-hydroxyl group or 3'-amino group is protected by a temporary protecting group that can be removed under acidic conditions;

(3'): a step of (3'-1) adding an acid to the oligonucleotide (d'-1) having the phosphorothioated moiety to remove the temporary protecting group of the 3'-hydroxyl group or 3'-amino group, thereby obtaining a crude product of an oligonucleotide (e'-1) having a phosphorothioated moiety in which the 3'-hydroxyl group or 3'-amino group is not protected, or (3'-2) adding an acid to the oligonucleotide (d'-2) having a phosphated moiety to remove the temporary protecting group of the 3'-hydroxyl group or 3'-amino group, thereby obtaining a crude product of an oligonucleotide (e'-2) having a phosphated moiety in which the 3'-hydroxyl group or 3'-amino group is not protected; and (4'): a step of (4'-1) deacylating by solvolysis the oligonucleotide having a phosphorothioated moiety having an acylated 3'-hydroxyl group or 3'-amino group, which is contained in a crude product of the oligonucleotide (e'-1) having the phosphorothioated moiety, or (4'-2) deacylating by solvolysis the oligonucleotide having an acylated 3'-hydroxyl group or 3'-amino group contained in a crude product of the oligonucleotide (e'-2) having the phosphated moiety.

The oligonucleotide chain can be elongated by repeating the cycle of steps (1')-(4').

Explanation of the production method of the present invention which is 5'-3' synthesis is basically the same as the explanation of the above-mentioned production method of the present invention which is 3'-5' synthesis except that an oligonucleotide (e'-1) having a phosphorothioated moiety or oligonucleotide (e'-2) having a phosphated moiety in which the 3'-hydroxyl group or 3'-amino group is not protected is produced using a nucleoside, nucleotide or oligonucleotide (a') wherein a 3'-hydroxyl group or 3'-amino group is not protected, and other groups are each optionally protected by a protecting group used for nucleic acid synthesis or bonded to a solid phase carrier, and a nucleoside, nucleotide or oligonucleotide (b') wherein a 5'-hydroxyl group is modified by a method selected from a phosphoramidite method, an H-phosphonate method, a dihalophosphine method and an oxazaphospholidine method, the 3'-hydroxyl group or 3'-amino group is protected by a temporary protecting group that can be removed under acidic conditions, and other groups are each optionally protected by a protecting group used for nucleic acid synthesis. In other words, the explanations of steps (1')-(4'), nucleoside, nucleotide or oligonucleotide (a'), nucleoside, nucleotide or oligonucleotide (b'), phosphite form or phosphorous acid diester (c'), oligonucleotide (d'-1) having a phosphorothioated moiety or oligonucleotide (d'-2) having a phosphated moiety, and oligonucleotide (e'-1) having a phosphorothioated moiety or oligonucleotide (e'-2) having a phosphated moiety are basically the same as the explanations of the aforementioned steps (1)-(4), nucleoside, nucleotide or oligonucleotide (a), nucleoside, nucleotide or oligonucleotide (b), phosphite form or phosphorous acid diester (c), oligonucleotide (d-1) having a phosphorothioated moiety or oligonucleotide (d-2) having a phosphated moiety, and oligonucleotide (e-1) having a phosphorothioated moiety or oligonucleotide (e-2) having a phosphated moiety except that the embodiments of the protection of the 3'-hydroxyl group or 3'amino group and 5'-hydroxyl group and the like are exchanged. The difference between the 5'-3'synthesis and the 3'-5'synthesis is explained below.

Step (1') (Condensation)

In the nucleoside, nucleotide or oligonucleotide (b') to be used in this step, the 5'-hydroxyl group is modified by a method selected from a phosphoramidite method, an H-phosphonate method, a dihalophosphine method and an oxazaphospholidine method, the 3'-hydroxyl group or 3'-amino group is protected by a temporary protecting group that can be removed under acidic conditions, and other groups are each optionally protected by a protecting group used for nucleic acid synthesis. The explanation of the temporary protecting group of the hydroxyl group is the same as that in step (1).

Examples of the temporary protecting group of amino group include trityl group, monomethoxytrityl group, dimethoxytrityl group and the like. Of these, trityl group and monomethoxytrityl group are preferable.

In a preferred embodiment of this step, a nucleoside, nucleotide or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are each optionally further protected by a protecting group used for nucleic acid synthesis, or a substituted nucleotide or oligonucleotide (a1') wherein a 3'-hydroxy group is not protected, one OH of a 5'-terminal phosphate group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are each optionally further protected by a protecting group used for nucleic acid synthesis, and a nucleoside, nucleotide or oligonucleotide (b') wherein a 5'-hydroxy is modified by a method selected from a phosphoramidite method, an H-phosphonate method, a dihalophosphine method and an oxazaphospholidine method, a 3'-hydroxy group is protected by a temporary protecting group removable under acidic conditions, and other groups are each optionally further protected by a protecting group selected from protecting groups unremovable under acidic conditions but removable under basic conditions and protecting groups used for nucleic acid synthesis are used.

In a more preferred embodiment of this step, a nucleotide or oligonucleotide (a1') wherein a 3'-hydroxy group is not protected, one OH of a 5'-terminal phosphate group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are each optionally further protected by a protecting group used for nucleic acid synthesis, and a nucleoside or oligonucleotide (b') wherein a 5'-hydroxy is modified by a method selected from a phosphoramidite method, an H-phosphonate method, a dihalophosphine method and an oxazaphospholidine method, a 3'-hydroxy group is protected by a temporary protecting group removable under acidic conditions, and other groups are each optionally further protected by a protecting group selected from protecting groups unremovable under acidic conditions but removable under basic conditions and protecting groups used for nucleic acid synthesis are used.

In a more preferable another embodiment of this step, a nucleoside or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are each optionally further protected by a protecting group used for nucleic acid synthesis, and a nucleoside or oligonucleotide (b') wherein a 5'-hydroxy is modified by a method selected from a phosphoramidite method, an H-phosphonate method, a dihalophosphine method and an oxazapholidine method, a 3'-hydroxy group is protected by a temporary protecting group removable under acidic conditions, and other groups are each optionally further protected by a protecting group used for nucleic acid synthesis are used.

The condensation between the 3'-hydroxyl group possessed by the nucleoside, nucleotide or oligonucleotide (a') or nucleotide or oligonucleotide (a1'), and the 5'-hydroxyl group modified by a method selected from a phosphoramidite method, an H-phosphonate method, a dihalophosphine method and an oxazapholidine method and possessed by the nucleoside, nucleotide or oligonucleotide (b') can be performed in the same manner as in step (1). Therefore, the explanation of the condensation in step (1') is the same as that in step (1) except that the "nucleoside, nucleotide or oligonucleotide (a) or nucleotide or oligonucleotide (a1)" is replaced by the "nucleoside, nucleotide or oligonucleotide (a') or nucleotide or oligonucleotide (a1')" and the "nucleoside, nucleotide or oligonucleotide (b)" is replaced by the "nucleoside, nucleotide or oligonucleotide (b')".

The condensation between the 3'-amino group possessed by the nucleoside, nucleotide or oligonucleotide (a') or nucleotide or oligonucleotide (a1'), and the 5'-hydroxyl group modified by a method selected from a phosphoramidite method, an H-phosphonate method, a dihalophosphine method and an oxazapholidine method and possessed by the nucleoside, nucleotide or oligonucleotide (b') can also be performed in the same manner as in step (1). Therefore, the explanation of the condensation in step (1') is the same as that in step (1) except that the "nucleoside, nucleotide or oligonucleotide (a) or nucleotide or oligonucleotide (a1)" is replaced by the "nucleoside, nucleotide or oligonucleotide (a') or nucleotide or oligonucleotide (a1')" and the "nucleoside, nucleotide or oligonucleotide (b)" is replaced by the "nucleoside, nucleotide or oligonucleotide (b')".

Examples of the nucleoside, nucleotide or oligonucleotide (a') include a compound represented by the following formula (a-I') (i.e., nucleoside or oligonucleotide).

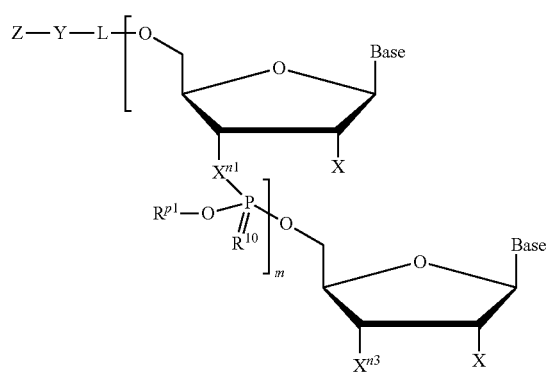

(a-I')

wherein
m, Base in the number of m+1, X in the number of m+1, $R^{10}$ in the number of m, $R^{p1}$ in the number of m, L, Y and Z are each independently as defined above;

$X^{n1}$ in the number of m are each independently an oxygen atom or NH; and $X^{n3}$ is a hydroxy group or an amino group.

In the formula (a-I'), $X^{n1}$ in the number of m is preferably an oxygen atom.

In the formula (a-I'), $X^{n3}$ is preferably a hydroxy group.

In the formula (a-I'), $R^{p1}$ in the number of m are preferably each independently a group represented by —CH$_2$CH$_2$WG.

Explanations of other symbols in the formula (a-I') are as mentioned above.

Compound (a-I') is preferably a compound represented by the following formula (a-i') (definition and explanation of the symbols in the following formula are as mentioned above).

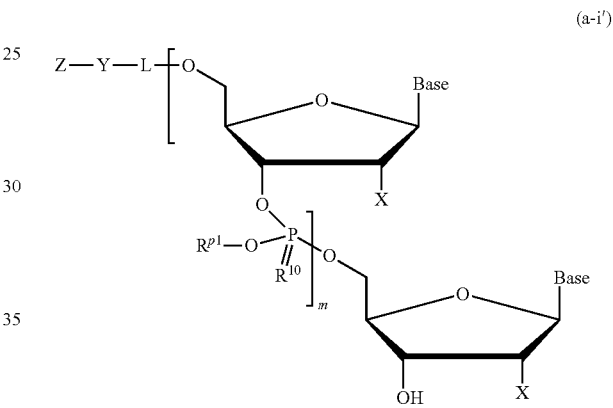

(a-i')

In compounds (a-i'), a compound represented by the formula (a-II') (i.e., nucleoside or oligonucleotide) is preferable (definition and explanation of the symbols in the following formula are as mentioned above).

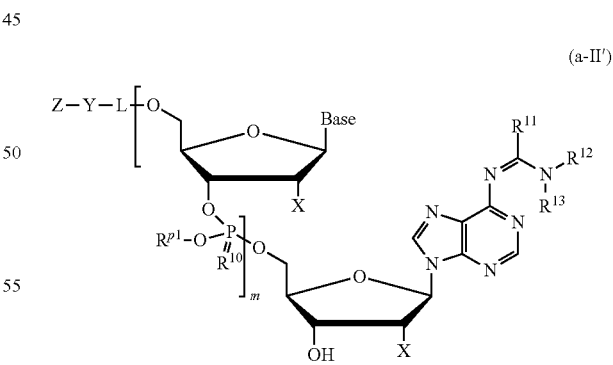

(a-II')

In the formula (a-II'), $R^{p1}$ in the number of m are preferably each independently a group represented by —CH$_2$CH$_2$WG.

In the formula (a-II'), m is preferably 0.

Explanations of other symbols in the formula (a-II') are as mentioned above.

In compounds (a-II'), a compound represented by the following formula (a-III') (i.e., nucleoside) is preferable (definition and explanation of the symbols in the following formula are as mentioned above).

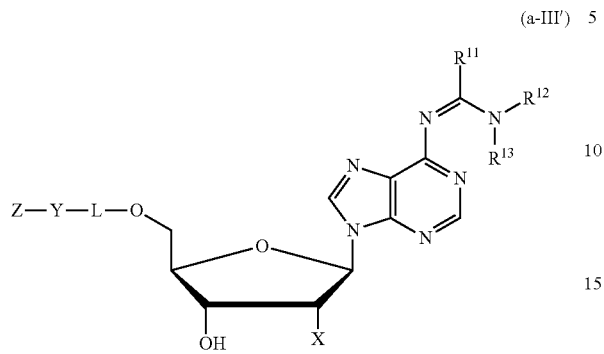
(a-III')

In compounds (a-I'), a compound represented by the following formula (a-IV') (i.e., nucleoside or oligonucleotide) is preferable (definition and explanation of the symbols in the following formula are as mentioned above).

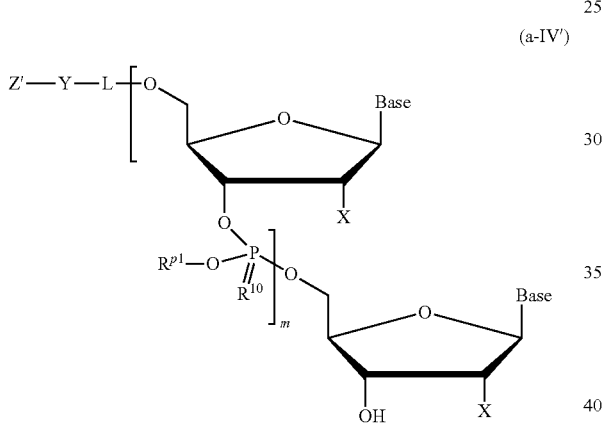
(a-IV')

In the formula (a-IV'), $R^{p1}$ in the number of m are preferably each independently a group represented by —$CH_2CH_2WG$.

In the formula (a-IV'), m is preferably 0.

Explanations of other symbols in the formula (a-IV') are as mentioned above.

In compounds (a-IV'), a compound represented by the following formula (a-V') (i.e., nucleoside) is preferable (definition and explanation of the symbols in the following formula are as mentioned above).

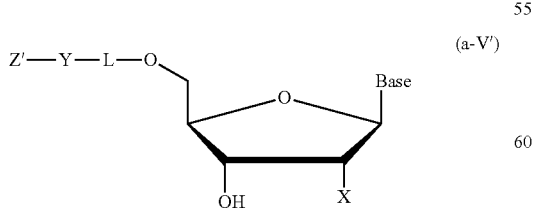
(a-V')

Examples of the nucleoside, nucleotide or oligonucleotide (a') include a compound represented by the following formula (a-VI') (i.e., nucleoside or oligonucleotide).

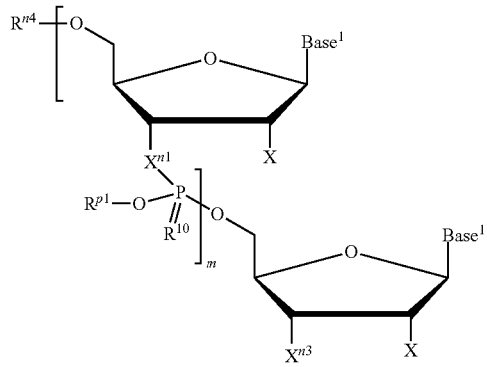
(a-VI')

wherein
at least one of Base$^1$ in the number of m+1 is a nucleic acid base protected by -L-Y—Z, and the rest is an optionally protected nucleic acid base;
$X^{n1}$ in the number of m are each independently an oxygen atom or NH;
$X^{n3}$ is a hydroxy group or an amino group;
$R^{n4}$ is a hydroxy-protecting group;
m, X in the number of m+1, $R^{10}$ in the number of m, $R^{p1}$ in the number of m, L, Y and Z are each independently as defined above.

In the formula (a-VI'), $X^{n1}$ in the number of m are preferably oxygen atoms.

In the formula (a-VI'), $X^{n3}$ is preferably a hydroxy group.

In the formula (a-VI'), $R^{p1}$ in the number of m are preferably each independently a group represented by —$CH_2CH_2WG$.

In the formula (a-VI'), explanations of other symbols are as mentioned above.

Compound (a-VI') is preferably a compound represented by the following formula (a-vi') (definition and explanation of the symbols in the following formula are as mentioned above).

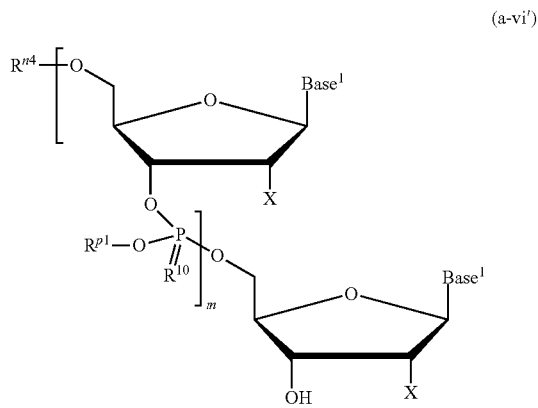
(a-vi')

Examples of the nucleotide or oligonucleotide (a1') include a compound represented by the following formula (a-VII').

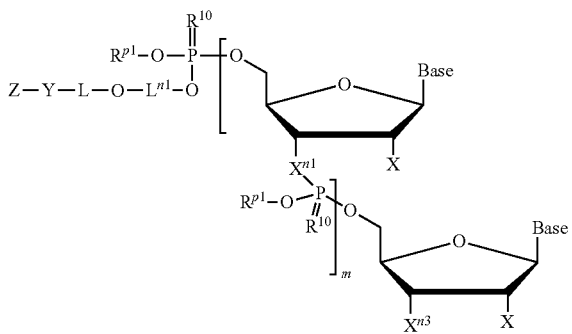

(a-VII')

wherein
X$^{n1}$ in the number of m are each independently an oxygen atom or NH;
X$^{n3}$ is a hydroxy group or an amino group;
L$^{n1}$ is an organic group;
m, Base in the number of m+1, X in the number of m+1, R$^{10}$ in the number of m+1, R$^{p1}$ in the number of m+1, L, Y and Z are each independently as defined above.

In the formula (a-VII'), X$^{n3}$ is preferably a hydroxy group.

In the formula (a-VII'), R$^{p1}$ in the number of m+1 are preferably each independently a group represented by —CH$_2$CH$_2$WG.

Explanations of other symbols in the formula (a-VII') are as mentioned above.

Compound (a-VII') is preferably a compound represented by the following formula (a-vii') (definition and explanation of the symbols in the following formula are as mentioned above).

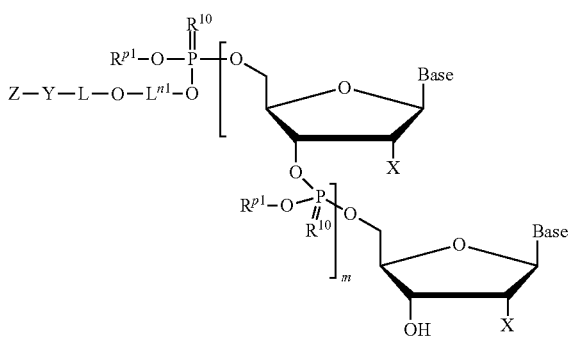

(a-vii')

The nucleoside, nucleotide or oligonucleotide (a') or nucleotide or oligonucleotide (a1') used in this step is preferably compound (a-I'), compound (a-VI') or compound (a-VII'), more preferably compound (a-i'), compound (a-vi') or compound (a-vii'), further preferably compound (a-i') or compound (a-vii'), particularly preferably compound (a-vii').

Examples of the nucleoside, nucleotide or oligonucleotide (b') include a compound represented by the following formula (b-I') (i.e., nucleoside or oligonucleotide).

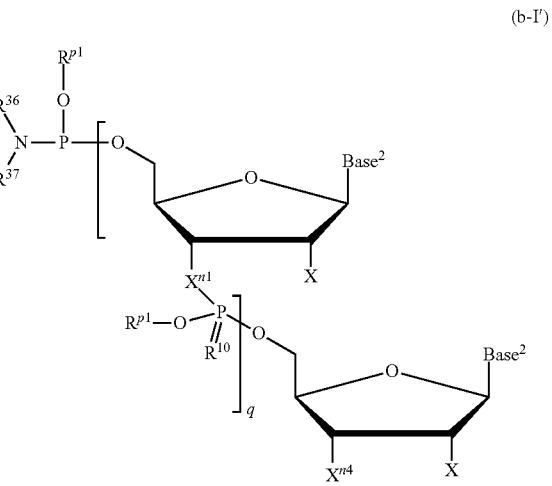

(b-I')

wherein
Base$^2$ in the number of q+1 are each independently a nucleic acid base optionally protected by a protecting group selected from -L-X—Z and protecting groups used for nucleic acid synthesis;
X$^{n1}$ in the number of q are each independently an oxygen atom or NH;
X$^{n4}$ is a hydroxy group or an amino group, each of which is protected by a temporary protecting group removable under acidic conditions;
q, X in the number of q+1, R$^{p1}$ in the number of q+1, R$^{10}$ in the number of q, R$^{36}$ and R$^{37}$ are each independently as defined above.

Explanations of the temporary protecting group of hydroxy group and the temporary protecting group of amino group in the formula (b-I') are as mentioned above. X$^{n4}$ is preferably a hydroxy group protected by a temporary protecting group removable under acidic conditions.

In the formula (b-I'), R$^{p1}$ in the number of q+1 are preferably each independently a group represented by —CH$_2$CH$_2$WG.

In the formula (b-I'), explanations of other symbols are as mentioned above.

Compound (b-I') is preferably a compound represented by the following formula (b-i') (definition and explanation of the symbols in the following formula are as mentioned above).

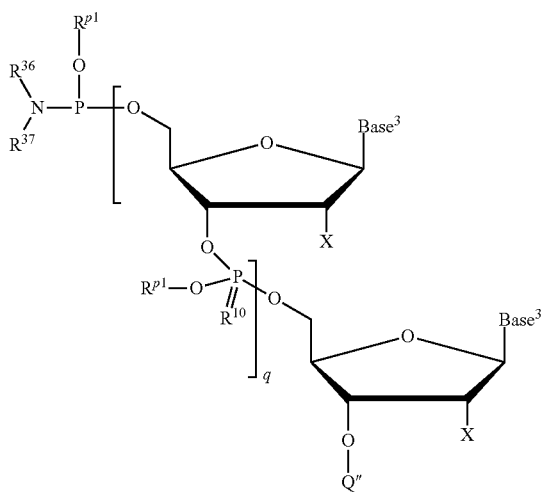

(b-i')

Explanations of the aforementioned compound (a-I')-compound (a-vii'), compounds (b-I') and (b-i') are basically the same as those of the aforementioned compound (a-I)-compound (a-vii), compounds (b-I) and (b-i) except that the protection embodiments of the 3'-hydroxy group and the 5'-hydroxy group and the like are interchanged.

A combination of the nucleoside, nucleotide or oligonucleotide (a') or nucleotide or the oligonucleotide (a1'), and the nucleoside, nucleotide or oligonucleotide (b') used in this step is
preferably a combination of compound (a-I'), compound (a-VI') or compound (a-VII') and compound (b-I'),
more preferably a combination of compound (a-i'), compound (a-vi') or compound (a-vii') and compound (b-i'),
further preferably a combination of compound (a-i') or compound (a-vii') and compound (b-i'),
particularly preferably a combination of compound (a-vii') and compound (b-i').

The amount of the nucleoside, nucleotide or oligonucleotide (b') to be used in this step in the case of the liquid phase method is, for example, 1 to 10 mol, preferably 1 to 5 mol, per 1 mol of the amount of use of the nucleoside, nucleotide or oligonucleotide (a') in this step and, in the case of the solid phase method, it is, for example, 1 to 20 mol, preferably 1 to 10 mol, per 1 mol of the amount of use of the nucleoside, nucleotide or oligonucleotide (a') in this step.

The reaction temperature in this step is not particularly limited as long as the reaction proceeds. In the liquid phase method, it is preferably 0° C. to 100° C., more preferably 20° C. to 50° C. In the solid phase method, it is preferably 10° C. to 40° C., more preferably 20° C. to 30° C. The reaction time varies depending on the kind of the starting material to be used, reaction temperature and the like. In the liquid phase method, it is, for example, 5 min to 24 hr and, in the solid phase method, it is, for example, 1 min to 30 min.

Step (2'): (2'-1) (Sulfurization)

In this step, a phosphite form or phosphorous acid diester (c') in which a 3'-hydroxyl group or 3'-amino group is protected with a temporary protecting group that can be removed under acidic conditions is reacted with a sulfurizing agent to convert the phosphite bond or phosphorous acid diester bond thereof to a phosphorothioate bond, thus obtaining oligonucleotide (d'-1) having a phosphorothioated moiety in which the 3'-hydroxyl group or 3'-amino group is protected by a temporary protecting group that can be removed under acidic conditions. Only one kind of the sulfurizing agent may be used, or two or more kinds thereof may be used in combination.

The sulfurizing agent to be used in this step is not particularly limited as long as it is capable of converting a phosphite bond or a phosphorous acid diester bond to a phosphorothioate bond. 5-[(N,N-dimethylaminomethylidene)amino]-3H-1,2,4-dithiazole-3-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), dipentamethylenethiuram tetrasulfide, 5-phenyl-3H-1,2,4-dithiazol-3-one (POS), 3-amino-1,2,4-dithiazole-5-thione (ADTT, xanthan hydride), and sulfur are preferable.

Since a good reaction can proceed, 5-[(N,N-dimethylaminomethylidene)amino]-3H-1,2,4-dithiazole-3-thione (DDTT), 3H-1,2-benzodithiol-3-one-1,1-dioxide (Beaucage reagent), 3H-1,2-benzodithiol-3-one, phenylacetyl disulfide (PADS), and 5-phenyl-3H-1,2,4-dithiazol-3-one (POS) are more preferable, 5-[(N,N-dimethylaminomethylidene)amino]-3H-1,2,4-dithiazole-3-thione (DDTT), 3H-1,2-benzodithiol-3-one-1,1-dioxide (Beaucage reagent), and 5-phenyl-3H-1,2,4-dithiazol-3-one (POS) are further preferable, and 5-[(N,N-dimethylaminomethylidene)amino]-3H-1,2,4-dithiazole-3-thione (DDTT) and 5-phenyl-3H-1,2,4-dithiazol-3-one (POS) are particularly preferable. Such sulfurizing agent can be used by diluting with a suitable solvent at a concentration of 0.05 to 2 M. Such diluent solvent is not particularly limited as long as it is inert to the reaction and, for example, dichloromethane, acetonitrile, pyridine or a mixed solvent of any of these can be mentioned.

The amount of the sulfurizing agent to be used is, for example, 1 to 50 mol, preferably 1 to 10 mol, per 1 mol of a phosphite form or phosphorous acid diester (c) in the case of the liquid phase method. In the case of solid phase method, for example, 1 to 100 mol, preferably 1 to 20 mol.

The reaction temperature is not particularly limited as long as the reaction proceeds. In the liquid phase method, it is preferably 0° C. to 100° C., more preferably 20° C. to 50° C. In the solid phase method, it is preferably 10° C. to 40° C., more preferably 20° C. to 30° C. The reaction time varies depending on the kind of the phosphite form or phosphorous acid diester (c'), the kind of the sulfurizing agent to be used, reaction temperature and the like. In the liquid phase method, it is, for example, 1 min to 3 hr and, in the solid phase method, it is, for example, 1 min to 30 min.

Step (2'): (2'-2) (Oxidation)

In this step, a phosphite form or phosphorous acid diester (c') in which the 3'-hydroxyl group or 3'-amino group is protected by a temporary protecting group that can be removed under acidic conditions is reacted with an oxidizing agent to convert the phosphite bond or phosphorous acid diester bond to a phosphate bond, whereby oligonucleotide (d'-2) having a phosphated moiety in which the 3'-hydroxyl group or 3'-amino group is protected by a temporary protecting group that can be removed under acidic conditions is obtained. Only one kind of an oxidizing agent may be used, or two or more kinds thereof may be used in combination.

The oxidizing agent to be used in this step is not particularly limited as long as it is capable of converting a phosphite bond or a phosphorous acid diester bond to a phosphate bond. Since a good reaction can proceed, iodine is preferable.

Such oxidizing agent can be used by diluting with a suitable solvent. The dilution solvent is not particularly limited as long as it is inert to the reaction. For example, pyridine, water, and any mixed solvent of these can be mentioned, and a mixed solvent of pyridine and water is preferable. Pyridine is used at 3 to 10 mol, preferably 4 to 6 mol, per 1 mol of the oxidizing agent, and water is used at 1 to 5 mol, preferably 2 to 4 mol, per 1 mol of the oxidizing agent.

The amount of the oxidizing agent to be used is, for example, 1 to 50 mol, preferably 1 to 10 mol, per 1 mol of the phosphite form or phosphorous acid diester (c') in the liquid phase method. In the solid phase method, it is, for example, 1 to 100 mol, preferably 1 to 20 mol.

The reaction temperature is not particularly limited as long as the reaction proceeds. In the liquid phase method, it is preferably 0° C. to 100° C., more preferably 20° C. to 50° C. In the solid phase method, it is preferably 10° C. to 40° C., more preferably 20° C. to 30° C. The reaction time varies depending on the kind of the phosphite form or phosphorous acid diester (c'), the kind of the oxidizing agent to be used, reaction temperature and the like. In the liquid phase method, it is, for example, 1 min to 3 hr and, in the solid phase method, it is, for example, 1 min to 30 min.

Step (3'): (3'-1) (Removal of Temporary Protecting Group of Oligonucleotide Having Phosphorothioated Moiety), or (3'-2) (Removal of Temporary Protecting Group of Oligonucleotide Having Phosphated Moiety)

In this step, the temporary protecting group of oligonucleotide (d'-1) having a phosphorothioated moiety is removed by an acid to obtain a crude product of an oligonucleotide (e'-1) having a phosphorothioated moiety in which the 3'-hydroxyl group or 3'-amino group is not protected. In this step, moreover, the temporary protecting group of oligonucleotide (d'-2) having a phosphated moiety is removed by an acid to obtain a crude product of an oligonucleotide (e'-2) having a phosphated moiety in which the 3'-hydroxyl group or 3'-amino group is not protected. Only one kind of acid may be used, or two or more kinds thereof may be used in combination.

Explanation of the removal of the temporary protecting group of hydroxy group is the same as that in step (1).

The acid to be used for removal of the temporary protecting group of amino group is not particularly limited as long as good deprotection can be achieved, and examples thereof include carboxylic acids such as trifluoroacetic acid, dichloroacetic acid, trichloroacetic acid, acetic acid and the like, sulfonic acids such as trifluoromethanesulfonic acid, methanesulfonic acid, p-toluenesulfonic acid and the like, phosphonic acid, phosphoric acid and the like. To solve the problem that the deprotected 3'-hydroxyl group or 3'-amino group is acylated in the deprotection step, at least a carboxylic acid capable of acylating a hydroxyl group is preferably contained, and at least trifluoroacetic acid, dichloroacetic acid or trichloroacetic acid is more preferably contained. These acids may be diluted with the aforementioned non-polar solvents. The amount of the acid to be used for removal of the temporary protecting group of amino group is, for example, 1 to 100 mol, preferably 1 to 40 mol, in the liquid phase method and, for example, 1 to 200 mol, preferably 1 to 80 mol, in the solid phase method, per 1 mol of oligonucleotide (d'-1) having a phosphorothioated moiety or 1 mol of oligonucleotide (d'-2) having a phosphated moiety.

The reaction temperature for removal of the temporary protecting group of amino group is not particularly limited as long as the reaction proceeds. In the liquid phase method, it is preferably −10° C. to 50° C., more preferably 0° C. to 40° C. In the solid phase method, it is preferably 10° C. to 50° C., more preferably 20° C. to 30° C. The reaction time of the temporary protecting group of amino group varies depending on the kind of the oligonucleotide (d'-1) having a phosphorothioated moiety or oligonucleotide (d'-2) having a phosphated moiety to be used, the kind of the acid and the kind of the non-polar solvent, reaction temperature and the like. In the liquid phase method, it is, for example, 5 min to 5 hr and, in the solid phase method, it is, for example, 1 min to 30 min.

Step (4'): (4'-1) (Solvolysis of Oligonucleotide Having a Phosphorothioated Moiety), or (4-2) (Solvolysis of Oligonucleotide Having a Phosphated Moiety)

In this step, an oligonucleotide having a phosphorothioated moiety with an acylated 3'-hydroxyl group or 3'-amino group, which is contained in a crude product of an oligonucleotide (e'-1) having the phosphorothioated moiety, is deacylated by solvolysis. In this step, moreover, an oligonucleotide having a phosphated moiety with an acylated 3'-hydroxyl group or 3'-amino group, which is contained in a crude product of an oligonucleotide (e'-2) having the phosphated moiety, is deacylated by solvolysis.

The "acylation" in this step means a reaction of the acid, which is added in the previous step (3'-1) or (3'-2) to remove the temporary protecting group of the 3'-hydroxyl group or 3'-amino group, with the 3'-hydroxyl group or 3'-amino group. As a result of the reaction, R—C(=O)— binds to the 3'-position oxygen atom or nitrogen atom when the acid is carboxylic acid, R—S(=O)$_2$— binds to the 3'-position oxygen atom or nitrogen atom when the acid is sulfonic acid, H—P(=O) (OH)— binds to the 3'-position oxygen atom or nitrogen atom when the acid is phosphonic acid, and H—P(=O)$_2$— binds to the 3'-position oxygen atom or nitrogen atom when the acid is phosphoric acid. On the other hand, the "deacylation" in this step means that the generated acylated product becomes a 3'-hydroxyl group or 3'-amino group by solvolysis in this step.

This step is preferably performed under basic conditions that prevent the cyanoalkyl group (e.g., cyanoethyl group), alkoxycarbonylalkyl group (e.g., ethoxycarbonylethyl group), halogenophenyl group (2-chlorophenyl group) and the like bonded to the oxygen atom of the phosphorothioated moiety or phosphated moiety from falling off. Particularly, in the case of a basically unstable cyanoalkyl group (e.g., cyanoethyl group), it is desirable to prevent the cyanoalkyl group (e.g., cyanoethyl group) from falling off.

The solvent to be used in this step is not particularly limited as long as it can deacylate an oligonucleotide having a phosphorothioated moiety with an acylated 3'-hydroxyl group or 3'-amino group. The solvent to be used in this step is not particularly limited as long as it can deacylate an oligonucleotide having a phosphated moiety with an acylated 3'-hydroxyl group or 3'-amino group. It is preferably a mixture of a base and a nucleophilic substance. As the base, an organic base is preferable and, for example, pyridine, collidine, lutidine and the like can be mentioned, and pyridine is preferable. As the nucleophilic substance, water and alcohols are preferable. For example, water, methanol, ethanol and the like can be mentioned, and water and methanol are preferable. The mixture of a base and a nucleophilic substance is preferably a mixture of pyridine and water, a mixture of pyridine and methanol, a mixture of pyridine and ethanol, a mixture of collidine and water, a mixture of collidine and methanol, a mixture of collidine and ethanol, a mixture of lutidine and water, a mixture of lutidine and methanol, or a mixture of lutidine and ethanol, and a mixture of pyridine and water, a mixture of pyridine and methanol, and pyridine and ethanol are more preferable.

The amount of the base to be used in this step varies depending on the kind of the base to be used. In the liquid phase method, when this step is performed in one pot without purification after the deprotection step, or in the case of the solid phase method, the acid used in the deprotection remains in the reaction solution, which requires more bases. For this reason, in the liquid phase method (one-pot method) and the solid phase method, 1 to 10 equivalents, preferably 3 to 5 equivalents, of the base are required with respect to the amount of the acid used. On the other hand, in a method other than the above-mentioned solid phase method and the liquid phase method (one-pot method), 1 to 5 mol, preferably 1 to 3 mol, of the base is required per 1 mol of a crude product of the oligonucleotide (e'-1) having a phosphorothioated moiety or a crude product of oligonucleotide (e'-2) having a phosphated moiety.

The reaction temperature in this step is not particularly limited as long as the reaction proceeds. In the liquid phase method, it is preferably –0° C. to 50° C., more preferably 5° C. to 30° C. In the solid phase method, it is preferably 5° C. to 40° C., more preferably 10° C. to 30° C. The reaction time varies depending on the kind of a crude product of the oligonucleotide (e'-1) having a phosphorothioated moiety or a crude product of oligonucleotide (e'-2) having a phosphated moiety and the solvent to be used, reaction temperature and the like. In the liquid phase method, it is, for example, 10 min to 24 hr and, in the solid phase method, it is, for example, 1 min to 30 min.

Oligonucleotide

The oligonucleotide (e-1) or (e'-1) having a phosphorothioated moiety, the oligonucleotide (e-2) or (e'-2) having a phosphated moiety, which are obtained by solid-liquid separation or extraction, or oligonucleotide having an unprotected phosphorothioated moiety or oligonucleotide having an unprotected phosphated moiety which is obtained by deprotection and isolation can also be led to a desired derivative by further applying an organic synthesis reaction. The oligonucleotide having a phosphorothioated moiety or oligonucleotide having a phosphated moiety obtained by the production method of the present invention can be used for various applications such as pharmaceutical products (RNA, DNA, oligonucleic acid medicine, etc.) for human or animal, functional food, food for specified health uses, food, chemical product, polymer material for living body or industrial use, and the like.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless otherwise specified. In the present specification, when amino acid and the like are indicated by abbreviation, each indication is based on the abbreviation of the IUPAC-IUB Commission on Biochemical Nomenclature or conventional abbreviation in the art.

The meanings of the abbreviations used in the below-mentioned Examples and the like are as described below.

In addition, 2'-OMe-C-CE phosphoramidite and the like used in the below-mentioned Examples and the like are sometimes generically referred to as phosphoramidite monomer in the following.

SUC: succinyl
TOB: 3,4,5-tris(octadecyloxy)benzyloxy
Piv-TOB: 3,4,5-tris(octadecyloxy)benzyl pivalate
DDTT: 5-[(N,N-dimethylaminomethylidene)amino]-3H-1,2,4-dithiazole-3-thione
POS: 5-phenyl-3H-1,2,4-dithiazol-3-one
PADS: phenylacetyl disulfide
DMTr: 4,4'-dimethoxytrityl
LC-TOF MS: liquid chromatograph-time-of-flight mass spectrometer
DBU: 1,8-diazabicyclo[5.4.0]-7-undecene
PivCl: pivaloyl chloride
2'-OMe-C-CE phosphoramidite: 5'-O-(4,4'-dimethoxytrityl)-$N^4$-benzoyl-2'-O-methyl-cytidine-3'-[O-(2-cyanoethyl)-(N,N-diisopropyl)]-phosphoramidite
2'-OMe-G-CE phosphoramidite: 5'-O-(4,4'-dimethoxytrityl)-$N^2$-isobutyryl-2'-O-methyl-guanosine-3'-[O-(2-cyanoethyl)-(N,N-diisopropyl)]-phosphoramidite
5-Me-dC(Bz)-CE phosphoramidite: 5'-O-(4,4'-dimethoxytrityl)-$N^4$-benzoyl-2'-deoxy-5-methylcytidine-3'-[O-(2-cyanoethyl)-(N,N-diisopropyl)]-phosphoramidite
dG-CE phosphoramidite: 5'-O-(4,4'-dimethoxytrityl)-$N^2$-isobutyryl-deoxyguanosine-3'-[O-(2-cyanoethyl)-(N,N-diisopropyl)]-phosphoramidite
2'-O-TBDMS-C(Ac)-CE phosphoramidite: 5'-O-(4,4'-dimethoxytrityl)-$N^4$-acetyl-2'-O-(tert-butyldimethylsilyl)-cytidine-3'-[O-(2-cyanoethyl)-(N,N-diisopropyl)]-phosphoramidite
LNA-A(Bz)-CE phosphoramidite: 5'-O-(4,4'-dimethoxytrityl)-$N^6$-benzoyl-2'-O,4'-C-methylene-adenosine-3'-[O-(2-cyanoethyl)-(N,N-diisopropyl)]-phosphoramidite
2'-F—C(Bz)-CE phosphoramidite: 5'-O-(4,4'-dimethoxytrityl)-$N^4$-benzoyl-2'-deoxy-2'-fluoro-cytidine-3'-[O-(2-cyanoethyl)-(N,N-diisopropyl)]-phosphoramidite
dT-H-phosphonate TEA salt: 5'-O-(4,4'-dimethoxytrityl)-deoxythymidine-3'-H-phosphonate, triethylamine salt
HO-dT-SUC-TOB: deoxythymidine 3'-yl 3,4,5-tris(octadecyloxy)benzyl succinate
HO-T-SUC-TOB: deoxythymidin-3'-yl 3,4,5-tris(octadecyloxy)benzyl succinate
HO-CmT-SUC-TOB: $N^4$-benzoyl-2'-O-methyl-cytidine-3'-[O-(2-cyanoethyl)]phosphorothionyl deoxythymidin-3'-yl-[3,4,5-tris(octadecyloxy)benzyl] succinate
HO-GmCmT-SUC-TOB: $N^2$-isobutyryl-2'-O-methyl-guanosine 3'-[O-(2-cyanoethyl)]phosphoryl $N^4$-benzoyl-2'-O-methyl-cytidine 3'-[O-(2-cyanoethyl)]phosphorothionyl deoxythymidin-3'-yl-[3,4,5-tris (octadecyloxy) benzyl] succinate)
HO-2'-OMe-U—SUC-TOB: 2'-O-methyl-uridin-3'-yl 3,4,5-tris(octadecyloxy)benzyl succinate
HO-Um-SUC-TOB: 2'-O-methyl-uridin-3'-yl 3,4,5-tris(octadecyloxy)benzyl succinate
HO-CmUm-SUC-TOB: $N^4$-benzoyl-2'-O-methyl-cytidine-3'-[O-(2-cyanoethyl)]phosphorothionyl 2'-O-methyl-uridin-3'-yl-[3,4,5-tris(octadecyloxy)benzyl] succinate
HO-GUm-SUC-TOB: $N^2$-isobutyryl-deoxyguanosine 3'-[O-(2-cyanoethyl)]phosphorothionyl 2'-O-methyl-uridin-3'-yl-[3,4,5-tris(octadecyloxy)benzyl]succinate
HO-ALT-SUC-TOB: $N^6$-benzoyl-2'-O,4'-C-methylene-adenosine-3'-[O-(2-cyanoethyl)]phosphorothionyl deoxythymidin-3'-yl-[3,4,5-tris(octadecyloxy)benzyl]succinate
HO—C$_f$A$_L$T-SUC-TOB: $N^4$-benzoyl-2'-deoxy-2'-fluoro-cytidine-3'-[O-(2-cyanoethyl)]phosphorothionyl $N^6$-benzoyl-2'-O,4'-C-methylene-adenosine-3'-[O-(2-cyanoethyl)]phosphorothionyl deoxythymidin-3'-yl-[3,4,5-tris (octadecyloxy)benzyl]succinate
HO-rCC$_f$A$_L$T-SUC-TOB: $N^4$-acetyl-2'-O-(tert-butyldimethylsilyl)-cytidine-3'-[O-(2-cyanoethyl)]phosphorothionyl $N^4$-benzoyl-2'-fluoro-cytidine-3'-[O-(2-cyanoethyl)]

phosphorothionyl N[6]-benzoyl-2'-O,4'-C-methylene-adenosine-3'-[O-(2-cyanoethyl)]phosphorothionyl deoxythymidin-3'-yl-[3,4,5-tris(octadecyloxy)benzyl]succinate HO—(CH$_2$)$_2$—SUC-TOB: 3,4,5-tris(octadecyloxy)benzyl 2-hydroxyethyl succinate HO-A$_L$(CH$_2$)$_2$—SUC-TOB: N[6]-benzoyl-2'-O,4'-C-methylene-adenosine-3'-[O-(2-cyanoethyl)]phosphorothionyl ethyloxy-[3,4,5-tris(octadecyloxy)benzyl]succinate HO—C$_f$A$_L$ (CH$_2$)$_2$—SUC-TOB: N[4]-benzoyl-2'-deoxy-2'-fluoro-cytidine-3'-[O-(2-cyanoethyl)]phosphorothionyl N[6]-benzoyl-2'-O,4'-C-methylene-adenosine-3'-[O-(2-cyanoethyl)]phosphorothionyl ethyloxy-[3,4,5-tris(octadecyloxy)benzyl]succinate HO-rCC$_f$A$_L$(CH$_2$)$_2$—SUC-TOB: N[4]-acetyl-2'-O-(tert-butyldimethylsilyl)-cytidine-3'-[O-(2-cyanoethyl)]phosphorothionyl N[4]-benzoyl-2'-fluoro-cytidine-3'-[O-(2-cyanoethyl)]phosphorothionyl N[6]-benzoyl-2'-O,4'-C-methylene-adenosine-3'-[O-(2-cyanoethyl)]phosphorothionyl ethyloxy-[3,4,5-tris(octadecyloxy)benzyl]succinate HO-T$_H$T-SUC-TOB: deoxythymidine-3'-phosphonate deoxythymidin-3'-yl-[3,4,5-tris(octadecyloxy)benzyl]succinate HO-T$_{OH}$T-SUC-TOB: deoxythymidine-3'-phosphorothionyl deoxythymidin-3'-yl-[3,4,5-tris(octadecyloxy)benzyl]succinate In the following, the TOB-added compounds were synthesized according to the method described in WO 2012/157723, which is incorporated herein by reference in its entirety.

Reference Example 1

Under an argon atmosphere, HO-2'-OMe-U—SUC-TOB (251 mg, 200 µmol) and Piv-TOB (251 mg, 251 µmol) were placed in a 20-mL two-necked flask, and dissolved in dehydrated dichloromethane (10.0 mL) and dehydrated acetonitrile (1.0 mL) added thereto. Thereafter, 2'-OMe-C-CE phosphoramidite (518 mg, 600 µmol) and 5-benzylthio-1H-tetrazole (78.1 mg, 600 µmol) were successively added, and the mixture was stirred at room temperature for 1.0 hr. Successively, to the reaction solution was added 2,2,2-trifluoroethanol (219 µL, 3.0 mmol) and the mixture was stirred at room temperature for 30 min. 2,6-Xylidine (351 µL, 2.9 mmol) and DDTT (129 mg, 630 µmol) were successively added, and the mixture was stirred at room temperature for 1 hr. Thereafter, 2,3-dimethylfuran (316 µL, 3.0 mmol) and trifluoroacetic acid (459 µL, 6.0 mmol) were successively added, and the mixture was stirred at room temperature for 1.5 hr. Analysis of the reaction solution at the completion of the detritylation step revealed that it contained 0.97% of trifluoroacetylated oligonucleic acid. The reaction solution was divided into two: Example 1 and Comparative Example 1 described below.

Example 1: Sulfurization Reaction with DDTT, Followed by Detritylation, Solvolysis To a detritylation step solution containing elongated oligonucleic acid (38 µmol) synthesized in the above-mentioned Reference Example 1 were successively added collidine (318 µL, 2.4 mmol) and water (23.8 µL), and the mixture was stirred at room temperature for 2 hr. Analysis of the reaction solution revealed that the remaining amount of trifluoroacetylated oligonucleic acid was 0.004%. Thereafter, acetonitrile (5.7 mL) was added, the precipitated solid was filtered by suction with Kiriyama funnel, and dried to give dimer HO-CmUm-SUC-TOB as a white solid.

m/z(TOF-MS): Calcd. 1745.06, Found 1746.07[M+H]$^+$

The obtained dimer HO-CmUm-SUC-TOB (26.2 mg, 15 µmol) was dissolved in dehydrated dichloromethane (0.8 mL) and dehydrated acetonitrile (0.10 mL) added thereto. Thereafter, 2'-OMe-G-CE phosphoramidite (39.1 mg, 45 µmol) and 5-benzylthio-1H-tetrazole (8.7 mg, 45 µmol) were successively added, and the mixture was stirred at room temperature for 1.0 hr. Successively, to the reaction solution was added 2,2,2-trifluoroethanol (16.4 µL, 225 µmol) and the mixture was stirred at room temperature for 30 min. 2,6-Xylidine (26.3 µL, la 214 µmol) and DDTT (9.7 mg, 47 µmol) were successively added, and the mixture was stirred at room temperature for 1 hr. Analysis of the reaction solution revealed that the remaining starting material was 0.07%.

Comparative Example 1: Sulfurization Reaction with DDTT, Followed by Detritylation, Solvolysis Incomplete To a detritylation step solution containing elongated oligonucleic acid (38 µmol) synthesized in the above-mentioned Reference Example 1 were successively added collidine (159 µL, 1.2 mmol) and water (24 µL, 192 µmol), and the mixture was stirred at room temperature for 2 hr. Analysis of the reaction solution revealed that the remaining amount of trifluoroacetylated oligonucleic acid was 0.21%. Thereafter, acetonitrile (5.7 mL) was added, the precipitated solid was filtered by suction with Kiriyama funnel, and dried to give dimer HO-CmUm-SUC-TOB as a white solid.

m/z(TOF-MS): Calcd. 1745.06, Found 1746.07[M+H]$^+$

The obtained dimer HO-CmUm-SUC-TOB (26.2 mg, 15 µmol) was dissolved in dehydrated dichloromethane (0.8 mL) and dehydrated acetonitrile (0.10 mL) added thereto. Thereafter, 2'-OMe-G-CE phosphoramidite (39.1 mg, 45 µmol) and 5-benzylthio-1H-tetrazole (8.7 mg, 45 µmol) were successively added, and the mixture was stirred at room temperature for 1.0 hr. Successively, to the reaction solution was added 2,2,2-trifluoroethanol (16.4 µL, 225 µmol) and the mixture was stirred at room temperature for 30 min. 2,6-Xylidine (26.3 µL, 214 µmol) and DDTT (9.7 mg, 47 µmol) were successively added, and the mixture was stirred at room temperature for 1 hr. Analysis of the reaction solution revealed that the remaining starting material was 0.26%.

Example 2: Sulfurization Reaction with POS, Followed by Detritylation, Solvolysis The sulfurizing agent in Example 1 was changed from DDTT to POS, and one-pot oligonucleic acid synthesis in which 5-Me-dC(Bz)-CE phosphoramidite was extended to HO-dT-SUC-TOB (81 µmol) was performed in the same manner. Analysis of the reaction solution at the completion of the detritylation step revealed that it contained 7% of trifluoroacetylated oligonucleic acid. Thereafter, the reaction solution was divided into three, and each was used as solution A, solution B or solution C.

Solution A: Solvolysis with Pyridine and Methanol

To a detritylation step solution containing elongated oligonucleic acid (20 µmol) were successively added pyridine (603 µL, 7.5 mmol) and methanol (6.7 µL), and the mixture was stirred at room temperature for 1 hr. Analysis of the reaction solution revealed that the trifluoroacetylated oligonucleic acid content was 0.01%.

Solution B: Solvolysis with Collidine and Water

To a detritylation step solution containing elongated oligonucleic acid (20 μmol) were successively added collidine (252 μL, 1.9 mmol) and water (6.1 μL), and the mixture was stirred at room temperature for 1 hr. Analysis of the reaction solution revealed that the trifluoroacetylated oligonucleic acid content was 0.02%.

Solution C: Solvolysis with Collidine and Methanol

To a detritylation step solution containing elongated oligonucleic acid (20 μmol) were successively added collidine (207 μL, 1.6 mmol) and methanol (5.0 μL), and the mixture was stirred at room temperature for 1 hr. Analysis of the reaction solution revealed that the trifluoroacetylated oligonucleic acid content was 0.01%.

Example 3: Oxidation Reaction, Followed by Detritylation, Solvolysis

Under an argon atmosphere, HO-CmT-SUC-TOB (101 mg, 60 μmol) synthesized in the same manner as in Reference Example 1 and Example 1 except that HO-T-SUC-TOB was used instead of HO-2'-OMe-U—SUC-TOB in Reference Example 1 was placed in a 20-mL two-necked flask, and dissolved in dehydrated dichloromethane (2.9 mL) and dehydrated acetonitrile (0.9 mL) added thereto. Thereafter, 2'-OMe-G-CE phosphoramidite (151 mg, 173 μmol) and 5-ethylthio-1H-tetrazole (22.6 mg, 173 μmol) were successively added, and the mixture was stirred at room temperature for 1 hr. Successively, to the reaction solution was added tetrahydrofurfuryl alcohol (19.5 μL, 866 μmol) and the mixture was stirred at room temperature for 30 min. Water (78 μL), pyridine (70 μL, 867 μmol) and iodine (89.3 mg, 352 μmol) were successively added, and the mixture was stirred at room temperature for 1 hr. Thereafter, 2,3-dimethylfuran (91.6 μL, 869 μmol) and trifluoroacetic acid (199 μL, 2.6 mmol) were successively added, and the mixture was stirred at room temperature for 1 hr. Analysis of the reaction solution revealed that the amount of trifluoroacetylated oligonucleic acid was 11%. To the reaction mixture were successively added collidine (692 μL, 5.2 mmol) and water (19 μL, 1.1 μmmol), and the mixture was stirred at room temperature for 2 hr. Analysis of the reaction solution revealed that the remaining amount of trifluoroacetylated oligonucleic acid was 0.07%. Thereafter, acetonitrile (15 mL) was added, the precipitated solid was filtered by suction with Kiriyama funnel, and dried to give a trimer HO-GmCmT-SUC-TOB as a white solid (103.2 mg).

m/z(TOF-MS): Calcd. 2211.20, Found 2212.23[M+H]$^+$

Example 4: Synthesis and Deprotection of Tetramer (HO-rCC$_f$A$_L$T-SUC-TOB)

Under an argon atmosphere, HO-T-SUC-TOB (300 mg, 242 μmol) and Piv-TOB (450 mg, 451 μmol) were placed in a 200 mL two-necked flask, and dissolved in dehydrated dichloromethane (12.1 mL) and dehydrated acetonitrile (3.6 mL) added thereto. Thereafter, LNA-A(Bz)-CE phosphoramidite (644 mg, 727 μmol) and 5-ethylthio-1H-tetrazole (94.6 mg, 727 μmol) were successively added, and the mixture was stirred at room temperature for 1.0 hr. Successively, to the reaction solution was added 2,2,2-trifluoroethanol (265 μL, 3.6 mmol) and the mixture was stirred at room temperature for 30 min. 2,6-Xylidine (506 μL, 4.1 mmol) and DDTT (174 mg, 848 μmol) were successively added, and the mixture was stirred at room temperature for 1.7 hr. Thereafter, indole (424 mg, 3.6 mmol) and trifluoroacetic acid (1.1 mL, 14.4 mmol) were successively added, and the mixture was stirred at room temperature for 1.0 hr. Analysis of the reaction solution at the completion of the DMTr step revealed that it contained 1.23% of trifluoroacetylated oligonucleic acid. Successively, pyridine (3.5 mL, 43.0 mmol) and water (180 μL) were successively added to the reaction solution, and the mixture was stirred at room temperature for 1.0 hr. Analysis of the reaction solution revealed that the remaining amount of trifluoroacetylated oligonucleic acid was 0.017%. Thereafter, acetonitrile (112 mL) was added, the precipitated solid was filtered by suction with Kiriyama funnel, and dried to give a dimer HO-A$_L$T-SUC-TOB as a white solid (829.9 mg, 95%)

m/z: Calcd. 1751.07, Found 1753.09[M+H]$^+$

Under an argon atmosphere, in a 200 mL two-necked flask, the obtained white solid (829.9 mg) was dissolved in dehydrated dichloromethane (11.5 mL) and dehydrated acetonitrile (3.4 mL) added thereto. Thereafter, 2'-F—C (Bz)-CE phosphoramidite (591 mg, 694 μmol) and 4,5-dicyanoimidazole (83.5 mg, 707 μmol) were successively added, and the mixture was stirred at room temperature for 1.0 hr. Successively, to the reaction solution was added 2,2,2-trifluoroethanol (251 μL, 3.5 mmol) and the mixture was stirred at room temperature for 30 min. 2,6-Xylidine (480 μL, 3.9 mmol) and DDTT (165 mg, 805 μmol) were successively added, and the mixture was stirred at room temperature for 2.0 hr. Thereafter, indole (402 mg, 3.43 mmol) and trifluoroacetic acid (1.0 mL, 13.6 mmol) were successively added, and the mixture was stirred at room temperature for 1.0 hr. Analysis of the reaction solution at the completion of the DMTr step revealed that it contained 2.74% of trifluoroacetylated oligonucleic acid. Successively, to the reaction solution were successively added pyridine (3.3 mL, 40.8 mmol) and water (170 μL), and the mixture was stirred at room temperature for 1.0 hr. Analysis of the reaction solution revealed that the remaining amount of trifluoroacetylated oligonucleic acid was 0.084%. Thereafter, acetonitrile (110 mL) was added, the precipitated solid was filtered by suction with Kiriyama funnel, and dried to give a trimer HO—C$_f$A$_L$T-SUC-TOB as a white solid (780.1 mg, 83%).

m/z: calcd. 2231.13, found 1117.07[M+2H]$^{2+}$

Under an argon atmosphere, in a 200 mL two-necked flask, the obtained white solid (718 mg) was dissolved in dehydrated dichloromethane (8.8 mL) and dehydrated acetonitrile (2.6 mL) added thereto. Thereafter, 2'-O-TBDMS-C(Ac)-CE phosphoramidite (475 mg, 527 μmol) and 5-ethylthio-1H-tetrazole (68.9 mg, 528 μmol) were successively added, and the mixture was stirred at room temperature for 1.0 hr. Successively, to the reaction solution was added 2,2,2-trifluoroethanol (192 μL, 2.6 mmol) and the mixture was stirred at room temperature for 30 min. 2,6-Xylidine (366 μL, 3.0 mmol) and DDTT (127 mg, 619 μmol) were successively added, and the mixture was stirred at room temperature for 1.0 hr. Thereafter, indole (307 mg, 2.6 mmol) and trifluoroacetic acid (796 μL, 10.4 mmol) were successively added, and the mixture was stirred at room temperature for 1.0 hr. Analysis of the reaction solution at the completion of the DMTr step revealed that it contained 2.73% of trifluoroacetylated oligonucleic acid. Successively, to the reaction solution were successively added pyridine (2.5 mL, 31.2 mmol) and water (130 μL), and the mixture was stirred at room temperature for 1.0 hr. Analysis of the reaction solution revealed that the remaining amount of trifluoroacetylated oligonucleic acid was 0.070%. Thereafter, acetonitrile (100 mL) was added, the precipitated solid was filtered by suction with Kiriyama funnel, and dried to give a tetramer HO-rCC$_f$A$_L$T-SUC-TOB as a white solid (758.5 mg, 94%).

m/z: calcd. 2761.27, found 1382.15[M+2H]$^{2+}$

Deprotection

A mixture of the white solid (10 mg) obtained above and 30 wt % aqueous ammonia (5.0 mL) was placed in an autoclave, heated at 65° C. for 4 hr, and then cooled to room temperature. After removing the insoluble material in the reaction solution with a syringe filter, the mixture was concentrated under reduced pressure by a centrifugal evaporator. Then, the concentrate was freeze-dried to give the desired product 2'-O-(tert-butyldimethylsilyl)-cytidine-3'-phosphorothionyl-2'-deoxy-2'-fluoro-cytidine-3'-phosphorothionyl-2'-O,4'-C-methylene-adenosine-3'-phosphorothionyl-deoxythymidine.

m/z: calcd. 1357.24, found 1356.23[M−H]$^-$

Example 5: Synthesis and Deprotection of Trimer (HO-rCC$_f$A$_L$ (CH$_2$)$_2$—SUC-TOB)

Under an argon atmosphere, HO—(CH$_2$)$_2$—SUC-TOB (256 mg, 242 µmol) and Piv-TOB (385 mg, 386 µmol) were placed in a 200 mL two-necked flask, and dissolved in dehydrated dichloromethane (12.1 mL) and dehydrated acetonitrile (3.6 mL) added thereto. Thereafter, LNA-A(Bz)-CE phosphoramidite (644 mg, 727 µmol) and 5-ethylthio-1H-tetrazole (94.7 mg, 727 µmol) were successively added, and the mixture was stirred at room temperature for 1.0 hr. Successively, to the reaction solution was added 2,2,2-trifluoroethanol (265 µL, 3.6 mmol) and the mixture was stirred at room temperature for 30 min. 2,6-Xylidine (506 µL, 4.1 mmol) and DDTT (174 mg, 848 µmol) were successively added, and the mixture was stirred at room temperature for 1.7 hr. Thereafter, indole (424 mg, 3.6 mmol) and trifluoroacetic acid (1.1 mL, 14.4 mmol) were successively added, and the mixture was stirred at room temperature for 1.0 hr. Analysis of the reaction solution at the completion of the DMTr step revealed that it contained 1.76% of trifluoroacetylated oligonucleic acid. Successively, to the reaction solution were successively added pyridine (3.5 mL, 43.1 mmol) and water (180 µL), and the mixture was stirred at room temperature for 1.0 hr. Analysis of the reaction solution revealed that the remaining amount of trifluoroacetylated oligonucleic acid was 0.015%. Thereafter, acetonitrile (120 mL) was added, the precipitated solid was filtered by suction with Kiriyama funnel, and dried to give HO-A$_L$(CH$_2$)$_2$—SUC-TOB as a white solid (762 mg, quantitatively).

m/z: calcd. 1571.01, found 1572.04[M+H]$^+$

Under an argon atmosphere, the obtained white solid (762 mg) was placed in a 200 mL two-necked flask, and dissolved in dehydrated dichloromethane (12.1 mL) and dehydrated acetonitrile (3.6 mL) added thereto. Thereafter, 2'-F—C(Bz)-CE phosphoramidite (615 mg, 724 µmol) and 4,5-dicyanoimidazole (86.2 mg, 730 µmol) were successively added, and the mixture was stirred at room temperature for 1.0 hr. Successively, to the reaction solution was added 2,2,2-trifluoroethanol (264 µL, 3.6 mmol) and the mixture was stirred at room temperature for 30 min. 2,6-Xylidine (503 µL, 4.1 mmol) and DDTT (173 mg, 844 µmol) were successively added, and the mixture was stirred at room temperature for 2.0 hr. Thereafter, indole (422 mg, 3.6 mmol) and trifluoroacetic acid (1.1 mL, 14.3 mmol) were successively added, and the mixture was stirred at room temperature for 1.0 hr. Analysis of the reaction solution at the completion of the DMTr step revealed that it contained 2.95% of trifluoroacetylated oligonucleic acid. Successively, to the reaction solution were successively added pyridine (3.5 mL, 42.8 mmol) and water (179 µL), and the mixture was stirred at room temperature for 1.0 hr. Analysis of the reaction solution revealed that the remaining amount of trifluoroacetylated oligonucleic acid was 0.076%. Thereafter, acetonitrile (120 mL) was added, the precipitated solid was filtered by suction with Kiriyama funnel, and dried to give a dimer HO—C$_f$A$_L$(CH$_2$)$_2$—SUC-TOB as a white solid (817.7 mg, 94%).

m/z: calcd. 2051.0789, found 1027.05 [M+2H]$^{2+}$

Under an argon atmosphere, the obtained white solid (640 mg) was placed in a 200 mL two-necked flask, and dissolved in dehydrated dichloromethane (8.8 mL) and dehydrated acetonitrile (2.6 mL) added thereto. Thereafter, 2'-O-TBDMS-C(Ac)-CE phosphoramidite (476 mg, 528 µmol) and 5-ethylthio-1H-tetrazole (68.5 mg, 527 µmol) were successively added, and the mixture was stirred at room temperature for 1.0 hr. Successively, to the reaction solution was added 2,2,2-trifluoroethanol (192 µL, 2.6 mmol) and the mixture was stirred at room temperature for 30 min. 2,6-Xylidine (367 µL, 2.9 mmol) and DDTT (126 mg, 613 µmol) were successively added, and the mixture was stirred at room temperature for 1 hr. Thereafter, indole (308 mg, 2.6 mmol) and trifluoroacetic acid (797 µL, 10.4 mmol) were successively added, and the mixture was stirred at room temperature for 1.0 hr. Analysis of the reaction solution at the completion of the DMTr step revealed that it contained 2.79% of trifluoroacetylated oligonucleic acid. Successively, to the reaction solution were successively added pyridine (2.5 mL, 31.2 mmol) and water (130 µL), and the mixture was stirred at room temperature for 1.0 hr. Analysis of the reaction solution revealed that the remaining amount of trifluoroacetylated oligonucleic acid was 0.051%. Thereafter, acetonitrile (100 mL) was added, the precipitated solid was filtered by suction with Kiriyama funnel, and dried to give a trimer HO-rCC$_f$A$_L$(CH$_2$)$_2$—SUC-TOB as a white solid (690.6 mg, 95%).

m/z: calcd. 2581.22, found 1292.11[M+2H]$^{2+}$

Deprotection

A mixture of the white solid (10 mg) obtained above and 30 wt % aqueous ammonia (5.0 mL) was placed in an autoclave, heated at 65° C. for 4 hr, and then cooled to room temperature. After removing the insoluble material in the reaction solution with a syringe filter, the mixture was concentrated under reduced pressure by a centrifugal evaporator. Then, the concentrate was freeze-dried to give the desired product 2'-O-(tert-butyldimethylsilyl)-cytidine-3'-phosphorothionyl-2'-deoxy-2'-fluoro-cytidine-3'-phosphorothionyl-2'-O,4'-C-methylene-adenosine-3'-phosphorothionyl-ethanol.

m/z: calcd. 1177.18, found 1176.18[M−H]$^-$

Example 6: Synthesis of Dimer Using H-Phosphonate

Under an argon atmosphere, HO-T-SUC-TOB (100 mg, 80.8 µmol) and dT-H-phosphonate TEA salt (115.7 mg, 163 µmol) were placed in a 50 mL two-necked flask, and dissolved in dehydrated dichloromethane (2.0 mL) and dehydrated pyridine (2.0 mL) added thereto. Thereafter, PivCl (29.5 µl, 242 µmol) was added and the mixture was stirred at room temperature for 2.0 hr. Thereafter, acetonitrile (30 mL) was added, and the precipitated solid was filtered by suction with Kiriyama funnel, and dried to give a white solid (133 mg). Under an argon atmosphere, the obtained solid was placed in a 50 mL two-necked flask, and dissolved in dehydrated dichloromethane (3.6 mL) and dehydrated acetonitrile (1.1 mL) added thereto. Thereafter, indole (42.5 mg, 363 μmol) and trifluoroacetic acid (66.7 μL, 871 μmol) were successively added, and the mixture was stirred at room temperature for 1.0 hr. Successively, to the reaction solution were successively added pyridine (211 μL, 2.6 mmol) and water (47 μL), and the mixture was stirred at room temperature for 1.0 hr. Thereafter, acetonitrile (30 mL) was added, and the precipitated solid was filtered by suction with Kiriyama funnel, and dried to give a dimer HO-$T_H$T-SUC-TOB as a white solid (82.2 mg, 74%).

m/z: calcd. 1525.03, found 1526.05[M+H]$^+$

Under an argon atmosphere, HO-T-SUC-TOB (99.1 mg, 80.0 μmol) and dT-H-phosphonate TEA salt (115.1 mg, 162 μmol) were placed in a 50 mL two-necked flask, and dissolved in dehydrated dichloromethane (2.0 mL) and dehydrated pyridine (2.0 mL) added thereto. Thereafter, PivCl (29.5 μl, 242 μmol) was added and the mixture was stirred at room temperature for 1.0 hr. Successively, to the reaction solution were added DBU (48.4 μL, 324 μmol) and DDTT (33.3 mg, 162 μmol) and the mixture was stirred at room temperature for 40 min. Thereafter, acetonitrile (30 mL) was added, and the precipitated solid was filtered by suction with Kiriyama funnel, and dried to give a white solid (133 mg). Under an argon atmosphere, the obtained solid was placed in a 50 mL two-necked flask, and dissolved in dehydrated dichloromethane (3.9 mL) and dehydrated acetonitrile (1.2 mL) added thereto. Thereafter, indole (45.6 mg, 389 μmol) and trifluoroacetic acid (71.6 μL, 910 μmol) were successively added, and the mixture was stirred at room temperature for 1.0 hr. Successively, to the reaction solution were successively added pyridine (226 μL, 2.8 mmol) and water (51 μL), and the mixture was stirred at room temperature for 1.0 hr. Thereafter, acetonitrile (30 mL) was added, and the precipitated solid was filtered by suction with Kiriyama funnel, and dried to give a dimer HO-$T_{OH}$T-SUC-TOB as a white solid (107.3 mg, 89%)

m/z: calcd. 1541.03, found 1542.04[M+H]$^+$

Example 7: Experiment Using Trichloroacetic Acid

Under an argon atmosphere, HO-Um-SUC-TOB (102.4 mg, 81.7 μmol) and Piv-TOB (105 mg, 105 μmol) were placed in a 50 mL two-necked flask, and dissolved in dehydrated dichloromethane (4.0 mL) and dehydrated acetonitrile (1.2 mL) added thereto. Thereafter, dG-CE phosphoramidite (135.1 mg, 161 μmol) and 5-ethylthio-1H-tetrazole (21.4 mg, 164 μmol) were successively added, and the mixture was stirred at room temperature for 1.0 hr. Successively, to the reaction solution was added 2,2,2-trifluoroethanol (58.1 μL, 797 μmol) and the mixture was stirred at room temperature for 30 min. 2,6-Xylidine (118 μL, 955 μmol) and DDTT (40.9 mg, 199 μmol) were successively added, and the mixture was stirred at room temperature for 1.0 hr. Thereafter, indole (93.6 mg, 799 μmol) and trichloroacetic acid (698 mg, 4.27 mmol) were successively added, and the mixture was stirred at room temperature for 1.0 hr. Successively, to the reaction solution were successively added pyridine (1.01 mL, 12.6 mmol) and water (66 μl), and the mixture was stirred at room temperature for 1.0 hr. Thereafter, acetonitrile (30 mL) was added, and the precipitated solid was filtered by suction with Kiriyama funnel, and dried to give a dimer HO-GUm-SUC-TOB as a white solid (241.5 mg).

m/z: calcd. 1721.07, found 1723.10[M+H]$^+$

Example 8: Experiment Using Dichloroacetic Acid

Under an argon atmosphere, HO-Um-SUC-TOB (99.6 mg, 79.4 μmol) and Piv-TOB (97.9 mg, 98.0 μmol) were placed in a 50 mL two-necked flask, and dissolved in dehydrated dichloromethane (4.0 mL) and dehydrated acetonitrile (1.2 mL) added thereto. Thereafter, dG-CE phosphoramidite (134.2 mg, 160 μmol) and 5-ethylthio-1H-tetrazole (20.9 mg, 161 μmol) were successively added, and the mixture was stirred at room temperature for 1.0 hr. Successively, to the reaction solution was added 2,2,2-trifluoroethanol (58.1 μL, 797 μmol) and the mixture was stirred at room temperature for 30 min. 2,6-Xylidine (118 μL, 955 μmol) and DDTT (40.9 mg, 199 μmol) were successively added, and the mixture was stirred at room temperature for 1.0 hr. Thereafter, indole (93.2 mg, 796 μmol) and dichloroacetic acid (478 μl, 5.78 mmol) were successively added, and the mixture was stirred at room temperature for 1.0 hr. Successively, to the reaction solution were successively added pyridine (1.40 mL, 17.4 mmol) and water (61 μL), and the mixture was stirred at room temperature for 1.0 hr. Thereafter, acetonitrile (40 mL) was added, and the precipitated solid was filtered by suction with Kiriyama funnel, and dried to give a dimer HO-GUm-SUC-TOB as a white solid (228.7 mg, 96%).

m/z: calcd. 1721.07, found 1723.10[M+H]$^+$

INDUSTRIAL APPLICABILITY

According to the method for producing oligonucleotide of the present invention, the condensation reaction can be completed to improve the condensation yield, and impurities such as single base deletion form (N-1mer) and the like can be markedly reduced. The oligonucleotide obtained by the production method of the present invention can be used for various applications such as pharmaceutical products (RNA, DNA, oligonucleic acid medicine etc.) for human or animal, functional food, food for specified health uses, food, chemical product, polymer material for living body or industrial use, and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing an oligonucleotide, comprising removing a temporary protecting group of a 5'-hydroxyl group by adding an acid to a protected oligonucleotide having a phosphorothioate (PS), phosphate (PO), or H-phosphonate moiety, and deacylating a by-product having an acylated 5'-hydroxyl group by solvolysis, wherein the solvent used for solvolysis is a mixture of a base and a nucleophilic substance, the base is at least one member selected from the group consisting of pyridine, collidine, lutidine, and methylpyridine, and the nucleophilic substance is at least one member selected from the group consisting of water, methanol, ethanol, isopropyl alcohol, butanol, benzyl alcohol, and tetrahydrofurfuryl alcohol.

2. A method for producing an oligonucleotide, comprising:

(1) condensing a nucleoside, nucleotide or oligonucleotide (a) wherein a 5'-hydroxy group is not protected, and other groups are each optionally protected by a protecting group used for nucleic acid synthesis or bonded to a solid phase carrier with another nucleoside, nucleotide or oligonucleotide (b) wherein a 3'-hydroxyl group or a 3'-amino group is modified by a method selected from a phosphoramidite method, an H-phosphonate method, a dihalophosphine method, or an oxazaphospholidine method, the 5'-hydroxyl group is protected by a temporary protecting group that can be removed under acidic conditions, and other groups are each optionally protected by a protecting group used for nucleic acid synthesis to obtain a phosphite form or phosphorous acid diester (c) in which the 5'-hydroxyl group remains protected by a temporary protecting group that can be removed under acidic conditions;

(2): (2-1) sulfurizing the phosphite form or phosphorous acid diester (c) by adding a sulfurizing agent to obtain an oligonucleotide (d-1) having a phosphorothioated moiety in which the 5'-hydroxyl group remains protected by a temporary protecting group that can be removed under acidic conditions, or (2-2) oxidizing the phosphite form or phosphorous acid diester (c) by adding an oxidizing agent to obtain an oligonucleotide (d-2) having a phosphated moiety in which the 5'-hydroxyl group remains protected by a temporary protecting group that can be removed under acidic conditions;

(3): (3-1) adding an acid to the oligonucleotide (d-1) having a phosphorothioated moiety to remove the temporary protecting group of the 5'-hydroxyl group, thereby obtaining a crude product of an oligonucleotide (e-1) having a phosphorothioated moiety in which the 5'-hydroxyl group is not protected, or (3-2) adding an acid to the oligonucleotide (d-2) having a phosphated moiety to remove the temporary protecting group of the 5'-hydroxyl group, thereby obtaining a crude product of an oligonucleotide (e-2) having a phosphated moiety in which the 5'-hydroxyl group is not protected; and (4): (4-1) deacylating by solvolysis a remaining oligonucleotide having an acylated 5'-hydroxyl group, which is contained in a crude product of the oligonucleotide (e-1) having the phosphorothioated moiety, or (4-2) deacylating by solvolysis a remaining oligonucleotide having an acylated 5'-hydroxyl group contained in a crude product of the oligonucleotide (e-2) having a phosphated moiety, wherein the solvent used for solvolysis is a mixture of a base and a nucleophilic substance, the base is at least one member selected from the group consisting of pyridine, collidine, lutidine, and methylpyridine, and the nucleophilic substance is at least one member selected from the group consisting of water, methanol, ethanol, isopropyl alcohol, butanol, benzyl alcohol, and tetrahydrofurfuryl alcohol.

3. The production method according to claim 2, further comprising removing all protecting groups of the oligonucleotide (e-1) having a phosphorothioated moiety or oligonucleotide (e-2) having a phosphated moiety, and then isolating an oligonucleotide having an unprotected phosphorothioated moiety or an oligonucleotide having an unprotected phosphated moiety.

4. A method for producing an oligonucleotide, comprising:

(1A) obtaining a phosphite form or phosphorous acid diester (c) in which the 5'-hydroxyl group is protected by a temporary protecting group that can be removed under acidic conditions by condensing a nucleoside, nucleotide or oligonucleotide (a) wherein a 5'-hydroxy group is not protected, and other groups are each optionally protected by a protecting group used for nucleic acid synthesis or bonded to a solid phase carrier, with another nucleoside, nucleotide, or oligonucleotide (b) wherein a 3'-hydroxyl group or a 3'-amino group is modified by an H-phosphonate method, the 5'-hydroxyl group is protected by a temporary protecting group that can be removed under acidic conditions, and other groups are each optionally protected by a protecting group used for nucleic acid synthesis;

(3A) adding an acid to the phosphite form or phosphorous acid diester (c) to remove the temporary protecting group of the 5'-hydroxyl group, thereby obtaining a phosphite form or a crude product of a phosphorous acid diester (c) wherein the 5'-hydroxyl group is not protected; and (4A) solvolyzing a remaining oligonucleotide having an acylated 5'-hydroxyl group contained in the phosphite form or a crude product of phosphorous acid diester (c) to achieve deacylation, wherein the solvent used for solvolysis is a mixture of a base and a nucleophilic substance, the base is at least one member selected from the group consisting of pyridine, collidine, lutidine, and methylpyridine, and the nucleophilic substance is at least one member selected from the group consisting of water, methanol, ethanol, isopropyl alcohol, butanol, benzyl alcohol, and tetrahydrofurfuryl alcohol.

5. The production method according to claim 2, wherein the step (1) comprises condensing a nucleoside, nucleotide, or oligonucleotide (a) wherein a 5'-hydroxy group is not protected, at least one group selected from an amino group, or an imino group of a nucleic acid base, a 2'-hydroxy group, a 3'-hydroxy group, or a 3'-amino group of a ribose residue, or a 3'-hydroxy group, or a 3'-amino group of a deoxyribose residue is protected by a protecting group unremovable under acidic conditions but removable under basic conditions, and other groups are each optionally further protected by a protecting group used for nucleic acid synthesis, or a nucleoside, nucleotide, or oligonucleotide (a1) wherein a 5'-hydroxy group is not protected, one OH of a 3'-terminal phosphate group is replaced by —OLn1-OH wherein Ln1 is an organic group, the hydroxy group of —OLn1-OH is protected by a protecting group unremovable under acidic conditions but removable under basic conditions, and other groups are each optionally further protected by a protecting group used for nucleic acid synthesis, with another nucleoside, nucleotide, or oligonucleotide (b) wherein a 3'-hydroxy group or 3'-amino group is modified by a method selected from a phosphoramidite method, an H-phosphonate method, a dihalophosphine method, or an oxazapholidine method, a 5'-hydroxy group is protected by a temporary protecting group removable under acidic conditions, and other groups are each optionally further protected by a protecting group selected from protecting groups unremovable under acidic conditions but removable under basic conditions or protecting groups used for nucleic acid synthesis to obtain a phosphite form or phosphorous acid diester (c) in which the 5'-hydroxyl group remains protected by a temporary protecting group that can be removed under acidic conditions.

6. The production method according to claim 1, wherein the acid used for removing the temporary protecting group of the 5'-hydroxyl group comprises carboxylic acid, sulfonic acid, phosphonic acid, or phosphoric acid.

7. The production method according to claim 6, wherein the acid is trifluoroacetic acid, dichloroacetic acid, trichloroacetic acid, acetic acid, trifluoromethanesulfonic acid, methanesulfonic acid, p-toluenesulfonic acid, phosphonic acid, or phosphoric acid.

8. A method for producing an oligonucleotide, comprising removing a temporary protecting group of a 3'-hydroxyl group or a 3'-amino group by adding an acid to a protected oligonucleotide having a phosphorothioate (PS), phosphate (PO), or H-phosphonate moiety, and deacylating a by-product with an acylated 3'-hydroxyl group or 3'-amino group by solvolysis, wherein the solvent used for solvolysis is a mixture of a base and a nucleophilic substance, the base is at least one member selected from the group consisting of pyridine, collidine, lutidine, and methylpyridine, and the nucleophilic substance is at least one member selected from the group consisting of water, methanol, ethanol, isopropyl alcohol, butanol, benzyl alcohol, and tetrahydrofurfuryl alcohol.

9. A method for producing an oligonucleotide, comprising:

(1') condensing a nucleoside, nucleotide, or oligonucleotide (a') wherein a 3'-hydroxyl group or 3'-amino group is not protected, and other groups are each optionally protected by a protecting group used for nucleic acid synthesis or bonded to a solid phase carrier, [and] with another nucleoside, nucleotide, or oligonucleotide (b') wherein a 5'-hydroxyl group is modified by a method selected from a phosphoramidite method, an H-phosphonate method, a dihalophosphine method, or an oxazapholidine method, the 3'-hydroxyl group or 3'-amino group is protected by a temporary protecting group that can be removed under acidic conditions, and other groups are each optionally protected by a protecting group used for nucleic acid synthesis to obtain a phosphite form or phosphorous acid diester (c') in which the 3'-hydroxyl group or 3'-amino group remains protected by a temporary protecting group that can be removed under acidic conditions;

(2'): (2'-1) sulfurizing the phosphite form or phosphorous acid diester (c') by adding a sulfurizing agent to obtain oligonucleotide (d'-1) having a phosphorothioated moiety in which the 3'-hydroxyl group or 3'-amino group remains protected by a temporary protecting group that can be removed under acidic conditions, or (2'-2) oxidizing the phosphite form or phosphorous acid diester (c') by adding an oxidizing agent to obtain oligonucleotide (d'-2) having a phosphated moiety in which the 3'-hydroxyl group or 3'-amino group remains protected by a temporary protecting group that can be removed under acidic conditions;

(3'): (3'-1) adding an acid to the oligonucleotide (d'-1) having a phosphorothioated moiety to remove the temporary protecting group of the 3'-hydroxyl group or 3'-amino group, thereby obtaining a crude product of an oligonucleotide (e'-1) having a phosphorothioated moiety in which the 3'-hydroxyl group or 3'-amino group is not protected, or (3'-2) adding an acid to the oligonucleotide (d'-2) having a phosphated moiety to remove the temporary protecting group of the 3'-hydroxyl group or 3'-amino group, thereby obtaining a crude product of an oligonucleotide (e'-2) having a phosphated moiety in which the 3'-hydroxyl group or 3'-amino group is not protected; and (4'): (4'-1) deacylating by solvolysis a remaining oligonucleotide having a phosphorothioated moiety having an acylated 3'-hydroxyl group or 3'-amino group, which is contained in a crude product of the oligonucleotide (e'-1) having the phosphorothioated moiety, or (4'-2) solvolyzing a remaining oligonucleotide having a phosphated moiety in which the 3'-hydroxyl group or 3'-amino group is acylated, and contained in a crude product of the oligonucleotide (e'-2) having a phosphated moiety, wherein the solvent used for solvolysis is a mixture of a base and a nucleophilic substance, the base is at least one member selected from the group consisting of pyridine, collidine, lutidine, and methylpyridine, and the nucleophilic substance is at least one member selected from the group consisting of water, methanol, ethanol, isopropyl alcohol, butanol, benzyl alcohol, and tetrahydrofurfuryl alcohol.

* * * * *